United States Patent
Jirgensons et al.

(10) Patent No.: US 11,072,581 B2
(45) Date of Patent: Jul. 27, 2021

(54) N-ACYL-ARYLSULFONAMIDE DERIVATIVES AS AMINOACYL-TRNA SYNTHETASE INHIBITORS

(71) Applicant: Oxford Drug Design Limited, London (GB)

(72) Inventors: Aigars Jirgensons, Riga (LV); Einars Loza, Riga (LV); Michael Charlton, Oxford (GB); Paul William Finn, Oxford (GB); Lluis Ribas De Pouplana, Barcelona (ES); Adelaide Saint-Léger, Hospitalet de Llobregat (ES)

(73) Assignee: Oxford Drug Design Limited, London (GB)

( * ) Notice: Subject to any disclaimer, the term of this patent is extended or adjusted under 35 U.S.C. 154(b) by 128 days.

(21) Appl. No.: 15/550,839

(22) PCT Filed: Feb. 11, 2016

(86) PCT No.: PCT/LV2016/000001
§ 371 (c)(1),
(2) Date: Aug. 14, 2017

(87) PCT Pub. No.: WO2016/129983
PCT Pub. Date: Aug. 18, 2016

(65) Prior Publication Data
US 2018/0022696 A1 Jan. 25, 2018

(30) Foreign Application Priority Data

Feb. 13, 2015 (LV) ........................ P-15-14
Feb. 10, 2016 (LV) ........................ P-16-06

(51) Int. Cl.
| | | |
|---|---|---|
| C07C 311/51 | (2006.01) | |
| C07D 213/71 | (2006.01) | |
| C07D 215/06 | (2006.01) | |
| C07D 215/36 | (2006.01) | |
| C07D 217/04 | (2006.01) | |
| C07D 217/22 | (2006.01) | |
| C07D 217/26 | (2006.01) | |
| C07D 239/42 | (2006.01) | |
| C07D 239/47 | (2006.01) | |
| C07D 239/48 | (2006.01) | |
| C07D 251/22 | (2006.01) | |
| C07D 311/04 | (2006.01) | |
| C07D 311/20 | (2006.01) | |
| C07D 487/04 | (2006.01) | |

(52) U.S. Cl.
CPC .......... *C07C 311/51* (2013.01); *C07D 213/71* (2013.01); *C07D 215/06* (2013.01); *C07D 215/36* (2013.01); *C07D 217/04* (2013.01); *C07D 217/22* (2013.01); *C07D 217/26* (2013.01); *C07D 239/42* (2013.01); *C07D 239/47* (2013.01); *C07D 239/48* (2013.01); *C07D 251/22* (2013.01); *C07D 311/04* (2013.01); *C07D 311/20* (2013.01); *C07D 487/04* (2013.01); *C07C 2601/02* (2017.05)

(58) Field of Classification Search
CPC combination set(s) only.
See application file for complete search history.

(56) References Cited

U.S. PATENT DOCUMENTS

| 2011/0230350 A1 | 9/2011 | Frackenpohl et al. |
| 2020/0039929 A1 | 2/2020 | Finn et al. |

FOREIGN PATENT DOCUMENTS

| CN | 1906208 A | 1/2007 |
| CN | 105198789 A | 12/2015 |
| JP | H05-208914 A | 8/1993 |
| JP | 2004-502670 A | 1/2004 |
| WO | WO-98/41215 A1 | 9/1998 |
| WO | WO-02/02513 A1 | 1/2002 |
| WO | WO-02/098848 A1 | 12/2002 |
| WO | WO-2005/037860 A2 | 4/2005 |
| WO | WO-2014/018569 A1 | 1/2014 |
| WO | WO-2016/129983 A1 | 8/2016 |
| WO | WO-2018/065611 A1 | 4/2018 |

OTHER PUBLICATIONS

Anderson et al 'The Process of Structure-Based Drug Design' Chemistry and Biology, vol. 10, p. 787-797, 2003.*
Thiel 'Structure-aided drug design's next generation' Nature Biotechnology, 22(5), p. 513-519, 2004.*
STN record CAS RN: 625122-57-8 (Dec. 9, 2003).*
Chemical Abstracts, Chemical Compounds with Registry Nos. 1786215-48-2; 1786212-05-2; 1786200-20-1; and 1786086-91-6 (2015) (2 pages).

(Continued)

*Primary Examiner* — Jared Barsky
(74) *Attorney, Agent, or Firm* — Clark & Elbing LLP

(57) ABSTRACT

The present invention relates to novel N-acyl-diarysulfonamides acting as inhibitors of bacterial aminoacyl-tRNA synthetase. These can be used as medicines or as constituent of medicines for the treatment of bacterial infections.

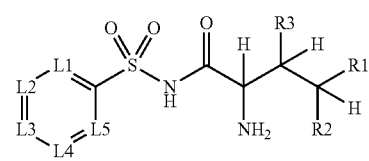

19 Claims, No Drawings

(56) References Cited

OTHER PUBLICATIONS

Chen et al., "Chiral Molecular Clips Control Orthogonal Crystalline Organization," Org Lett. 9(10):1899-1902 (2007).
Gadakh et al., "Aminoacyl-tRNA synthetase inhibitors as antimicrobial agents: a patent review from 2006 till present," Expert Opin Ther Pat. 22(12): 1453-65 (2012).
Hurdle et al., "Prospects for aminoacyl-tRNA synthetase inhibitors as new antimicrobial agents," Antimicrobial Agents and Chemotherapy. 49(12): 4821-33 (2005).
Kerrigan et al., "Synthesis of arylpiperazines via palladium-catalysed aromatic amination reactions of bromoarenes with N-tert-butoxycarbonylpiperazine," Tetrahedron Letters. 39(15): 2219-22 (1998).
Laupland et al., "Treatment of *Staphylococcus aureus* colonization and prophylaxis for infection with topical intranasal mupirocin: An evidence-based review," Clin Infect Dis. 37(7): 933-8 (2003).
Ochsner et al., "Aminoacyl-tRNA synthetases: essential and still promising targets for new anti-infective agents," Expert Opin Investig Drugs. 16(5): 573-93 (2007).
Pham et al., "Aminoacyl-tRNA synthetases as drug targets in eukaryotic parasites," Int J Parasitol Drugs Drug Resist. 4(1):1-13 (2014).
Savile et al., "Subtilisin-catalyzed resolution of N-acyl arylsulfinamides," J Am Chem Soc. 127(7): 2104-13 (2005).
Shi et al., "Discovery of a series of novel compounds with moderate anti-hepatitis C virus NS3 protease activity in vitro," Bioorg Med Chem. 23(17): 5539-45 (2015).
Thea et al., "Sulfoquinones in the hydrolysis of aryl esters of o- and p-hydroxyarenesulfonic acids in alkaline aqueous solutions of dioxane," J Org Chem. 50(12): 2158-65 (1985).
Vondenhoff et al., "Aminoacyl-tRNA synthetase inhibitors as potential antibiotics," Eur J Med Chem. 46(11): 5227-36 (2011).
Zhang et al., "Discovery of N-(4-sulfamoylphenyl)thioureas as Trypanosoma brucei leucyl-tRNA synthetase inhibitors," Org Biomol Chem. 11(32): 5310-24 (2013).
Chemical Abstracts, Chemical Compounds with Registry Nos. 1279200-48-4; 1279037-24-9; 775277-16-2; 765873-02-7 (2019) (1 page).
Chemical Abstracts, Chemical Compounds with Registry Nos. 1786245-31-5; 1786215-48-2; 1786212-05-2; 1786204-28-1; 1786200-20-1; 1786109-38-3; 1786096-26-1; 1786086-91-6; 1279200-48-4; 1279037-24-9 (2019) (5 pages).
International Preliminary Report on Patentability for International Patent Application No. PCT/LV2016/000001, dated Aug. 15, 2017 (8 pages).
International Search Report and Written Opinion for International Patent Application No. PCT/LV2016/000001, dated Jan. 4, 2016 (11 pages).
Johansson et al., "Acyl sulfonamides as potent protease inhibitors of the hepatitis C virus full-length $NS_3$ (protease-helicase/NTPase): A comparative study of different C-terminals," Bioorg Med Chem. 11(12):2551-68 (2003).
Orelle et al., "Identifying the targets of aminoacyl-tRNA synthetase inhibitors by primer extension inhibition," Nucleic Acids Res. 41(14):e144 (2013).
Zheng et al., "One-pot asymmetric synthesis of 2-aryl-2,3-dihydro-4-quinolones catalyzed by amino acid-derived sulfonamides," Tetrahedron: Asymmetry. 24:875-882 (2013).

\* cited by examiner

N-ACYL-ARYLSULFONAMIDE DERIVATIVES AS AMINOACYL-TRNA SYNTHETASE INHIBITORS

FIELD OF INVENTION

The present invention relates to medicine and in particular to the treatment of bacterial infections, more particularly to inhibitors of bacterial aminoacyl-tRNA synthetase. Even more particularly, the invention relates to novel N-acyl-aryl sulfonamides and pharmaceutical compositions thereof and their use as inhibitors for aminoacyl-tRNA synthetases.

BACKGROUND OF INVENTION

Widespread resistance to currently used antibacterial drugs has activated the search for novel chemotherapeutics with slow or completely blocked resistance development. This could be achieved by targeting the functional bacterial proteins mutation of which leads to reduction of bacterial fitness. Bacterial enzymes called aminoacyl-tRNA synthetases (aaRS) have been recognized as such molecular targets for new drug development (Gadakh, B. Van Aerschot, A. Aminoacyl-tRNA synthetase inhibitors as antimicrobial agents: a patent review from 2006 till present. Expert Opin. Ther. Patents 2012, 22, 1453-1465. Vondenhoff, G. H. M.; Van Aerschot A. Aminoacyl-tRNA synthetase inhibitors as potential antibiotics. Eur. J. Med. Chem. 2011, 46 5227-5236. Pham, J. S.; Dawson, K. L.; Jackson, K. E.; Lim, E. E.; Pasaje, C. F. A.; Turner, K. E. C.; Ralph. S. A. Aminoacyl-tRNA synthetases as drug targets in eukaryotic parasties. Int. J. Parasitol. Drugs Drug Resist. 2014, 4, 41-13.) Isoleucyl tRNA synthethase (IleRS) inhibitor Mupirocin is a clinically approved drug for topical treatment of infections caused by broad spectra of Gram-positive bacteria. Several inhibitors for other bacterial tRNA synthetases have been developed, however, so far none of them have been advanced to clinical studies.

SUMMARY OF THE INVENTION

In a first aspect, the invention features a method of treating bacterial infections in humans or animals, comprising administering to a human or animal in need thereof a therapeutically effective amount of a compound or prodrug thereof, or pharmaceutically acceptable salt, hydrate, solvate, or polymorph of said compound or prodrug, wherein the compound is an inhibitor of aminoacyl-tRNA synthetase.

In another aspect, the invention features a pharmaceutical composition for treatment of bacterial infections comprising a therapeutically effective amount of a composition comprising (i) a compound or prodrug thereof, or pharmaceutically acceptable salt, hydrate, solvate, or polymorph of said compound or prodrug; and (ii) a pharmaceutically acceptable carrier, wherein the compound is an inhibitor of aminoacyl-tRNA synthetase.

In another aspect, the invention features the use of a compound or prodrug thereof, or pharmaceutically acceptable salt, hydrate, solvate, or polymorph of said compound or prodrug, wherein the compound is an inhibitor of aminoacyl-tRNA synthetase, in the manufacture of a medicament for treatment or prevention of bacterial infections.

In another aspect, the invention features a compound or prodrug thereof, or pharmaceutically acceptable salt or ester of said compound or prodrug for use in treating or preventing bacterial infections, wherein the compound is an inhibitor of aminoacyl-tRNA synthetase.

In one embodiment the inhibitor of aminoacyl-tRNA synthetase is a compound of Formula I, generally referred herein as an N-Acyl-arysulfonamide derivative:

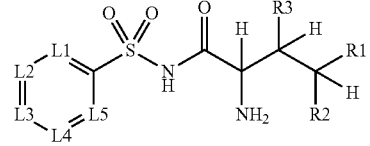

General formula I enantiomers, diastereomers, tautomers or pharmaceutically acceptable salts thereof, wherein:
R1 represents $C_{1-4}$alkyl;
R2 represents $C_{1-4}$alkyl or H;
R3 represents $C_{1-4}$alkyl or H;
$R_1$, $R_2$ or $R_1$, $R_3$ together with the atoms to which they are attached may form one of 3-membered to 6-membered rings;
provided that R2 and R3 are not both hydrogen;
provided that R1, R2 and R3 do not form a cycle together with L1 or L5;
L1 is independently C—R4 or N;
L2 is independently C—R5 or N;
L3 is independently C—R6 or N;
L4 is independently C—R7 or N;
L5 is independently C—R8 or N.
R4 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, C(=O)$R^a$, C(=O)O$R^a$, C(=O)N($R^a$)$R^b$, O$R^a$, OC(=O)$R^a$, OC(=O)N($R^a$)$R^b$, N($R^a$)$R^b$, N($R^a$)S(O)$_{0-2}R^6$, N($R^a$)C(=O)$R^b$, N($R^a$)C(=O)O$R^b$, S(O)$_{0-2}R^a$, S(O)$_{0-2}$N($R^a$)$R^b$, wherein said alkyl, alkenyl, alkynyl, aryl, heteroaryl, cycloalkyl and heterocyclyl are optionally substituted by 1 to 5 substituents independently selected from O$R^a$, N($R^a$)$R^b$, oxo, halo, S(O)$_{0-2}R^a$ and S(O)$_{0-2}$N($R^a$)$R^b$;
R5 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, C(=O)$R^a$, C(=O)O$R^a$, C(=O)N($R^a$)$R^b$, O$R^a$, OC(=O)$R^a$, OC(=O)N($R^a$)$R^b$, S(O)$_{0-2}R^a$, S(O)$_{0-2}$N($R^a$)$R^b$, wherein said alkyl, alkenyl, alkynyl, aryl, heteroaryl, cycloalkyl and heterocyclyl are optionally substituted by 1 to 5 substituents independently selected from O$R^a$, N($R^a$)$R^b$, oxo, halo, S(O)$_{0-2}R^a$ and S(O)$_{0-2}$N($R^a$)$R^b$; or R4 and R5 taken together with the atoms to which they are attached form a $C_{4-6}$ heterocyclic ring, $C_{4-6}$ carbocyclic ring, $C_6$ aromatic ring or $C_{5-6}$ heteroaromatic ring optionally substituted by halogen, C(=O)N($R^a$)$R^b$, oxo, O$R^a$, N($R^a$)$R^b$ or $C_{1-3}$alkyl;
R6 is independently H, halo, $C_{2-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, C(=O)$R^a$, C(=O)O$R^a$, C(=O)N($R^a$)$R^b$, O$R^a$, OC(=O)$R^a$, OC(=O)N($R^a$)$R^b$, S(O)$_{0-2}R^a$, S(O)$_{0-2}$N($R^a$)$R^b$, wherein said alkyl, alkenyl, alkynyl, aryl, heteroaryl, cycloalkyl and heterocyclyl are optionally substituted by 1 to 5 substituents independently selected from O$R^a$, N($R^a$)$R^b$, oxo, halo, S(O)$_{0-2}R^a$ and S(O)$_{0-2}$N($R^a$)$R^b$; or R5 and R6 taken together with the atoms to which they are attached form a $C_{4-6}$heterocyclic ring, $C_{4-6}$ carbocyclic ring, $C_6$ aromatic ring or $C_{5-6}$ heteroaromatic ring optionally substituted by halogen, C(=O)N($R^a$)$R^b$, oxo, O$R^a$, N($R^a$)$R^b$ or $C_{1-3}$alkyl;
R7 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^a$, $C(=O)OR^a$, $C(=O)N(R^a)R^b$, $OR^a$, $OC(=O)R^a$, $OC(=O)N(R^a)R^b$, $S(O)_{0-2}R^a$, $S(O)_{0-2}N(R^a)R^b$, wherein said alkyl, alkenyl, alkynyl, aryl, heteroaryl, cycloalkyl and heterocyclyl are optionally substituted by 1 to 5 substituents independently selected from $OR^a$, $N(R^a)R^b$, oxo, halo, $S(O)_{0-2}R^a$ and $S(O)_{0-2}N(R^a)R^b$ R8 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^a$, $C(=O)OR^a$, $C(=O)N(R^a)R^b$, $OR^a$, $OC(=O)R^a$, $OC(=O)N(R^a)R^b$, $N(R^a)R^b$, $N(R^a)S(O)_{0-2}R^b$, $N(R^a)C(=O)R^b$, $N(R^a)C(=O)OR^b$, $S(O)_{0-2}R^a$, $S(O)_{0-2}N(R^a)R^b$, wherein said alkyl, alkenyl, alkynyl, aryl, heteroaryl, cycloalkyl and heterocyclyl are optionally substituted by 1 to 5 substituents independently selected from $OR^a$, $N(R^a)R^b$, oxo, halo, $S(O)_{0-2}R^a$ and $S(O)_{0-2}N(R^a)R^b$;

$R^a$ and $R^b$ are independently H, $C_{1-6}$alkyl, $C_{5-6}$heteroaryl or $C_6$carboaryl, wherein each alkyl, heteroaryl or carboaryl are optionally substituted by 1 to 3 substituents selected from oxo, halo, $NH_2$, OH.

provided that R5 and R6 are not amino or substituted amino group.

provided that R6 is not methyl group.

In one preferred embodiment R1 is methyl, R2 is methyl and R3 is H.

In one preferred embodiment R1 is methyl, R2 is H and R3 is methyl.

In one preferred embodiment the radical

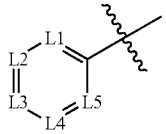

is pyridyl, quinolyl, isoquinolyl, naphthyl, benzopyranyl, tetrahydroisoquinolyl, optionally substituted with 1 to 4 substituents selected from halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^c$, $C(=O)OR^c$, $C(=O)N(R^c)R^d$, $OR^c$, $OC(=O)R^c$, $OC(=O)N(R^c)R^c$, $S(O)_{0-2}R^c$, $S(O)_{0-2}N(R^c)R^d$, wherein said alkyl, alkenyl, alkynyl, aryl, heteroaryl, cycloalkyl and heterocyclyl are optionally substituted by 1 to 5 substituents independently selected from $OR^c$, $N(R^c)R^d$, oxo, halo, $S(O)_{0-2}R^c$ and $S(O)_{0-2}N(R^c)R^d$;

$R^c$ and $R^d$ are independently H, $C_{1-8}$alkyl, $C_{3-8}$cycloalkyl, $C_{5-6}$heteroaryl or $C_6$carboaryl, wherein each alkyl, cycloalkyl, heteroaryl or aryl are optionally substituted by 1 to 3 substituents selected from oxo, halo, $NH_2$, OH.

In one preferred embodiment the radical

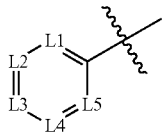

is pyridyl, quinolyl, isoquinolyl, naphthyl, benzopyranyl, tetrahydroisoquinolyl, optionally substituted with 1 to 2 substituents selected from halo, $C(=O)N(R^e)R^f$, $OR^e$; $NR^e$, $R^f$.

$R^e$ and $R^f$ are independently H, $C_{1-8}$alkyl optionally substituted by 1 to 3 substituents selected from oxo, halo, $NH_2$, OH.

In one preferred embodiment the radical:

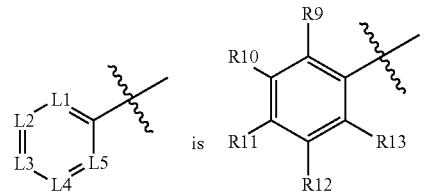

R9 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^e$, $C(=O)OR^e$, $C(=O)N(R^e)R^f$, $OR^e$, $OC(=O)R^e$, $OC(=O)N(R^e)R^f$, $N(R^e)R$, $N(R^e)S(O)_{0-2}R^f$, $N(R^e)C(=O)R^f$, $N(R^e)C(=O)OR^f$, $S(O)_{0-2}R^e$, $S(O)_{0-2}N(R^e)R^f$, wherein said alkyl, alkenyl, alkynyl, carboaryl, heteroaryl, cycloalkyl and heterocyclyl are optionally substituted by 1 to 5 substituents independently selected from $OR^e$, $N(R^e)R^f$, oxo, halo, $S(O)_{0-2}R^e$ and $S(O)_{0-2}N(R^e)R^f$;

R10 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^e$, $C(=O)OR^e$, $C(=O)N(R^e)R^f$, $OR^e$, $OC(=O)R^e$, $OC(=O)N(R^e)R^f$, $S(O)_{0-2}R^e$, $S(O)_{0-2}N(R^e)R^f$, wherein said alkyl, alkenyl, alkynyl, carboaryl, heteroaryl, cycloalkyl and heterocyclyl are optionally substituted by 1 to 5 substituents independently selected from $OR^e$, $N(R^e)R^f$, oxo, halo, $S(O)_{0-2}R^e$ and $S(O)_{0-2}N(R^e)R^f$;

R11 is independently H, halo, $C_{2-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^e$, $C(=O)OR^f$, $C(=O)N(R^e)R^f$, $OR^e$, $OC(=O)R^e$, $OC(=O)N(R^e)R^f$, $S(O)_{0-2}R^e$, $S(O)_{0-2}N(R^e)R^f$, wherein said alkyl, alkenyl, alkynyl, carboaryl, heteroaryl, cycloalkyl and heterocyclyl are optionally substituted by 1 to 5 substituents independently selected from $OR^e$, $N(R^e)R^f$, oxo, halo, $S(O)_{0-2}R^a$ and $S(O)_{0-2}N(R^a)R^b$;

R12 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^e$, $C(=O)OR^e$, $C(=O)N(R^e)R^f$, $OR^e$, $OC(=O)R^e$, $OC(=O)N(R^e)R^f$, $S(O)_{0-2}R^e$, $S(O)_{0-2}N(R^e)R^f$, wherein said alkyl, alkenyl, alkynyl, carboaryl, heteroaryl, cycloalkyl and heterocyclyl are optionally substituted by 1 to 5 substituents independently selected from $OR^e$, $N(R^e)R^f$, oxo, halo, $S(O)_{0-2}R^e$ and $S(O)_{0-2}N(R^e)R^f$;

R13 is independently H, halo, $C_{1-6}$alkyl, $C_{2-6}$alkenyl, $C_{2-6}$alkynyl, $C_{5-9}$heteroaryl, $C_{6-10}$carboaryl, $C_{3-6}$cycloalkyl, $C_{1-5}$heterocyclyl, CN, $C(=O)R^e$, $C(=O)OR^e$, $C(=O)N(R^e)R^f$, $OR^e$, $OC(=O)R^e$, $OC(=O)N(R^e)R^f$, $N(R^e)R^f$, $N(R^e)S(O)_{0-2}R^f$, $N(R^e)C(=O)R^f$, $N(R^e)C(=O)OR^f$, $S(O)_{0-2}R^e$, $S(O)_{0-2}N(R^e)R^f$, wherein said alkyl, alkenyl, alkynyl, carboaryl, heteroaryl, cycloalkyl and heterocyclyl are optionally substituted by 1 to 5 substituents independently selected from $OR^e$, $N(R^e)R^f$, oxo, halo, $S(O)_{0-2}R^e$ and $S(O)_{0-2}N(R^e)R^f$;

or R9 and R10 taken together with the atoms to which they are attached form a $C_{4-6}$ heterocyclic ring, $C_{4-6}$ carbocyclic ring, $C_6$ aromatic ring or $C_{5-6}$ heteroaromatic ring optionally substituted by halogen, $C(=O)N(R^e)R^f$, oxo, $OR^e$, $N(R^e)R^f$ or $C_{1-3}$alkyl;

or R10 and R11 taken together with the atoms to which they are attached form a $C_{4-6}$ heterocyclic ring, $C_{4-6}$ carbocyclic ring, $C_6$ aromatic ring or $C_{5-6}$ heteroaromatic ring optionally substituted by halogen, $C(=O)N(R^e)R^f$, oxo, $OR^e$, $N(R^e)R^f$ or $C_{1-3}$alkyl;

$R^e$ and $R^f$ are independently H, $C_{5-6}$heteroaryl or C6carboaryl, wherein each alkyl, heteroaryl or carboaryl are optionally substituted by 1 to 3 substituents selected from oxo, halo, $NH_2$, OH.

In one preferred embodiment R9 is independently H, halo, $C_{1-6}$alkyl, $C_6$ aryl.

In one preferred embodiment R9 is independently H, F, Cl, isopropyl or phenyl.

In one preferred embodiment R10 is independently H, halo, $C_{5-9}$heteroaryl, $C_{6-10}$carboaryl, wherein said heteroaryl and carboaryl are optionally substituted by 1 to 3 substituents independently selected from $NH_2$, $NMe_2$, SMe, methyl, ethyl, halo, OH, $OC_{1-4}$alkyl, or phenyl.

In one preferred embodiment R10 is independently H, halo, pyridyl, pyrimidyl, triazinyl, phenyl or purinyl wherein said heteroaryl and carboaryl are optionally substituted by 1 to 3 substituents independently selected from $NH_2$, $NMe_2$, SMe, methyl, ethyl, halo, OH, $OC_{1-4}$alkyl, or phenyl.

In one preferred embodiment is independently H, $C_{1-6}$alkyl, aryl, O-aryl.

In one preferred embodiment R11 is independently H, butyl, isopropyl, phenyl, phenoxy.

In one preferred embodiment R12 is independently H, halo, $C_{5-9}$heteroaryl, $C_{6-10}$carboaryl, wherein said heteroaryl and carboaryl are optionally substituted by 1 to 3 substituents independently selected from $NH_2$, $NMe_2$, SMe, methyl, ethyl, halo, OH, $OC_{1-4}$alkyl, or phenyl.

In one preferred embodiment R12 is independently H, halo, pyridyl, pyrimidyl, triazinyl, phenyl or purinyl wherein said heteroaryl and carboaryl are optionally substituted by 1 to 3 substituents independently selected from $NH_2$, $NMe_2$, SMe, methyl, ethyl, halo, OH, $OC_{1-4}$alkyl, or phenyl.

In one preferred embodiment R13 is independently H, $C_{1-6}$alkyl, aryl, O-aryl.

In one preferred embodiment R13 is independently H, butyl, isopropyl, phenyl, phenoxy.

In one preferred embodiment R9 is independently H, halo, $C_{1-6}$alkyl, $C_6$aryl;
R10 is independently H, halo, $C_{5-9}$heteroaryl, $C_{6-10}$carboaryl, wherein said heteroaryl and carboaryl are optionally substituted by 1 to 3 substituents independently selected from $NH_2$, $NMe_2$, SMe, methyl, ethyl, halo, OH, $OC_{1-4}$alkyl, or phenyl.
R11 is independently H, $C_{1-6}$alkyl, aryl, O-aryl.
R12 is independently H, halo, $C_{5-9}$heteroaryl, $C_{6-10}$carboaryl, wherein said heteroaryl and carboaryl are optionally substituted by 1 to 3 substituents independently selected from $NH_2$, $NMe_2$, SMe, methyl, ethyl, halo, OH, $OC_{1-4}$alkyl, or phenyl;
R13 is independently H, halo, $C_{1-6}$alkyl, $C_6$-aryl.

In one preferred embodiment,
R9 is independently H, F, Cl, isopropyl or phenyl;
R10 is independently H, halo, pyridyl, pyrimidyl, triazinyl, phenyl or purinyl wherein each heteroaryl and carboaryl are optionally substituted by 1 to 3 substituents independently selected from $NH_2$, $NMe_2$, methyl, ethyl, halo, OH, $OC_{1-4}$alkyl, or phenyl;
R11 is independently H, butyl, isopropyl, phenyl, phenoxy.
R12 is independently H, halo, pyridyl, pyrimidyl, triazinyl, phenyl or purinyl wherein each aryl are optionally substituted by 1 to 3 substituents independently selected from $NH_2$, $NMe_2$, methyl, ethyl, halo, OH, $OC_{1-4}$alkyl, or phenyl;
R13 is independently H, F, Cl, isopropyl or phenyl.

Stereochemistry

Many of the chemical structures shown herein indicate one or more specific stereoisomeric configurations. Similarly, many of the chemical structures shown herein are silent in this respect, and do not indicate any stereoisomeric configuration. Similarly, many of the chemical structures shown herein indicate the specific stereoisomeric configurations at one or more positions, but are silent with respect to one or more other positions. Where a chemical structure herein is silent with respect to the stereoisomeric configuration at a position, that structure is intended to depict all possible stereoisomeric configurations at that position, both individually, as if each possible stereoisomeric configuration was individually recited, and also as a mixture (e.g., a racemic mixture) of stereoisomers.

Combinations

Each and every compatible combination of the embodiments described above is explicitly disclosed herein, as if each and every combination was individually and explicitly recited.

Biological Activity

In one embodiment, the invention provides methods of treating or preventing of infections by by bacteria, fungi or parasites.

In one embodiment, the invention provides methods of treating or preventing a bacterial infection in a subject, such as a human or other animal subject, comprising administering an effective amount of an invention compound as disclosed herein to the subject.

In one embodiment, the compound is administered in a pharmaceutically acceptable form optionally in a pharmaceutically acceptable carrier. As used herein, an "infectious disorder" is any disorder characterized by the presence of a microbial infection, such as bacterial infections. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds of the invention may be used for the treatment or prevention of infectious disorders caused by a variety of bacterial organisms. Examples include Gram positive and Gram negative aerobic and anaerobic bacteria, including *Staphylococci*, for example *S. aureus*; *Enterococci*, for example *E. faecalis*; *Streptococci*, for example *S. pneumoniae*; *Haemophilus*, for example *H. influenza*; *Moraxella*, for example *M. catarrhalis*; and *Escherichia*, for example *E. coli*. Other examples include *Mycobacteria*, for example *M. tuberculosis*; intercellular microbes, for example *Chlamydia* and *Rickettsiae*; and *Mycoplasma*, for example *M. pneumoniae*.

In order to exhibit this antibacterial antifungal or antiparasitic activity, the compounds of Formula I need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 5000 mg/kg/day in single or in divided doses. Typically, dosages for humans will range from about 10 mg to about 3000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, epidural, and intraocular, intranasal, intraventricular injections or infusion techniques. Topical administrations include the treatment of areas readily accessible by local application, such as, for example, eyes, ears including external and middle ear infections, vaginal, open wound, skin including the surface skin and the dermal structures underneath, or lower intestinal tract. Transmucosal administration includes nasal aerosol or inhalation applications.

Formulations

Compounds of the invention can be formulated for administration in any way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, ophthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; nonaqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavouring or colouring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 100% by weight, of the active material, depending on the method of administration. Where the compositions comprise dosage units, each unit will contain, for example, from about 0.5-1000 mg of the active ingredient. If desired, the compounds of the invention may be administered in combination with one or more additional anti-bacterial agents ("the additional active agent"). Such use of compounds of the invention in combination with an additional active agent may be for simultaneous, separate or sequential use.

The Examples and preparations provided below further illustrate and exemplify the compounds of the present invention and methods of preparing such compounds. It is to be understood that the scope of the present invention is not limited in any way by the scope of the following Examples and preparations. In the following Examples, molecules with a single chiral centre, unless otherwise noted, exist as a racemic mixture. Those molecules with two or more chiral centres, unless otherwise noted, exist as a racemic mixture of diastereomers. Single enantiomers/diastereomers may be obtained by methods known to those skilled in the art.

EXAMPLES OF SPECIFIC EMBODIMENTS

The following examples further illustrate the invention, but should not be construed to limit the scope of the invention in any way.

The following N-acyl-arylsulfonamide derivatives 5.1-5.52 were prepared as examples of the current invention:

| ID | Cmpd. No | Structure |
|---|---|---|
| IK-698 | 5.1. | 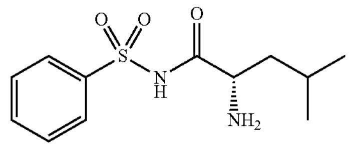 [SMILES: CC(C)C[C@H](N)C(=O)NS(=O)(=O)c1ccccc1] |
| IK-713 | 5.2. | 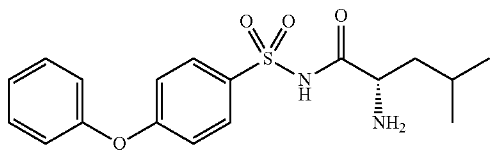 [SMILES: CC(C)C[C@H](N)C(=O)NS(=O)(=O)c1ccc(Oc2ccccc2)cc1] |
| IK-718 | 5.3. | 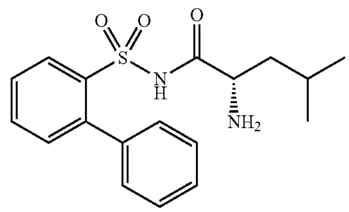 [SMILES: CC(C)C[C@H](N)C(=O)NS(=O)(=O)c1ccccc1-c1ccccc1] |
| LL-20 | 5.4. | 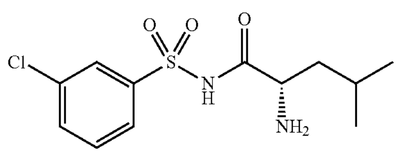 [SMILES: CC(C)C[C@H](N)C(=O)NS(=O)(=O)c1cccc(Cl)c1] |
| LL-19 | 5.5. | 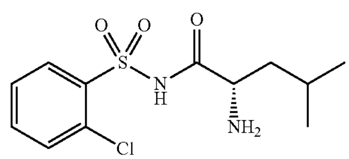 [SMILES: CC(C)C[C@H](N)C(=O)NS(=O)(=O)c1ccccc1Cl] |
| EO-99 | 5.6. | 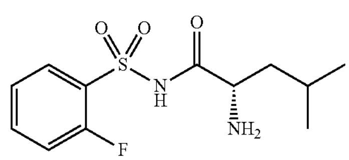 [SMILES: CC(C)C[C@H](N)C(=O)NS(=O)(=O)c1ccccc1F] |
| LL-23 | 5.7. | 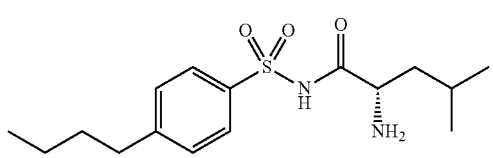 [SMILES: CCCCc1ccc(S(=O)(=O)NC(=O)[C@@H](N)CC(C)C)cc1] |
| MZ-377 | 5.8. | 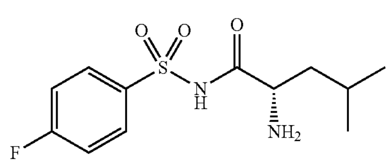 [SMILES: CC(C)C[C@H](N)C(=O)NS(=O)(=O)c1ccc(F)cc1] |
| IK-681 | 5.9. | 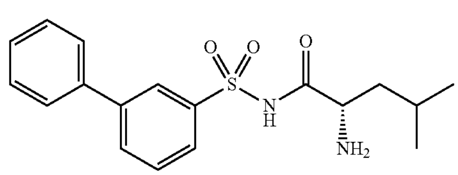 [SMILES: CC(C)C[C@H](N)C(=O)NS(=O)(=O)c1cccc(-c2ccccc2)c1] |

-continued

| ID | Cmpd. No | Structure |
|---|---|---|
| DL-23-340 | 5.10. | 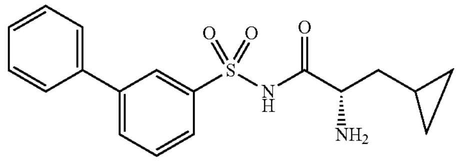 [SMILES: N[C@@H](CC1CC1)C(=O)NS(=O)(=O)c1cccc(-c2ccccc2)c1] |
| IK-707 | 5.11. | 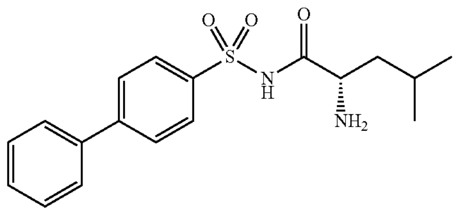 [SMILES: CC(C)C[C@H](N)C(=O)NS(=O)(=O)c1ccc(-c2ccccc2)cc1] |
| IK-719 | 5.12. | 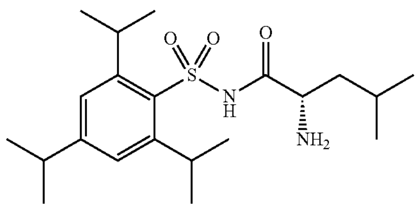 [SMILES: CC(C)C[C@H](N)C(=O)NS(=O)(=O)c1c(C(C)C)cc(C(C)C)cc1C(C)C] |
| IK-666 | 5.13. | 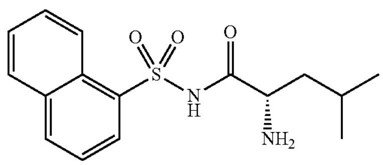 [SMILES: CC(C)C[C@H](N)C(=O)NS(=O)(=O)c1cccc2ccccc12] |
| IK-665 | 5.14. | 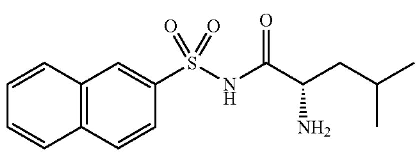 [SMILES: CC(C)C[C@H](N)C(=O)NS(=O)(=O)c1ccc2ccccc2c1] |
| DG-500 | 5.15. | 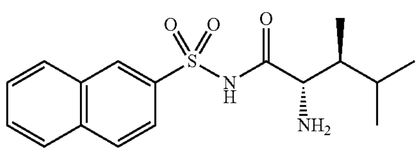 [SMILES: CC(C)[C@H](C)[C@H](N)C(=O)NS(=O)(=O)c1ccc2ccccc2c1] |
| MZ-335 | 5.16. | 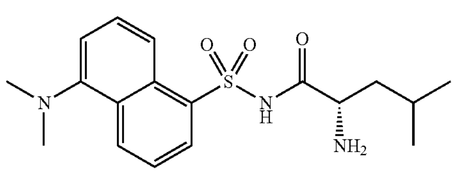 [SMILES: CC(C)C[C@H](N)C(=O)NS(=O)(=O)c1cccc2c(N(C)C)cccc12] |
| MZ-343 | 5.17. | 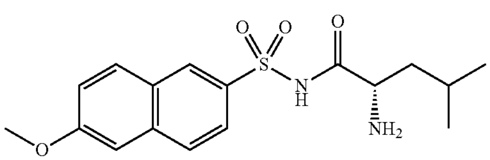 [SMILES: COc1ccc2cc(S(=O)(=O)NC(=O)[C@@H](N)CC(C)C)ccc2c1] |
| MZ-370 | 5.18. | 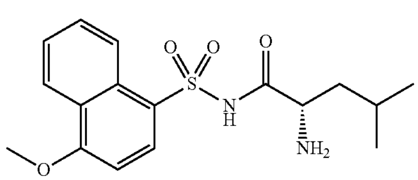 [SMILES: COc1ccc(S(=O)(=O)NC(=O)[C@@H](N)CC(C)C)c2ccccc12] |

-continued
| ID | Cmpd. No | Structure |
|---|---|---|
| KS-1189 | 5.19. | 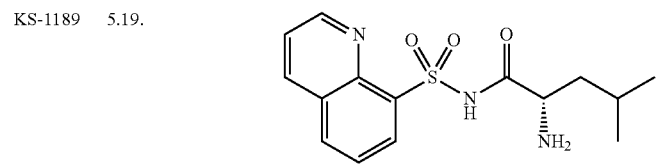 |
| MZ-375 | 5.20. | 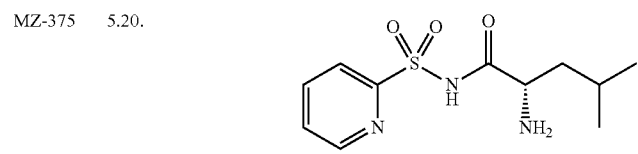 |
| C-2724 | 5.21. | 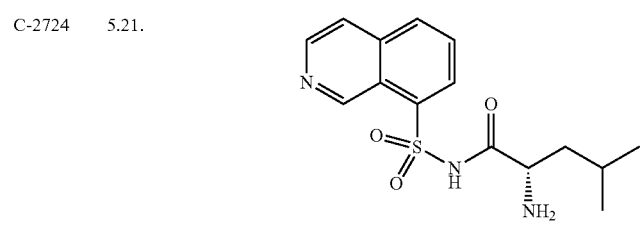 |
| C-2775 | 5.22. | 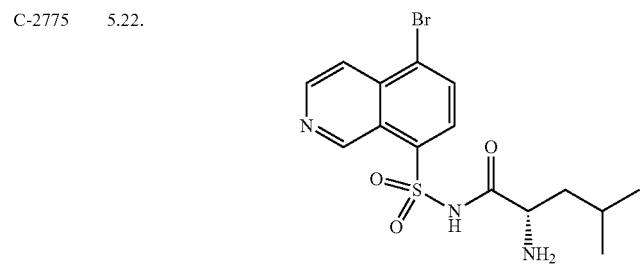 |
| MZ-368 | 5.23. | 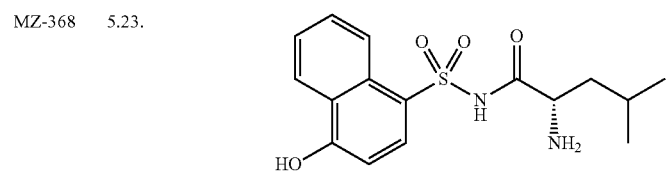 |
| IK-603 | 5.24. | 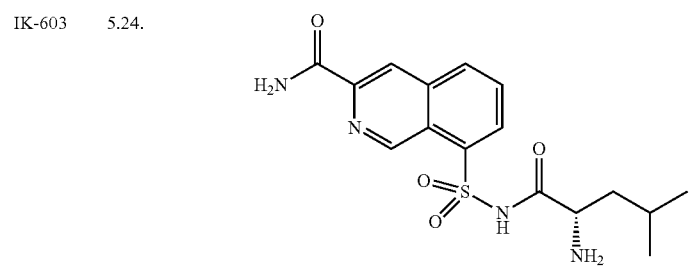 |
| AC-486 | 5.25. | 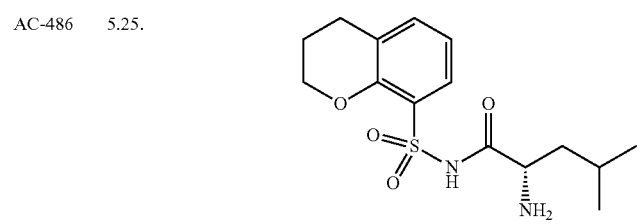 |

-continued

| ID | Cmpd. No | Structure |
|---|---|---|
| C-2727 | 5.26. | 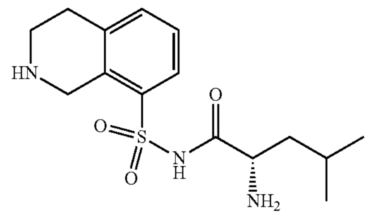 [SMILES: CC(C)C[C@H](N)C(=O)NS(=O)(=O)c1cccc2c1CNCC2] |
| DG-459 | 5.27. | 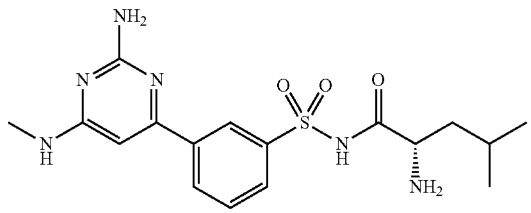 [SMILES: CNc1cc(-c2cccc(S(=O)(=O)NC(=O)[C@@H](N)CC(C)C)c2)nc(N)n1] |
| DG-457 | 5.28. | 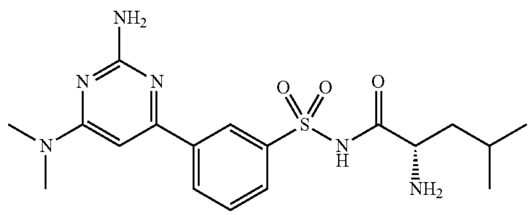 [SMILES: CC(C)C[C@H](N)C(=O)NS(=O)(=O)c1cccc(-c2cc(N(C)C)nc(N)n2)c1] |
| DG-460 | 5.29. | 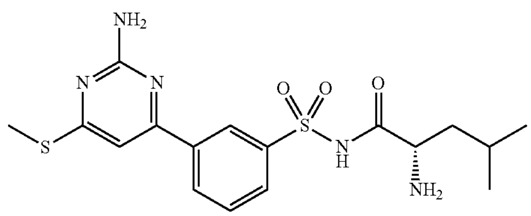 [SMILES: CSc1cc(-c2cccc(S(=O)(=O)NC(=O)[C@@H](N)CC(C)C)c2)nc(N)n1] |
| IK-656 | 5.30. | 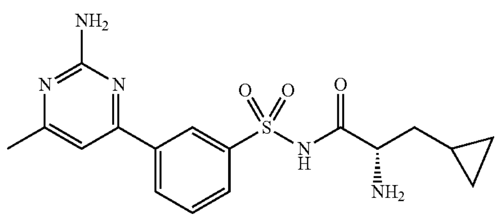 [SMILES: Cc1cc(-c2cccc(S(=O)(=O)NC(=O)[C@@H](N)CC3CC3)c2)nc(N)n1] |
| DG-466 | 5.31. | 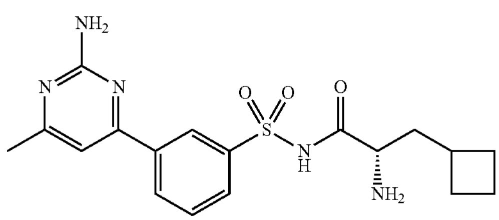 [SMILES: Cc1cc(-c2cccc(S(=O)(=O)NC(=O)[C@@H](N)CC3CCC3)c2)nc(N)n1] |
| DG-470 | 5.32. | 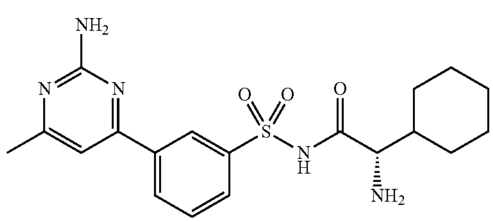 [SMILES: Cc1cc(-c2cccc(S(=O)(=O)NC(=O)[C@@H](N)C3CCCCC3)c2)nc(N)n1] |

-continued

| ID | Cmpd. No | Structure |
|---|---|---|
| IK-685 | 5.33. | 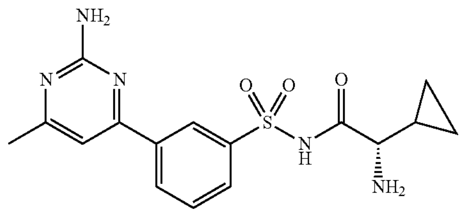 [SMILES: Cc1cc(-c2cccc(S(=O)(=O)NC(=O)[C@@H](N)C3CC3)c2)nc(N)n1] |
| DG-469 | 5.34. | 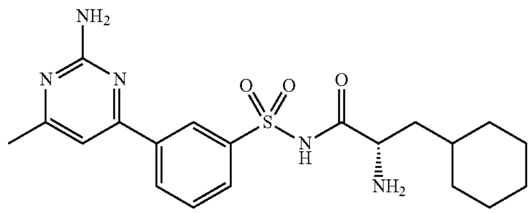 [SMILES: Cc1cc(-c2cccc(S(=O)(=O)NC(=O)[C@@H](N)CC3CCCCC3)c2)nc(N)n1] |
| IK-580 | 5.35. | 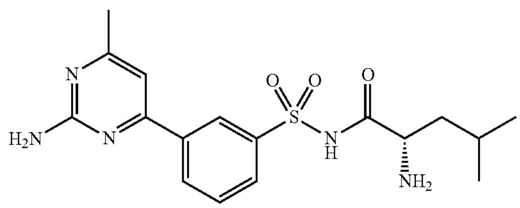 [SMILES: Cc1cc(-c2cccc(S(=O)(=O)NC(=O)[C@@H](N)CC(C)C)c2)nc(N)n1] |
| IK-617 | 5.36. | 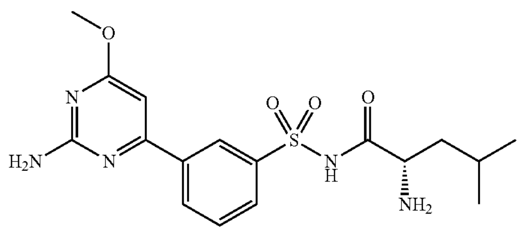 [SMILES: COc1cc(-c2cccc(S(=O)(=O)NC(=O)[C@@H](N)CC(C)C)c2)nc(N)n1] |
| IK-587 | 5.37. | 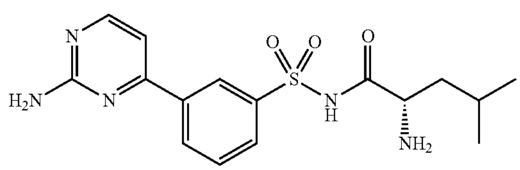 [SMILES: CC(C)C[C@H](N)C(=O)NS(=O)(=O)c1cccc(-c2ccnc(N)n2)c1] |
| K-615 | 5.38. | 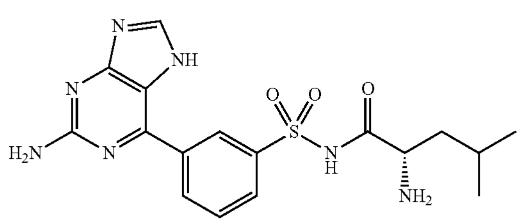 [SMILES: CC(C)C[C@H](N)C(=O)NS(=O)(=O)c1cccc(-c2nc(N)nc3nc[nH]c23)c1] |
| IK-621 | 5.39. | 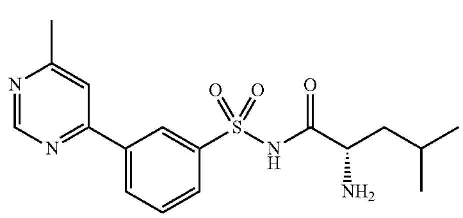 [SMILES: Cc1cc(-c2cccc(S(=O)(=O)NC(=O)[C@@H](N)CC(C)C)c2)ncn1] |

-continued

| ID | Cmpd. No | Structure |
|---|---|---|
| BM-13 | 5.40. | 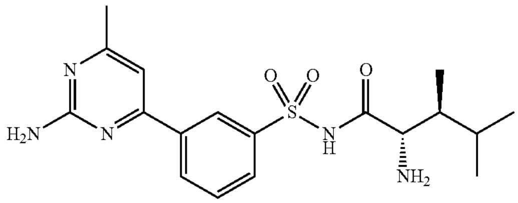 [SMILES: Cc1cc(-c2cccc(S(=O)(=O)NC(=O)[C@@H](N)[C@@H](C)C(C)C)c2)nc(N)n1] |
| IK-625, | 5.41. | 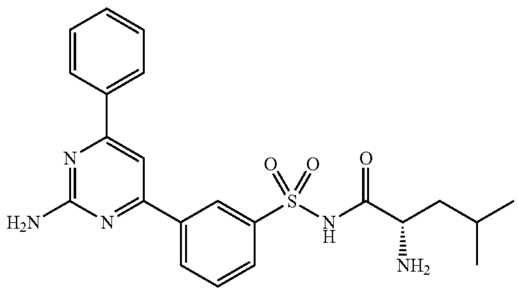 [SMILES: CC(C)C[C@H](N)C(=O)NS(=O)(=O)c1cccc(-c2cc(-c3ccccc3)nc(N)n2)c1] |
| IK-636 | 5.42. | 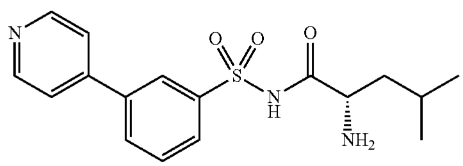 [SMILES: CC(C)C[C@H](N)C(=O)NS(=O)(=O)c1cccc(-c2ccncc2)c1] |
| IK-634 | 5.43. | 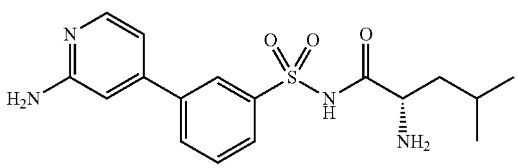 [SMILES: CC(C)C[C@H](N)C(=O)NS(=O)(=O)c1cccc(-c2ccnc(N)c2)c1] |
| IK-635 | 5.44. | 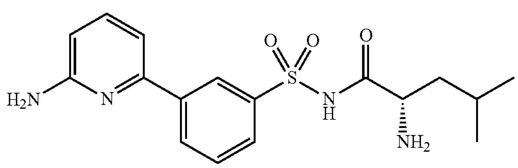 [SMILES: CC(C)C[C@H](N)C(=O)NS(=O)(=O)c1cccc(-c2cccc(N)n2)c1] |
| IK-627 | 5.45. | 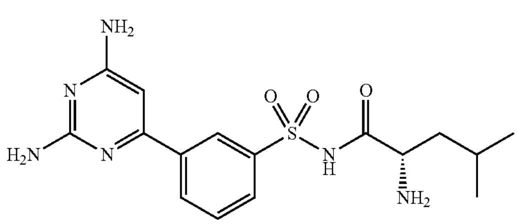 [SMILES: CC(C)C[C@H](N)C(=O)NS(=O)(=O)c1cccc(-c2cc(N)nc(N)n2)c1] |
| DG-435 | 5.46. | 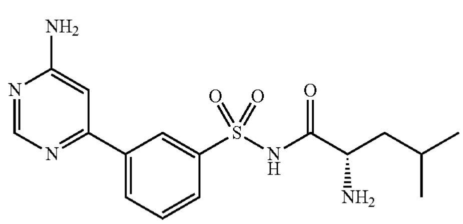 [SMILES: CC(C)C[C@H](N)C(=O)NS(=O)(=O)c1cccc(-c2cc(N)ncn2)c1] |

-continued
| ID | Cmpd. No | Structure |
|---|---|---|
| DG-437 | 5.47. | 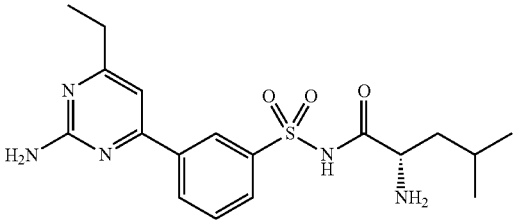 |
| DG-440 | 5.48. | 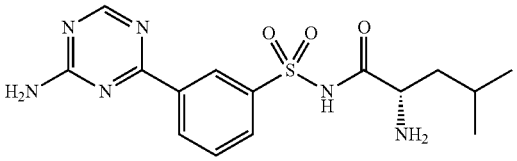 |
| DG-444 | 5.49. | 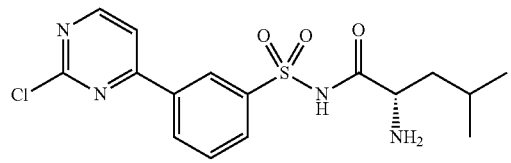 [SMILES: CC(C)C[C@H](N)C(=O)NS(=O)(=O)c1cccc(-c2ccnc(Cl)n2)c1] |
| DG-445 | 5.50. | 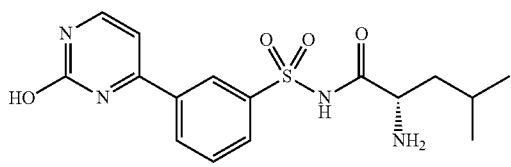 [SMILES: CC(C)C[C@H](N)C(=O)NS(=O)(=O)c1cccc(-c2ccnc(O)n2)c1] |
| DG-455 | 5.51. | 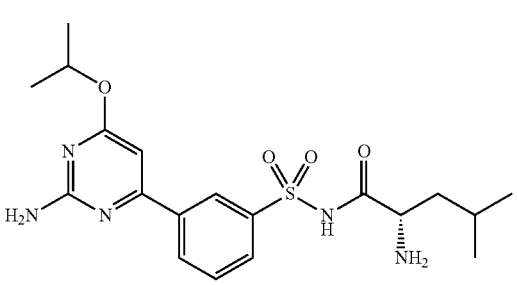 |
| DG-453 | 5.52. | 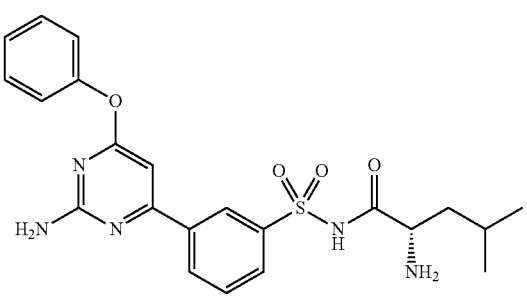 [SMILES: CC(C)C[C@H](N)C(=O)NS(=O)(=O)c1cccc(-c2cc(Oc3ccccc3)nc(N)n2)c1] |

General Synthesis

Compounds included as examples to the invention were prepared according to general Scheme 1. Sulfonyl chlorides 1 were transformed to sulfonamides 2 which were N-acylated with protected amino acids 3a-g to give N-acylsulfonamides 4. Deprotection provided final compounds 5.1-5.25, 5.27-5.52.

Scheme 1

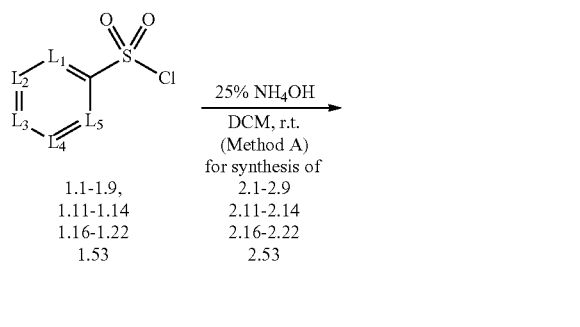

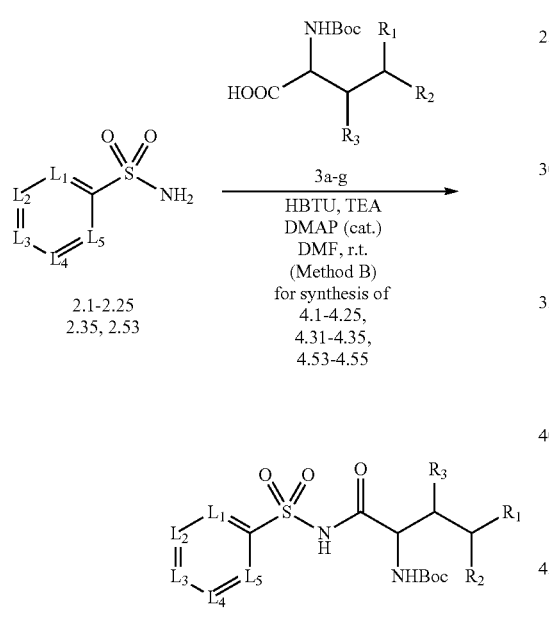

Several sulfonamides 2.23-2.25, 2.35 were prepared according to schemes 2-5.

Scheme 2

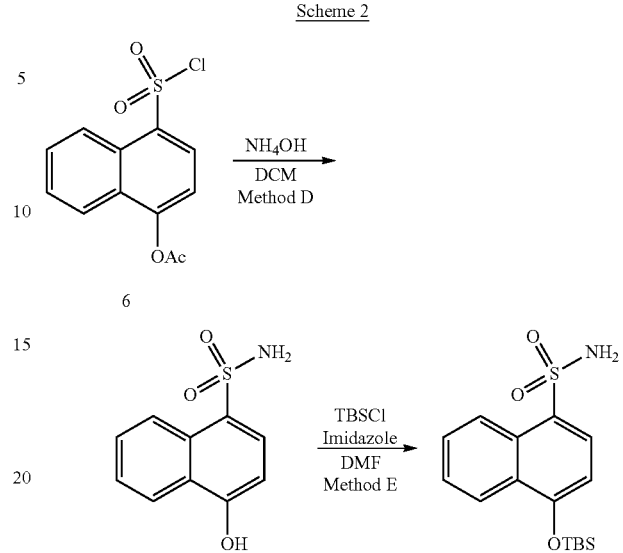

Scheme 3

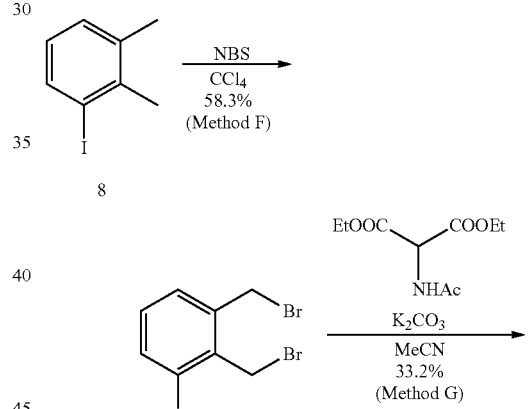

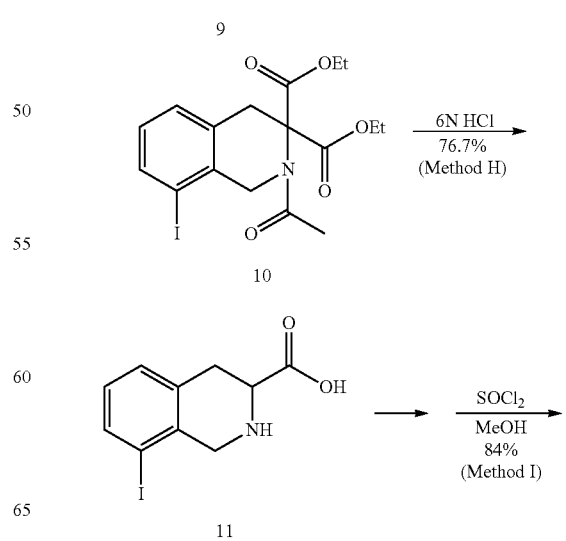

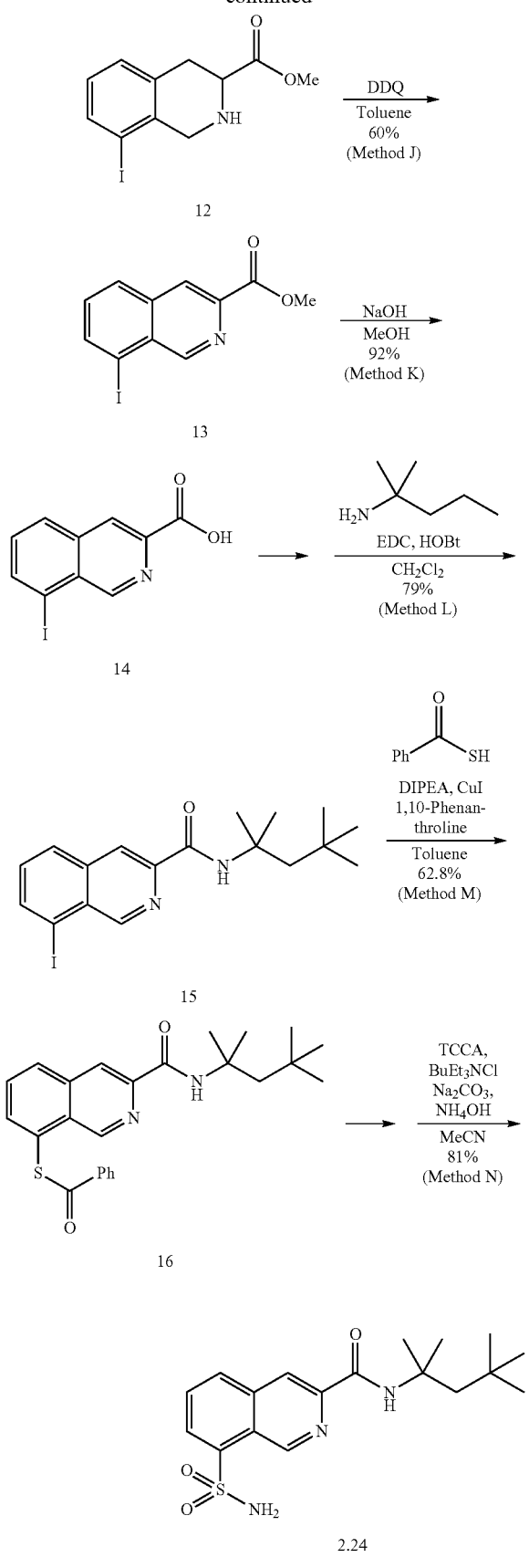
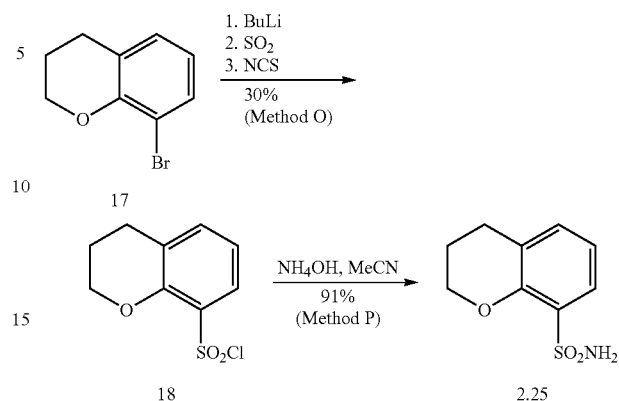
Several protected N-acyl sulphonamides were prepared from intermediates 4.53-4.55 by coupling these with pinacolate diborane to give boronic acid derivatives 20.27, 20.30, 20.40 which were then transferred to protected N-acyl sulphonamides 4.27-4.30, 4.35-4.49, 4.51, 4.52 according to Scheme 6.

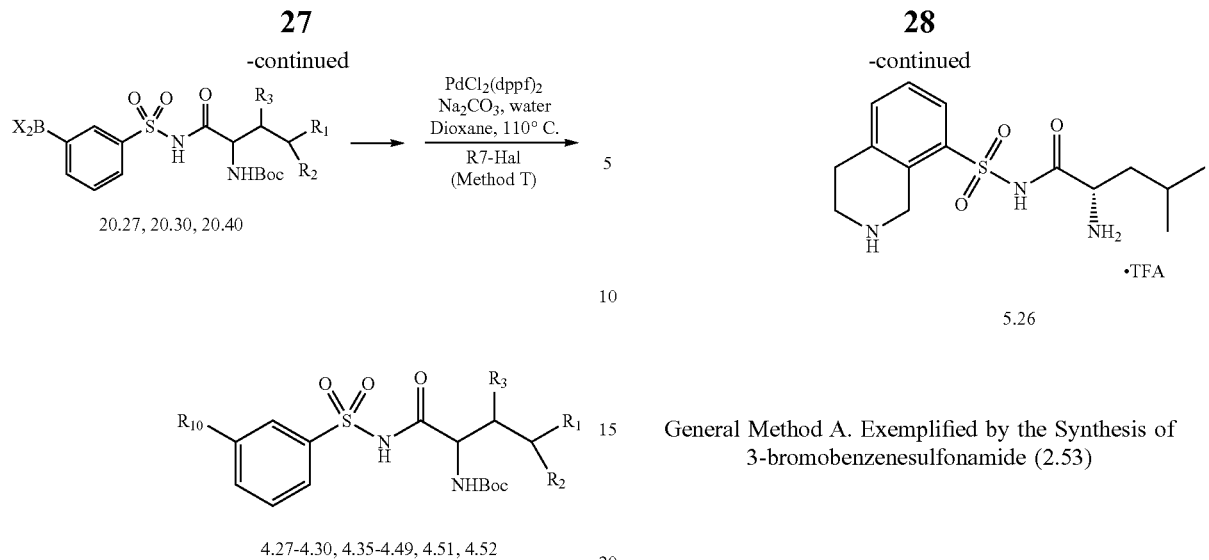

N-Acylsulfonamide 4.50 was prepared by hydrolytic replacement of chloride in the chloropyrimidine derivative 4.49 according to Scheme 7.

Scheme 7

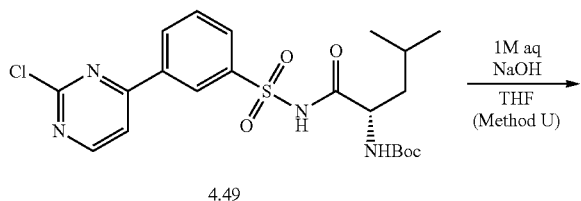

Acylsulfonamide 5.26 was prepared by partial hydrogenation of isoquinoline ring in compound 5.22 according to scheme 8.

Scheme 8

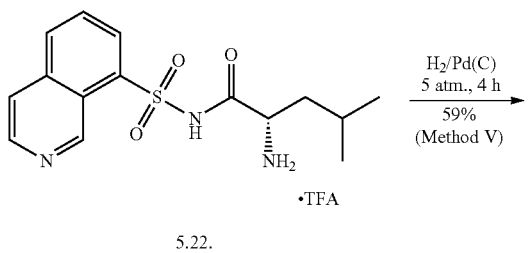

General Method A. Exemplified by the Synthesis of 3-bromobenzenesulfonamide (2.53)

To a solution of 3-bromobenzene-1-sulfonyl chloride (1.53) (4.073 g, 15.94 mmol) in DCM (67 ml) at ice bath temperature was added 25% NH$_4$OH solution in water (3.7 ml, 57.15 mmol). The reaction mixture was stirred at this temperature for 0.5 h followed by stirring for 6 h at room temperature. The precipitated solid material was filtered, washed with water, and dried in vacuo over P$_2$O$_5$ to give 3-bromobenzene-sulfonamide (2.53) (3.270 g, 87%) as white crystals. $^1$H NMR (DMSO-d$_6$) δ: 7.97 (t, J=1.9 Hz, 1H), 7.84-7.80 (m, 2H), 7.54 (t, J=7.9 Hz, 1H), 7.50 (b s, 2H). LCMS (ESI) m/z: 235.98 [M–H]$^-$.

By a method analogous to Method A, the following compounds were obtained:

| Compound No | Procedure | Precursor | Structure |
|---|---|---|---|
| 2.1 | A | 1.1 | (benzenesulfonamide) |
| 2.2. | A | 1.2 | (4-PhO-benzenesulfonamide) |
| 2.3. | A | 1.3 | (2-Ph-benzenesulfonamide) |

-continued

| Compound No | Procedure | Precursor | Structure |
|---|---|---|---|
| 2.4. | A | 1.4 | 3-chlorobenzenesulfonamide |
| 2.5. | A | 1.5 | 2-chlorobenzenesulfonamide |
| 2.6 | A | 1.6 | 2-fluorobenzenesulfonamide |
| 2.7 | A | 1.7 | 4-n-butylbenzenesulfonamide |
| 2.8 | A | 1.8 | 4-fluorobenzenesulfonamide |
| 2.9 | A | 1.9 | 3-phenylbenzenesulfonamide |
| 2.11 | A | 1.11 | 4-phenylbenzenesulfonamide |
| 2.12 | A | 1.12 | 2,4,6-triisopropylbenzenesulfonamide |
| 2.13 | A | 1.13 | naphthalene-1-sulfonamide |

-continued

| Compound No | Procedure | Precursor | Structure |
|---|---|---|---|
| 2.14 | A | 1.14 | naphthalene-2-sulfonamide |
| 2.16 | A | 1.16 | 8-(dimethylamino)naphthalene-1-sulfonamide |
| 2.17 | A | 1.17 | 6-methoxynaphthalene-2-sulfonamide |
| 2.18 | A | 1.18 | 4-methoxynaphthalene-1-sulfonamide |
| 2.19 | A | 1.19 | quinoline-8-sulfonamide |
| 2.20 | A | 1.20 | pyridine-2-sulfonamide |
| 2.21 | A | 1.21 | isoquinoline-8-sulfonamide |
| 2.22 | A | 1.22 | 5-bromoisoquinoline-8-sulfonamide |
| 2.53 | A | 1.53 | 3-bromobenzenesulfonamide |

General Method B. Exemplified by the Synthesis of (S)-tert-butyl (1-(3-bromophenylsulfonamido)-4-methyl-1-oxopentan-2-yl)carbamate (4.53)

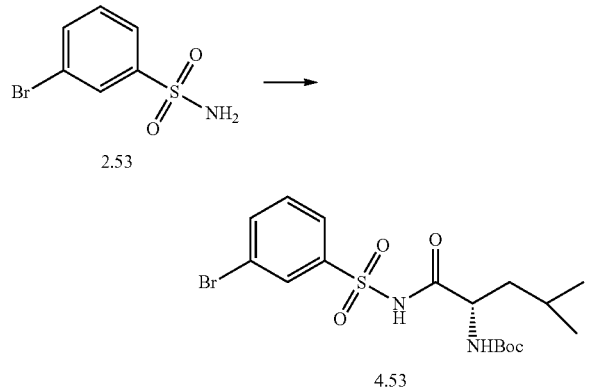

To a solution of BOC-L-leucine monohydrate 3a (0.592 g, 2.37 mmol) in DMF (5 ml) successively were added 3-bromobenzenesulfonamide 2.53 (0.561 g, 2.37 mmol), HBTU (0.900 g, 2.37 mmol), TEA (0.66 ml, 4.75 mmol), and a catalytic amount of DMAP (0.029 g, 0.237 mmol). The reaction mixture was stirred for 24 h and poured into water (70 ml). The mixture was extracted with EtOAc (3×75 ml), the combined organic extracts were washed with 1N HCl (20 ml), water (2×100 ml), saturated solution of NaCl (100 ml), and dried ($Na_2SO_4$). The volatiles were evaporated and the residue (0.988 g) was purified by Biotage purification system (C18HS 40+M column, eluent water-methanol, gradient from 1:1 to 0:100) to afford 0.660 g (61.8%) of (S)-tert-butyl (1-(3-bromophenylsulfonamido)-4-methyl-1-oxopentan-2-yl)carbamate (4.53) as a foam. $^1$H NMR ($CDCl_3$) δ: 9.57 (b s, 1H), 8.16 (t, J=1.8 z, 1H), 8.00 (d, J=7.9 Hz, 1H), 7.75 (ddd, J=7.9, 1.8, 1.0 Hz, 1H), 7.40 (t, J=7.9 Hz, 1H), 4.70 (unresolved d, J=6.4 Hz, 1H), 4.06-3.92 (m, 1H), 1.70-1.52 (m, 3H), 1.44 (s, 9H), 0.91 (d, J=6.3 Hz, 3H), 0.87 (d, J=6.3 Hz, 3H). LCMS (ESI) m/z: 449.2 [M−H]$^-$.

Following a method analogous to Method B, the following compounds were obtained:

| Compound No | Method | Precursor | Structure |
|---|---|---|---|
| 4.1 | B | 2.1 | 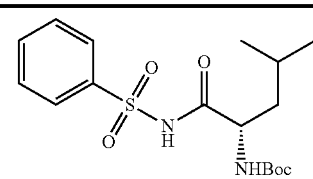 |
| 4.2 | B | 2.2 | 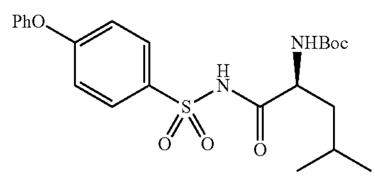 [SMILES: CC(C)C[C@H](NC(=O)OC(C)(C)C)C(=O)NS(=O)(=O)c1ccc(Oc2ccccc2)cc1] |
| 4.3 | B | 2.3 | 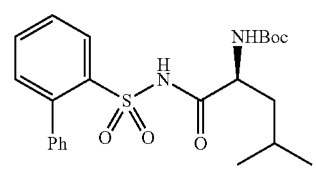 [SMILES: CC(C)C[C@H](NC(=O)OC(C)(C)C)C(=O)NS(=O)(=O)c1ccccc1-c1ccccc1] |
| 4.4 | B | 2.4 | 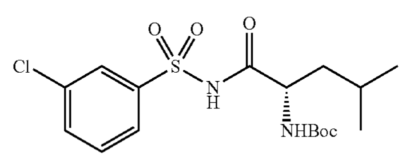 [SMILES: CC(C)C[C@H](NC(=O)OC(C)(C)C)C(=O)NS(=O)(=O)c1cccc(Cl)c1] |
| 4.5 | B | 2.5 | 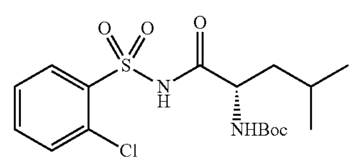 [SMILES: CC(C)C[C@H](NC(=O)OC(C)(C)C)C(=O)NS(=O)(=O)c1ccccc1Cl] |
| 4.6 | B | 2.6 | 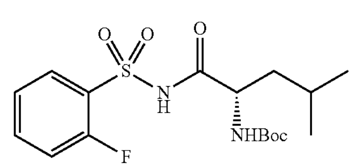 [SMILES: CC(C)C[C@H](NC(=O)OC(C)(C)C)C(=O)NS(=O)(=O)c1ccccc1F] |

-continued

| Compound No | Method | Precursor | Structure |
|---|---|---|---|
| 4.7 | B | 2.7 | *4-nBu-C6H4-SO2-NH-C(=O)-CH(NHBoc)-CH2-CH(CH3)2* |
| 4.8 | B | 2.8 | *4-F-C6H4-SO2-NH-C(=O)-CH(NHBoc)-CH2-CH(CH3)2* |
| 4.9 | B | 2.9 | *3-biphenyl-SO2-NH-C(=O)-CH(NHBoc)-CH2-CH(CH3)2* |
| 4.10 | B | 2.9 | *3-biphenyl-SO2-NH-C(=O)-CH(NHBoc)-CH2-cyclopropyl* |
| 4.11 | B | 2.11 | *4-biphenyl-SO2-NH-C(=O)-CH(NHBoc)-CH2-CH(CH3)2* |
| 4.12 | B | 2.12 | *2,4,6-triisopropyl-C6H2-SO2-NH-C(=O)-CH(NHBoc)-CH2-CH(CH3)2* |
| 4.13 | B | 2.13 | *naphthalen-1-yl-SO2-NH-C(=O)-CH(NHBoc)-CH2-CH(CH3)2* |
| 4.14 | B | 2.14 | *naphthalen-2-yl-SO2-NH-C(=O)-CH(NHBoc)-CH2-CH(CH3)2* |

-continued

| Compound No | Method | Precursor | Structure |
|---|---|---|---|
| 4.15 | B | 2.14 | naphthalene-2-sulfonyl-NH-C(=O)-CH(NHBoc)-CH(CH₃)-CH₂CH₃ |
| 4.16 | B | 2.16 | 5-(dimethylamino)naphthalene-1-sulfonyl-NH-C(=O)-CH(NHBoc)-CH₂CH(CH₃)₂ |
| 4.17 | B | 2.17 | 6-methoxynaphthalene-2-sulfonyl-NH-C(=O)-CH(NHBoc)-CH₂CH(CH₃)₂ |
| 4.18 | B | 2.18 | 4-methoxynaphthalene-1-sulfonyl-NH-C(=O)-CH(NHBoc)-CH₂CH(CH₃)₂ |
| 4.19 | B | 2.19 | quinoline-8-sulfonyl-NH-C(=O)-CH(NHBoc)-CH₂CH(CH₃)₂ |
| 4.20 | B | 2.20 | pyridine-2-sulfonyl-NH-C(=O)-CH(NHBoc)-CH₂CH(CH₃)₂ |
| 4.21 | B | 2.21 | isoquinoline-8-sulfonyl-NH-C(=O)-CH(NHBoc)-CH₂CH(CH₃)₂ |
| 4.22 | B | 2.22 | 5-bromoisoquinoline-8-sulfonyl-NH-C(=O)-CH(NHBoc)-CH₂CH(CH₃)₂ |

| Compound No | Method | Precursor | Structure |
|---|---|---|---|
| 4.23 | B | 2.23 | 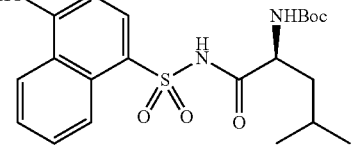 |
| 4.24 | B | 2.24 | 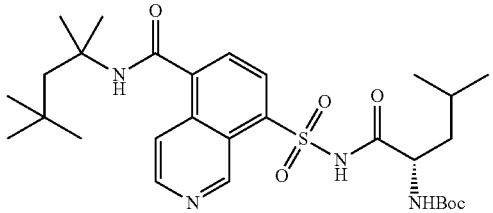 [SMILES: CC(C)C[C@H](NC(=O)OC(C)(C)C)C(=O)NS(=O)(=O)c1ccc(C(=O)NC(C)(C)CC(C)(C)C)c2ccncc12] |
| 4.25 | B | 2.25 | 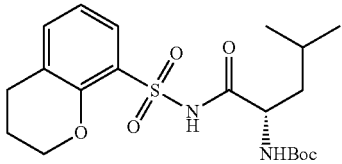 [SMILES: CC(C)C[C@H](NC(=O)OC(C)(C)C)C(=O)NS(=O)(=O)c1cccc2c1OCCC2] |
| 4.31 | B | 2.35 | 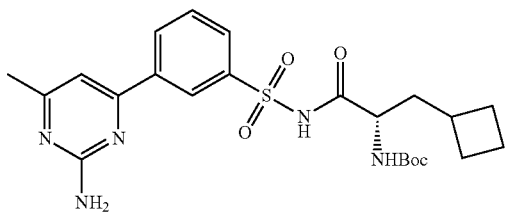 [SMILES: Cc1cc(-c2cccc(S(=O)(=O)NC(=O)[C@H](CC3CCC3)NC(=O)OC(C)(C)C)c2)nc(N)n1] |
| 4.32 | B | 2.35 | 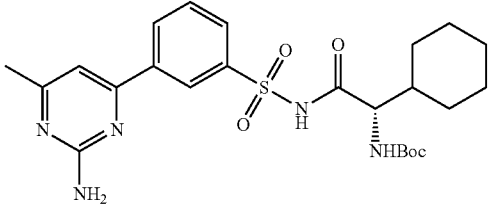 [SMILES: Cc1cc(-c2cccc(S(=O)(=O)NC(=O)[C@@H](NC(=O)OC(C)(C)C)C3CCCCC3)c2)nc(N)n1] |
| 4.33 | B | 2.35 | 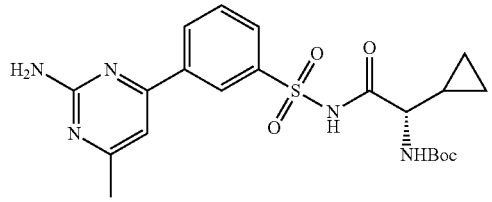 |
| 4.34 | B | 2.35 | 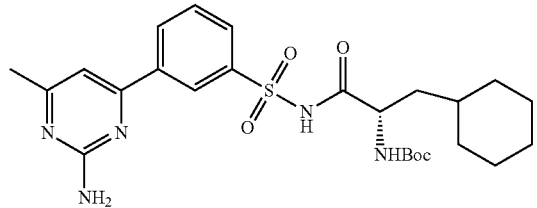 [SMILES: Cc1cc(-c2cccc(S(=O)(=O)NC(=O)[C@H](CC3CCCCC3)NC(=O)OC(C)(C)C)c2)nc(N)n1] |

-continued

| Compound No | Method | Precursor | Structure |
|---|---|---|---|
| 4.35 | B | 2.35 | 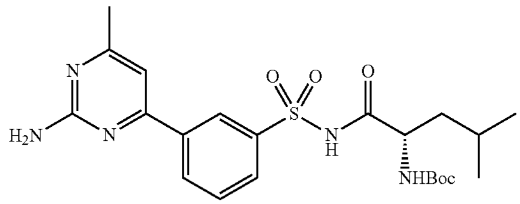 [SMILES: Cc1cc(-c2cccc(S(=O)(=O)NC(=O)[C@H](CC(C)C)NC(=O)OC(C)(C)C)c2)nc(N)n1] |
| 4.53 | B | 2.53 | 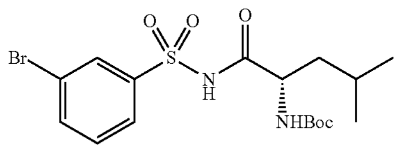 [SMILES: CC(C)C[C@H](NC(=O)OC(C)(C)C)C(=O)NS(=O)(=O)c1cccc(Br)c1] |
| 4.54 | B | 2.53 | 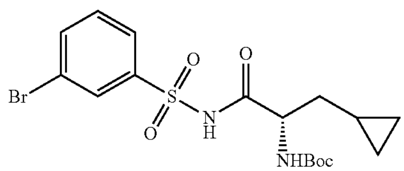 [SMILES: CC(C)(C)OC(=O)N[C@@H](CC1CC1)C(=O)NS(=O)(=O)c1cccc(Br)c1] |
| 4.55 | B | 2.53 | 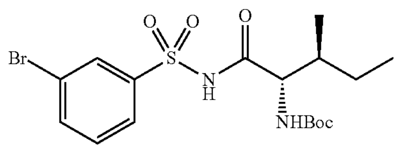 [SMILES: CC[C@H](C)[C@H](NC(=O)OC(C)(C)C)C(=O)NS(=O)(=O)c1cccc(Br)c1] |

General Method C1. Exemplified by the Synthesis of (S)-2-amino-N-((3-(2-amino-6-methylpyrimidin-4-yl)phenyl)sulfonyl)-4-methylpentanamide (5.35)

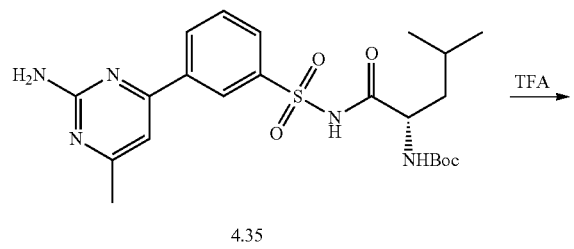

4.35

TFA

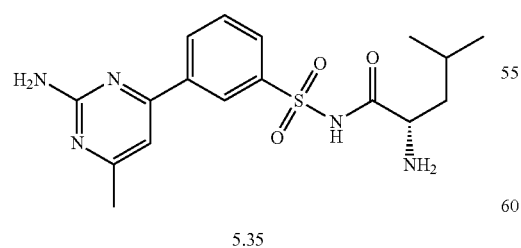

5.35

(S)-tert-Butyl (1-(3-(2-amino-6-methylpyrimidin-4-yl)phenylsulfonamido)-4-methyl-1-oxopentan-2-yl)carbamate (4.35) (0.246 g, 0.515 mmol) was dissolved in a 5% TFA solution in dichloromethane (12 ml) and the obtained solution was stirred at room temperature for 2 h. The reaction mixture was concentrated in vacuo and the oily brown residue (0.396 g) was purified by Biotage purification system (C18HS 40+M column, eluent water-acetonitrile, gradient from 95:5 to 60:40) to afford 0.162 g (83%) of (5)-2-amino-N-((3-(2-amino-6-methylpyrimidin-4-yl)phenyl)sulfonyl)-4-methylpentanamide (5.35) as white crystals, m.p. 241-242° C. (dec.). (DMSO-$d_6$, HMDSO) δ: 8.50 (t, J=1.7 Hz, 1H), 8.05 (ddd, J=7.8, 1.7, 1.2 Hz, 1H), 7.88 (ddd, J=7.8, 1.7, 1.2 Hz, 1H), 7.67 (b s, 3H), 7.50 (t, J=7.8 Hz, 1H), 7.01 (s, 1H), 6.63 (s, 2H), 3.37-3.30 (m, 1H, overlapped with water), 2.31 (s, 3H), 1.73-1.60 (m, 1H), 1.58 (ddd, J=13.7, 8.4, 5.6 Hz, 1H), 1.38 (ddd, J=13.7, 8.3, 5.8 Hz, 1H), 0.83 (d, J=6.3 Hz, 3H), 0.81 (d, J=6.3 Hz, 3H). LCMS (ESI) m/z: 378.2 [M+H]$^+$. Anal. Calcd for $C_{17}H_{23}N_5O_3S \times 0.09$ $CF_3COOH$ (2.5%)×1.12$H_2O$ (4.9%): C, 50.59, H, 6.26, N, 17.17. Found: C, 50.59, H, 6.32, N, 17.23.

General Method C2. Exemplified by the Synthesis of (S)-2-amino-4-methyl-N-(phenylsulfonyl)pentanamide hydrochloride (5.1)

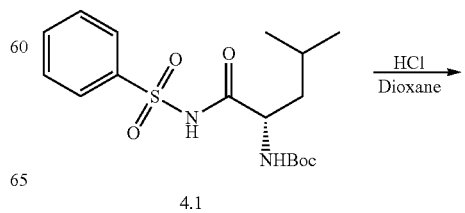

4.1

HCl / Dioxane

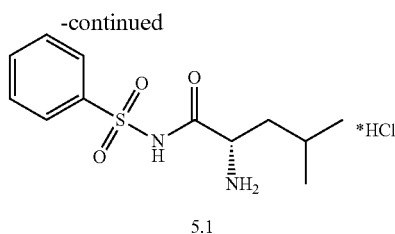

5.1

To a solution tert-butyl (S)-(4-methyl-1-oxo-1-(phenylsulfonamido)pentan-2-yl)carbamate (4.1) (0.160 g, 0.43 mmol) in dioxane (5 mL) under argon 4N HCl dioxane solution (2.5 mL) was added dropwise and the resulting mixture was stirred at room temperature overnight. The reaction mixture was concentrated in vacuo and the residue was triturated with diethyl ether (4×5 mL). The solid material was filtered, washed with diethyl ether (5 mL) and dried in vacuo over $P_2O_5$ to give 0.076 g (57%) of compound (5.1) as white crystals, mp 192° C. $^1$H NMR (DMSO-$d_6$) δ: 13.05 (b s, 1H), 8.43 (b s, 3H), 7.98-7.94 (m, 2H), 7.76-7.70 (m, 1H), 7.67-7.61 (m, 2H), 3.93-3.83 (m, 1H), 1.67-1.48 (m, 3H), 0.82 (d, J=6.0 Hz, 3H), 0.81 (d, J=6.1 Hz, 3H). $^{13}$C NMR (DMSO-$d_6$) δ: 169.1, 138.9, 133.9, 129.2, 127.6, 51.3, 23.4, 22.6, 21.7. LCMS (ESI) m/z: 271.2 [M+H]$^+$. Anal. Calcd for $C_{12}H_{18}N_2O_3S×HCl$ (11.8%)×0.06$H_2O$ (0.4%): C, 46.81, H, 6.26, N, 9.10. Found: C, 46.81, H, 6.21, N, 9.02.

General Method C3. Exemplified by the Synthesis (S)-2-amino-N-((5-(dimethylamino)naphthalen-1-yl)sulfonyl)-4-methylpentanamide hydrochloride (5.16)

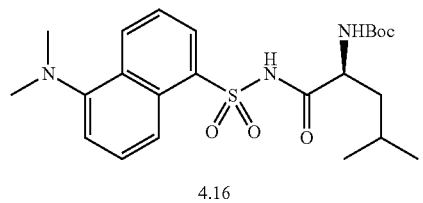

4.16

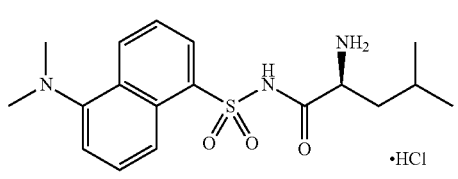

5.16 tert-Butyl (S)-(1-((5-(dimethylamino)naphthalene)-1-sulfonamido)-4-methyl-1-oxopentan-2-yl)carbamate (4.16) (0.155 g, 0.33 mmol) was dissolved in dioxane (6.5 mL). The solution was cooled to 0-5° C. and 4N HCl solution in dioxane (1.95 mL) was added dropwise. The solution was stirred at room temperature for 16 h. The reaction mixture was concentrated in vacuo and the residue was purified by Biotage purification system (C18HS 40+M column, eluent water-acetonitrile, gradient from 100:0 to 50:50) to afford 0.099 g of compound 5.16 (77%) as white powder, mp 178-180° C. $^1$H NMR (DMSO-$d_6$) δ: 8.65 (d, J=8.3 Hz, 1H), 8.40-8.32 (m, 2H), 8.29 (b s, 3H), 7.74 (t, J=8.0 Hz, 1H), 7.71 (t, J=8.1 Hz, 1H), 7.45 (d, J=7.5 Hz, 1H), 3.82 (m, overlapped with water, 1H), 2.92 (s, 6H), 1.46-1.25 (m, 3H), 0.70 (d, J=5.8 Hz, 3H), 0.65 (d, J=5.8 Hz, 3H). $^{13}$C NMR (DMSO-$d_6$) δ: 168.9, 154.8, 143.8, 133.9, 131.6, 130.5, 128.7, 128.4, 127.9, 124.3, 117.1, 51.3, 45.5, 23.2, 22.5, 21.6. LCMS (ESI) m/z: 364.3 [M+H]$^+$. Anal. Calcd for $C_{18}H_{25}N_3O_3S×2.9$ HCl (21.9%)×0.75$H_2O$ (2.8%): C, 44.79, H, 6.14, N, 8.70. Found: C, 44.77, H, 6.14, N, 8.47.

General Method C4. Exemplified by the Synthesis of 8-(N-(L-Leucyl)sulfamoyl)isoquinoline-3-carboxamide (5.24)

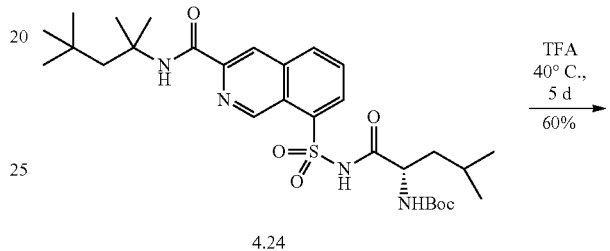

4.24

$\xrightarrow{\text{TFA} \atop 40°\text{C.,} \atop 5\text{ d} \atop 60\%}$

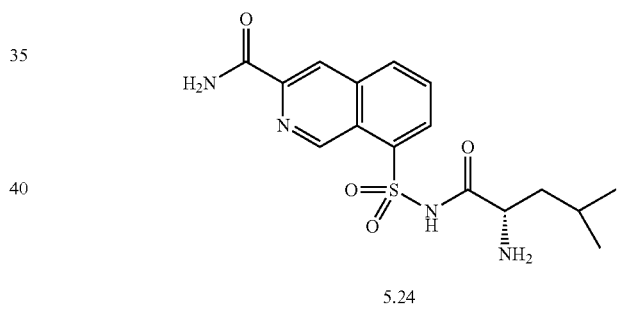

5.24 tert-Butyl (S)-(4-methyl-1-oxo-1-((3-((2,4,4-trimethylpentan-2-yl)carbamoyl)isoquinoline)-8-sulfonamido)pentan-2-yl)carbamate (4.24) (0.042 g, 0.073 mmol) was dissolved in TFA (2 mL) and the obtained solution was stirred at 40° C. for 5 days. The reaction mixture was concentrated in vacuo and the oily brown residue was purified by Biotage purification system (C18HS 40+M column, eluent water-acetonitrile, gradient from 95:5 to 80:20) to afford 0.016 g (60%) of compound (5.24) as white crystals, m.p. 222.9° C. (detection by OptiMelt). $^1$H NMR (DMSO-$d_6$) δ: 10.11 (s, 1H), 8.56 (s, 1H), 8.27 (d, J=2.0 Hz, 1H), 8.24 (d, J=7.3 Hz, 1H), 8.24 (d, J=8.3 Hz, 1H), 7.87 (t, J=7.8 Hz, 1H), 7.76 (d, J=2.0 Hz, 1H), 7.63 (b s, 3H), 3.31 (dd, J=7.7, 5.6 Hz, 1H), 1.52-1.44 (m, 2H), 1.26-1.19 (m, 1H), 0.74 (d, J=5.9 Hz, 3H), 0.71 (d, J=5.9 Hz, 3H). $^{13}$C NMR (DMSO-$d_6$) δ: 173.2, 166.2, 150.4, 143.8, 142.3, 136.0, 131.1, 130.0, 129.7, 124.5, 119.8, 53.4, 40.6, 23.7, 22.5, 21.8. LCMS (ESI) m/z: 365.2 [M+H]$^+$. Anal. Calcd for $C_{16}H_{20}N_4O_4S×0.08$ $CF_3COOH$ (2.3%)×1.1$H_2O$ (5.0%): C, 49.34, H, 5.71, N, 14.24, S, 8.15. Found: C, 49.34, H, 5.77, N, 14.16, S, 7.92.

Following a method analogous to Method C, the following compounds were obtained:

| Compound No | Procedure | Precursor | Structure |
|---|---|---|---|
| 5.1 | C2 | 4.1 | phenylsulfonyl-NH-C(=O)-CH(NH₂)-CH₂-CH(CH₃)₂ |
| 5.2 | C2 | 4.2 | 4-PhO-C₆H₄-SO₂-NH-C(=O)-CH(NH₂)-CH₂-CH(CH₃)₂ |
| 5.3 | C2 | 4.3 | 2-Ph-C₆H₄-SO₂-NH-C(=O)-CH(NH₂)-CH₂-CH(CH₃)₂ |
| 5.4 | C2 | 4.4 | 3-Cl-C₆H₄-SO₂-NH-C(=O)-CH(NH₂)-CH₂-CH(CH₃)₂ |
| 5.5 | C2 | 4.5 | 2-Cl-C₆H₄-SO₂-NH-C(=O)-CH(NH₂)-CH₂-CH(CH₃)₂ |
| 5.6 | C2 | 4.6 | 2-F-C₆H₄-SO₂-NH-C(=O)-CH(NH₂)-CH₂-CH(CH₃)₂ |
| 5.7 | C2 | 4.7 | 4-nBu-C₆H₄-SO₂-NH-C(=O)-CH(NH₂)-CH₂-CH(CH₃)₂ |
| 5.8 | C3 | 4.8 | 4-F-C₆H₄-SO₂-NH-C(=O)-CH(NH₂)-CH₂-CH(CH₃)₂ |
| 5.9 | C2 | 4.9 | 3-Ph-C₆H₄-SO₂-NH-C(=O)-CH(NH₂)-CH₂-CH(CH₃)₂ |

-continued
| Compound No | Procedure | Precursor | Structure |
|---|---|---|---|
| 5.10 | C2 | 4.10 | 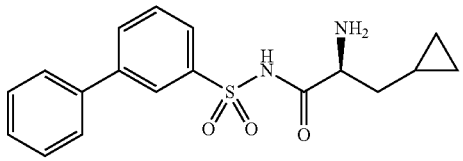 [SMILES: N[C@@H](CC1CC1)C(=O)NS(=O)(=O)c1cccc(-c2ccccc2)c1] |
| 5.11 | C2 | 4.11 | 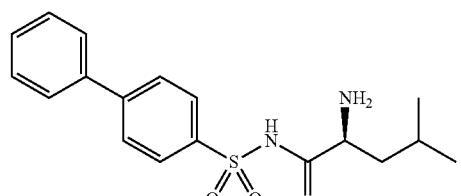 |
| 5.12 | C2 | 4.12 | 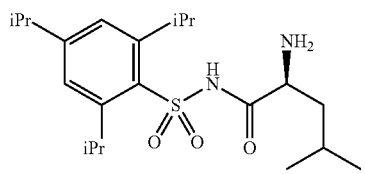 [SMILES: CC(C)C[C@H](N)C(=O)NS(=O)(=O)c1c(C(C)C)cc(C(C)C)cc1C(C)C] |
| 5.13 | C2 | 4.13 | 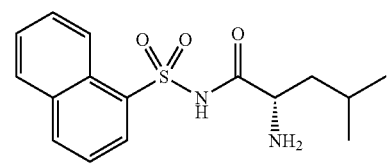 [SMILES: CC(C)C[C@H](N)C(=O)NS(=O)(=O)c1cccc2ccccc12] |
| 5.14 | C2 | 4.14 | 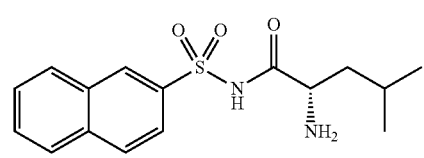 [SMILES: CC(C)C[C@H](N)C(=O)NS(=O)(=O)c1ccc2ccccc2c1] |
| 5.15 | C2 | 4.15 | 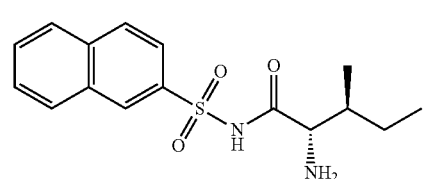 |
| 5.16 | C3 | 4.16 | 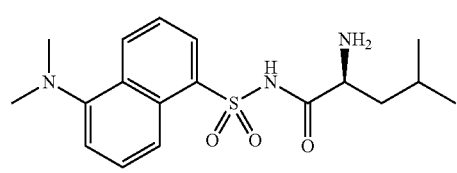 [SMILES: CC(C)C[C@H](N)C(=O)NS(=O)(=O)c1cccc2c(N(C)C)cccc12] |
| 5.17 | C3 | 4.17 | 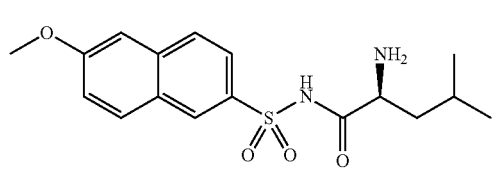 [SMILES: COc1ccc2cc(S(=O)(=O)NC(=O)[C@@H](N)CC(C)C)ccc2c1] |

-continued
| Compound No | Procedure | Precursor | Structure |
|---|---|---|---|
| 5.18 | C3 | 4.18 | 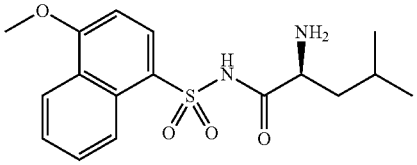 [SMILES: COc1ccc(S(=O)(=O)NC(=O)[C@@H](N)CC(C)C)c2ccccc12] |
| 5.19 | C2 | 4.19 | 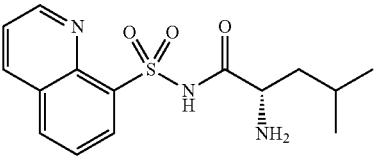 [SMILES: CC(C)C[C@H](N)C(=O)NS(=O)(=O)c1cccc2cccnc12] |
| 5.20 | C3 | 4.20 | 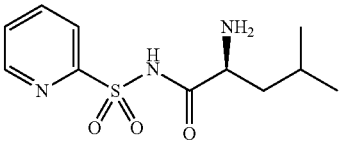 [SMILES: CC(C)C[C@H](N)C(=O)NS(=O)(=O)c1ccccn1] |
| 5.21 | C2 | 4.21 | 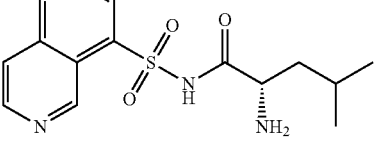 |
| 5.22 | C2 | 4.22 | 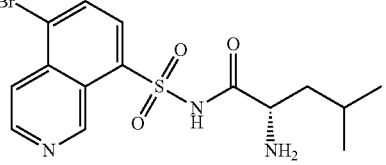 |
| 5.23 | C3 | 4.23 | 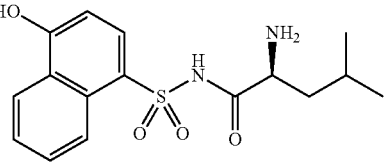 |
| 5.24 | C4 | 4.24 | 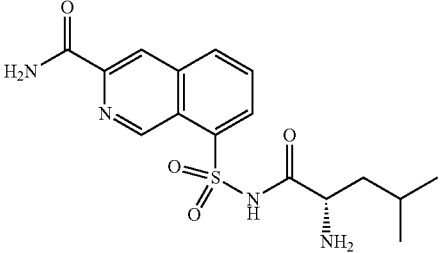 [SMILES: CC(C)C[C@H](N)C(=O)NS(=O)(=O)c1cccc2cc(C(N)=O)ncc12] |
| 5.25 | C2 | 4.25 | 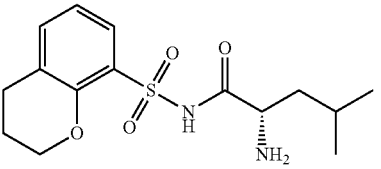 [SMILES: CC(C)C[C@H](N)C(=O)NS(=O)(=O)c1cccc2c1OCCC2] |

-continued

| Compound No | Procedure | Precursor | Structure |
|---|---|---|---|
| 5.27 | C3 | 4.27 | 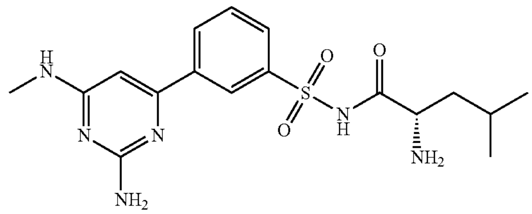 |
| 5.28 | C3 | 4.28 | 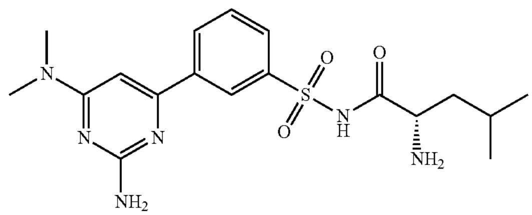 |
| 5.29 | C3 | 4.29 | 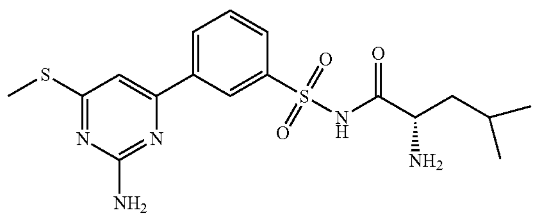 [SMILES: CSc1cc(-c2cccc(S(=O)(=O)NC(=O)[C@@H](N)CC(C)C)c2)nc(N)n1] |
| 5.30 | C3 | 4.30 | 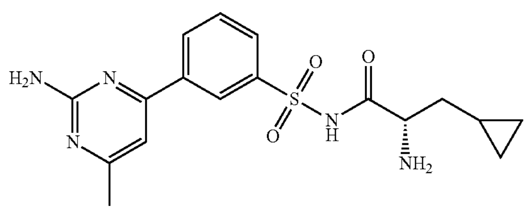 [SMILES: Cc1cc(-c2cccc(S(=O)(=O)NC(=O)[C@@H](N)CC3CC3)c2)nc(N)n1] |
| 5.31 | C3 | 4.31 | 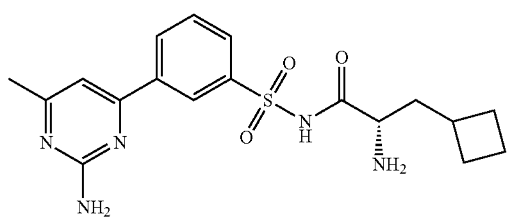 [SMILES: Cc1cc(-c2cccc(S(=O)(=O)NC(=O)[C@@H](N)CC3CCC3)c2)nc(N)n1] |
| 5.32 | C3 | 4.32 | 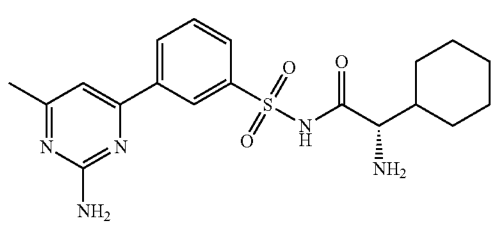 [SMILES: Cc1cc(-c2cccc(S(=O)(=O)NC(=O)[C@@H](N)C3CCCCC3)c2)nc(N)n1] |
| 5.33 | C2 | 4.33 | 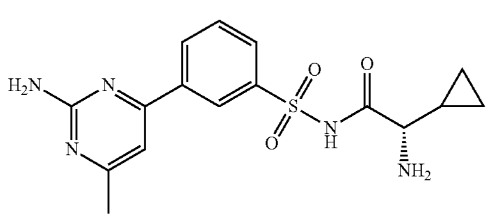 [SMILES: Cc1cc(-c2cccc(S(=O)(=O)NC(=O)[C@@H](N)C3CC3)c2)nc(N)n1] |

-continued
| Compound No | Procedure | Precursor | Structure |
|---|---|---|---|
| 5.34 | C3 | 4.34 | 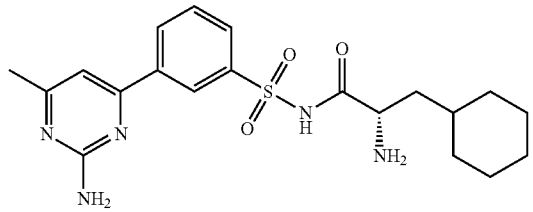 [SMILES: Cc1cc(-c2cccc(S(=O)(=O)NC(=O)[C@@H](N)CC3CCCCC3)c2)nc(N)n1] |
| 5.35 | C1 | 4.35 | 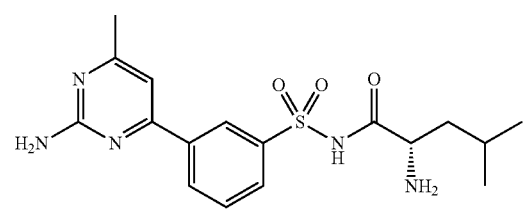 |
| 5.36 | C1 | 4.36 | 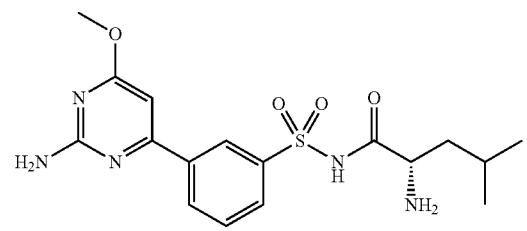 |
| 5.37 | C1 | 4.37 | 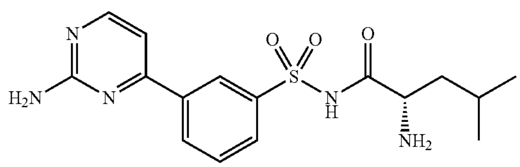 [SMILES: CC(C)C[C@H](N)C(=O)NS(=O)(=O)c1cccc(-c2ccnc(N)n2)c1] |
| 5.38 | C1 | 4.38 | 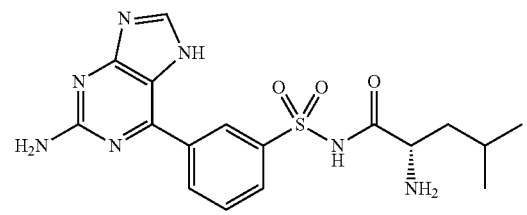 [SMILES: CC(C)C[C@H](N)C(=O)NS(=O)(=O)c1cccc(-c2nc(N)nc3nc[nH]c23)c1] |
| 5.39 | C1 | 4.39 | 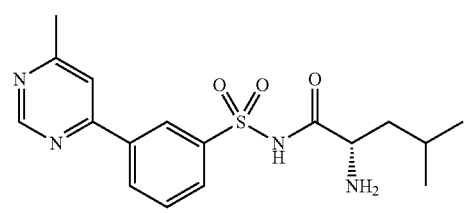 |
| 5.40 | C1 | 4.40 | 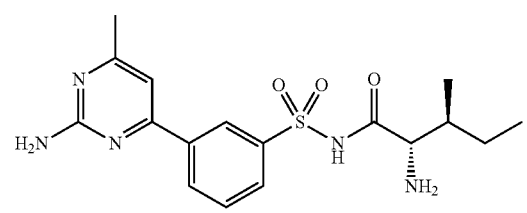 [SMILES: CC[C@H](C)[C@H](N)C(=O)NS(=O)(=O)c1cccc(-c2cc(C)nc(N)n2)c1] |

-continued

| Compound No | Procedure | Precursor | Structure |
|---|---|---|---|
| 5.41 | C1 | 4.41 | 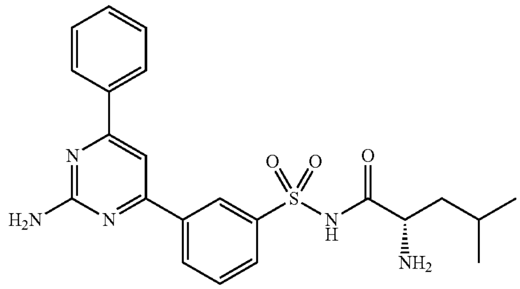 [SMILES: CC(C)C[C@H](N)C(=O)NS(=O)(=O)c1cccc(-c2cc(-c3ccccc3)nc(N)n2)c1] |
| 5.42 | C2 | 4.42 | 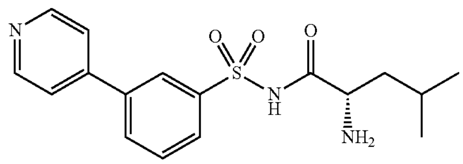 [SMILES: CC(C)C[C@H](N)C(=O)NS(=O)(=O)c1cccc(-c2ccncc2)c1] |
| 5.43 | C2 | 4.43 | 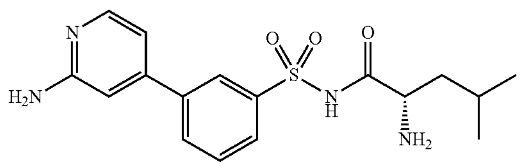 [SMILES: CC(C)C[C@H](N)C(=O)NS(=O)(=O)c1cccc(-c2ccnc(N)c2)c1] |
| 5.44 | C2 | 4.44 | 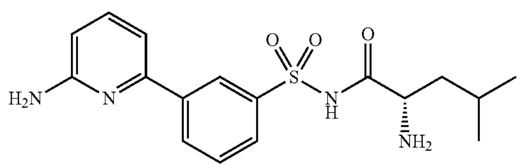 [SMILES: CC(C)C[C@H](N)C(=O)NS(=O)(=O)c1cccc(-c2cccc(N)n2)c1] |
| 5.45 | C2 | 4.45 | 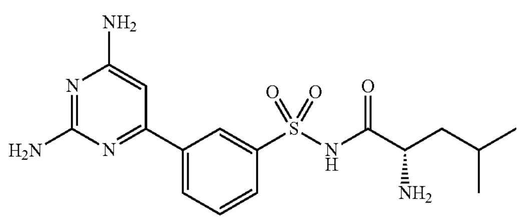 [SMILES: CC(C)C[C@H](N)C(=O)NS(=O)(=O)c1cccc(-c2cc(N)nc(N)n2)c1] |
| 5.46 | C2 | 4.46 | 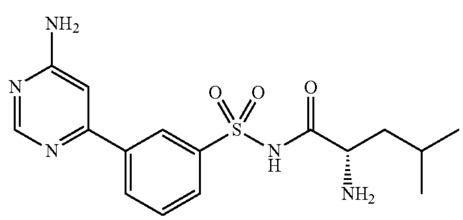 [SMILES: CC(C)C[C@H](N)C(=O)NS(=O)(=O)c1cccc(-c2cc(N)ncn2)c1] |
| 5.47 | C2 | 4.47 | 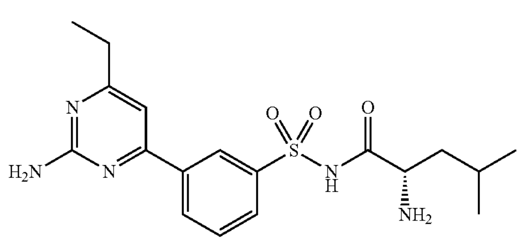 |

| Compound No | Procedure | Precursor | Structure |
|---|---|---|---|
| 5.48 | C2 | 4.48 | 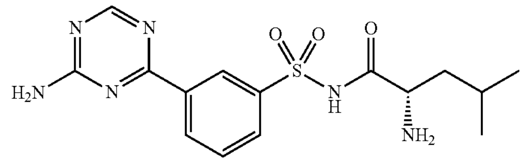 |
| 5.49 | C2 | 4.49 | 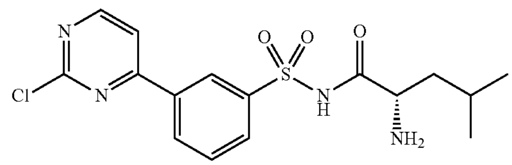 [SMILES: CC(C)C[C@H](N)C(=O)NS(=O)(=O)c1cccc(-c2ccnc(Cl)n2)c1] |
| 5.50 | C2 | 4.50 | 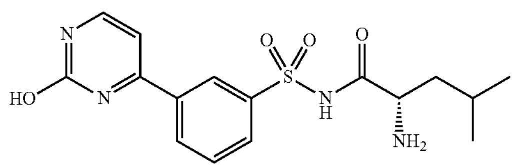 [SMILES: CC(C)C[C@H](N)C(=O)NS(=O)(=O)c1cccc(-c2ccnc(O)n2)c1] |
| 5.51 | C2 | 4.51 | 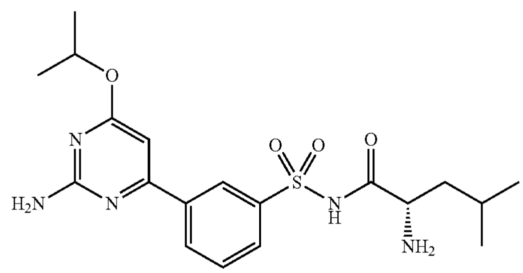 [SMILES: CC(C)C[C@H](N)C(=O)NS(=O)(=O)c1cccc(-c2cc(OC(C)C)nc(N)n2)c1] |
| 5.52 | C2 | 4.52 | 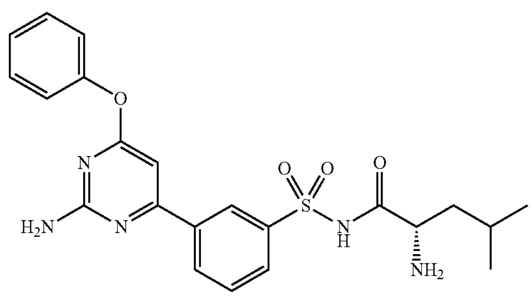 [SMILES: CC(C)C[C@H](N)C(=O)NS(=O)(=O)c1cccc(-c2cc(Oc3ccccc3)nc(N)n2)c1] |

Synthesis of 4-((tert-Butyldimethylsilyl)oxy)naphthalene-1-sulfonamide (2.23) (Scheme 2)

Method D 4-(Chlorosulfonyl)naphthalen-1-yl acetate (6) (prepared from sodium 4-hydroxynaphthalene-1-sulfonate as described in literature [Thea, S. et al. *J. Org. Chem.* 1985, 50, 2158]) (1.22 g; 4.29 mmol) was dissolved in dichloromethane (20 mL). The solution was cooled to 0-5° C. and 25% NH$_4$OH water solution (5 mL) was added dropwise. The reaction mixture was stirred at room temperature for 4 h and evaporated to dryness in vacuo. The residue was taken up in EtOAc/H$_2$O (50 ml/20 ml). The organic layer was separated, washed with brine (20 ml), dried, evaporated. The residue was purified by chromatography on silica gel, eluent: CH$_2$Cl$_2$/EtOH gradient from 100/0 to 100/2. To give intermediate 7, yield—0.62 g (65.3%). $^1$H NMR (DMSO-d$_6$) δ: 11.07 (s, 1H), 8.55 (d, J=8.5 Hz, 1H), 8.21 (dd, J=8.3, 1.5 Hz, 1H), 7.98 (d, J=8.2 Hz, 1H), 7.66 (ddd, J=8.5, 6.9, 1.5 Hz, 1H), 7.57 (ddd, J=8.3, 6.9, 1.1 Hz, 1H), 7.35 (s, 2H), 6.90 (d, J=8.2 Hz, 1H). LCMS (ESI) m/z: 224 [M+H]$^+$.

Method E

Intermediate 7 was transformed to 4-((tert-butyldimethylsilyl)oxy)naphthalene-1-sulfonamide (2.23) Prepared according to the procedure described in a patent [Corbett, T. H. et al. PCT Int. Appl., 2002098848, 12 Dec. 2002] used for the preparation of 4-(tert-butyl-dimethylsilanyloxi)-benzene-1-sulfonic acid amide. Yield 74.3%. $^1$H NMR (DMSO-d$_6$) δ: 8.63-8.57 (m, 1H), 8.26-8.20 (m, 1H), 8.04 (d, J=8.2 Hz, 1H), 7.70 (ddd, J=8.5, 6.9, 1.7 Hz, 1H), 7.66 (ddd, J=8.3, 6.9, 1.5 Hz, 1H), 7.48 (s, 2H), 7.04 (d, J=8.2 Hz, 1H), 1.06 (s, 9H), 0.34 (s, 6H). LCMS (ESI) m/z: 338 [M+H]$^+$.

Synthesis of 8-sulfamoyl-N-(2,4,4-trimethylpentan-2-yl)isoquinoline-3-carboxamide (4.24) (Scheme 3)

Method F. 1,2-Bis(bromomethyl)-3-iodobenzene (9)

To a solution of 1-iodo-2,3-dimethylbenzene (8) [prepared according to Chen, Y et al. *Org. Lett.* 2007, 9, 1899] (1.93 g, 8.32 mmol) in carbon tetrachloride (40 mL) was added NBS (3.67 g, 20.62 mmol), AIBN (0.070 g, 0.43 mmol) and the resulting mixture was gently refluxed by irradiation with a halogen lamp (500 W) for 4 h. The precipitate was filtered and washed with a small amount of carbon tetrachloride. The filtrate was concentrated under reduce pressure, the obtained residue was dissolved in EtOAc (100 ml), successively washed with 10% NaOH solution (20 mL), water (2×20 ml), 10% $Na_2S_2O_3$ solution (20 mL), water (20 mL), brine (20 mL), and dried ($Na_2SO_4$). The solvent was evaporated and the residue was purified by column chromatography on silica gel (eluent petroleum ether) to give 1.89 g (58.3%) of compound 9. $^1$H NMR ($CDCl_3$) δ: 7.84 (dd, J=8.1, 1.1 Hz, 1H), 7.33 (dd, J=7.6, 1.1 Hz, 1H), 6.97 (t, J=7.8 Hz, 1H), 4.85 (s, 2H), 4.66 (s, 2H). The product contained ca. 15-20% of an inseparable impurity (supposedly 1-bromo-2,3-bis(bromomethyl)benzene).

Method G. Diethyl 2-acetyl-8-iodo-1,4-dihydroisoquinoline-3,3(2H)-dicarboxylate (10)

A mixture of 1,2-bis(bromomethyl)-3-iodobenzene (9) (2.50 g, 6.41 mmol), diethyl 2-acetamidomalonate (1.39 g, 6.41 mmol), and $K_2CO_3$ (2.22 g, 16.06 mmol) in acetonitrile (40 mL) was refluxed for 70 h. The mixture was allowed to cool to ambient temperature, the precipitate was filtered and washed with a small amount of acetonitrile. The filtrate was concentrated under reduce pressure, the obtained residue was dissolved in EtOAc (100 mL), washed successively with saturated $NaHCO_3$ solution (30 mL), water (2×30 mL), brine (30 mL), and dried ($Na_2SO_4$). The solvent was evaporated and the residue was purified by column chromatography on silica gel (eluent petroleum ether-ethyl acetate, gradient from 20:1 to 20:6) to give 2 g of oil. The oil was dissolved in diethyl ether and kept in a refrigerator overnight. The precipitate was filtered and dried to give 0.4 g (14%) of a regioisomer diethyl 2-acetyl-5-iodo-1,4-dihydroisoquinoline-3,3(2H)-dicarboxylate. $^1$H NMR ($CDCl_3$) δ: 7.76 (d, J=8.0 Hz, 1H), 7.13 (d, J=7.5 Hz, 1H), 6.94 (t, J=7.7 Hz, 1H), 4.65 (s, 2H), 4.19 (q, J=7.1 Hz, 2H), 4.16 (q, J=7.1 Hz, 2H), 3.56 (s, 2H), 2.28 (s, 3H), 1.22 (t, J=7.1 Hz, 3H), 1.22 (t, J=7.1 Hz, 3H). LCMS (ESI) m/z: 446 [M+H]$^+$. The filtrate was evaporated and the residue was purified by column chromatography on silica gel (eluent petroleum ether-ethyl acetate, gradient from 20:1 to 20:6) to give 0.95 g (33.2%) of compound (10). $^1$H NMR ($CDCl_3$) δ: 7.73 (dd, J=7.9, 1.0 Hz, 1H), 7.14 (d, J=7.5 Hz, 1H), 6.95 (t, J=7.7 Hz, 1H), 4.67 (s, 2H), 4.17 (q, J=7.1 Hz, 2H), 4.15 (q, J=7.1 Hz, 2H), 3.40 (s, 2H), 2.33 (s, 3H), 1.17 (t, J=7.1 Hz, 3H), 1.17 (t, J=7.1 Hz, 3H). LCMS (ESI) m/z: 446 [M+H]$^+$. The structures of the regioisomers were determined by NOESY spectra. The product contained ca. 15-20% of an inseparable impurity (supposedly the corresponding bromo derivative diethyl 2-acetyl-8-bromo-1,4-dihydroisoquinoline-3,3(2H)-dicarboxylate). LCMS (ESI) m/z: 398 [M+H]$^+$.

Method H.
8-Iodo-1,2,3,4-tetrahydroisoquinoline-3-carboxylic acid (11)

A solution of diethyl 2-acetyl-8-iodo-1,4-dihydroisoquinoline-3,3(2H)-dicarboxylate (10) (0.585 g, 1.31 mmol) in 6N HCl (10 mL) was refluxed for 5 h. The mixture was cooled and conc. $NH_4OH$ water solution was added until pH of the medium was ~7. The precipitate was filtered, washed with a small amount of water, and dried to give 0.305 g (76.7%) of compound (11). Because of a low solubility of the product in common deuterated organic solvents and deuterium oxide, the $^1$H NMR spectrum was not informative. LCMS (ESI) m/z: 304 [M+H]$^+$. The product contained ca. 15-20% of an inseparable impurity (supposedly the corresponding bromo derivative 8-bromo-1,2,3,4-tetrahydroisoquinoline-3-carboxylic acid). LCMS (ESI) m/z: 256 [M+H]$^+$.

Method I. Methyl 8-iodo-1,2,3,4-tetrahydroisoquinoline-3-carboxylate (12)

To a suspension of 8-iodo-1,2,3,4-tetrahydroisoquinoline-3-carboxylic acid (11) (0.645 g, 2.13 mmol) in methanol (18 mL) slowly $SOCl_2$ (1.07 ml, 14.92 mmol) was added within 10 min. The reaction mixture was stirred at room temperature for 16 h, evaporated, and the residue was dissolved in a mixture of 1N $NaHCO_3$ solution (30 mL) and EtOAc (50 mL). The organic layer was separated and the aqueous layer was extracted with EtOAc (2×15 mL). The organic extracts were combined, washed successively with water (20 mL), brine (20 mL), and dried ($Na_2SO_4$). The solvents were evaporated to give compound 12 (0.570 g, 84%) which was used in the next step without further purification. $^1$H NMR ($CDCl_3$) δ: 7.67 (d, J=7.8 Hz, 1H), 7.10 (d, J=7.5 Hz, 1H), 6.87 (t, J=7.7 Hz, 1H), 4.07 (d, 16.6 Hz, 1H), 3.87 (d, J=16.6 Hz, 1H), 3.78 (s, 3H), 3.71 (dd, J=9.4, 5.0 Hz, 1H), 3.04 (dd, J=16.5, 5.0 Hz, 1H), 2.97 (dd, J=16.5, 9.4 Hz, 1H). LCMS (ESI) m/z: 318 [M+H]$^+$. The product contained ca. 15-20% of an inseparable impurity (supposedly the corresponding bromo derivative methyl 8-bromo-1,2,3,4-tetrahydroisoquinoline-3-carboxylate). LCMS (ESI) m/z: 270 [M+H]$^+$.

Method J. Methyl 8-iodoisoquinoline-3-carboxylate (13)

A mixture of methyl 8-iodo-1,2,3,4-tetrahydroisoquinoline-3-carboxylate (12) (0.570 g, 1.8 mmol) and 2,3-dichloro-5,6-dicyano-1,4-benzoquinone (DDQ) (0.449 g, 2.0 mmol) in toluene (20 mL) was refluxed for 6 h. To the reaction mixture was added another portion of DDQ (0.100 g, 0.45 mmol) and the refluxing was continued for 16 h. The mixture was allowed to cool to room temperature; the precipitate was filtered and washed with a small amount of toluene. The filtrate was evaporated and the residue was purified by column chromatography on silica gel (eluent petroleum ether-ethyl acetate, gradient from 100:0 to 100:15) to give 0.34 g (60%) of compound 13. $^1$H NMR ($CDCl_3$) δ: 9.50 (t, J=0.8 Hz, 1H), 8.46 (dd, J=0.8, 0.4 Hz, 1H), 8.28 (dd, J=7.4, 1.0 Hz, 1H), 7.96 (dtd, J=8.2, 0.9, 0.4 Hz, 1H), 7.48 (dd, J=8.2, 7.4 Hz, 1H), 4.07 (s, 3H). LCMS (ESI) m/z: 314 [M+H]$^+$. The product contained ca. 15-20% of an inseparable impurity (supposedly the corresponding bromo derivative methyl 8-bromoisoquinoline-3-carboxylate). LCMS (ESI) m/z: 266 [M+H]$^+$.

Method K. 8-Iodoisoquinoline-3-carboxylic acid (14)

A mixture of methyl 8-iodoisoquinoline-3-carboxylate (13) (0.237 g, 0.757 mol), 1M NaOH solution (1.14 mL, 1.14 mmol), and methanol (15 mL) was stirred in a closed vessel at 40° C. for 16 h. The reaction mixture was evaporated, mixed with water (10 mL), and 2N HCl solution was added until pH of the medium was ~5. The mixture was extracted with EtOAc (25 mL, 2×10 mL), the combined extracts were washed with water (10 mL), brine (10 mL), and dried (Na$_2$SO$_4$). The solvent was evaporated and the residue was dried in vacuo to give 0.210 g (92%) of compound 14. $^1$H NMR (CDCl$_3$) δ: 9.43 (s, 1H), 8.56 (s, 1H), 8.34 (dd, J=7.4, 0.9 Hz, 1H), 8.03 (d, J=8.2 Hz, 1H), 7.55 (dd, J=8.2, 7.4 Hz, 1H). LCMS (ESI) m/z: 300 [M+H]$^+$. The product contained ca. 15-20% of an inseparable impurity (supposedly the corresponding bromo derivative 8-bromoisoquinoline-3-carboxylic acid). LCMS (ESI) m/z: 352 [M+H]$^+$.

Method L. 8-Iodo-N-(2,4,4-trimethylpentan-2-yl) isoquinoline-3-carboxamide (15)

To a suspension of 8-iodoisoquinoline-3-carboxylic acid (14) (0.150 g, 0.500 mmol) in dichloromethane (12 mL) under argon atmosphere was added HOBt (0.111 g, 0.625 mmol) followed by EDC chloride (0.157 g, 0.625 mmol) and the resulting mixture was stirred at room temperature for 45 min. To the mixture was added tert-octylamine (0.106 g, 0.625 mmol) and stirring was continued for 2 h. The volatiles were evaporated and the residue (0.609 g) was purified by column chromatography on silica gel (eluent petroleum ether-ethyl acetate, 4:1) to give 0.163 g (79%) of compound 15. $^1$H NMR (CDCl$_3$) δ: 9.33 (t, J=0.8 Hz, 1H), 8.45 (s, 1H), 8.31 (b s, 1H), 8.21 (dd, J=7.4, 1.0 Hz, 1H), 7.95 (d, J=8.2 Hz, 1H), 7.43 (dd, J=8.2, 7.4 Hz, 1H), 1.92 (s, 2H), 1.60 (s, 6H), 1.05 (s, 9H). LCMS (ESI) m/z: 411.21 [M+H]$^+$. The product contained ca. 15-20% of an inseparable impurity (supposedly the corresponding bromo derivative 8-bromo-N-(2,4,4-trimethylpentan-2-yl)isoquinoline-3-carboxamide). LCMS (ESI) m/z: 363.18 [M+H]$^+$.

Method M. S-(3-((2,4,4-Trimethylpentan-2-yl)carbamoyl)isoquinolin-8-yl) benzothioate (16)

A mixture of 8-iodo-N-(2,4,4-trimethylpentan-2-yl)isoquinoline-3-carboxamide (15) (0.160 g, 0.39 mmol), thiobenzoic acid (0.065 g, 0.47 mmol), 1,10-phenanthroline (0.014 g, 0.078 mmol), DIPEA (0.100 g, 0.78 mmol), CuI (0.007 g (0.039 mmol), and toluene (3 mL) was stirred under argon atmosphere in a closed vessel at 110° C. temperature for 18 h. The mixture was evaporated and the residue was purified by column chromatography on silica gel (eluent petroleum ether-ethyl acetate, gradient from 6:1) to give 0.103 g (62.8%) of compound 16. $^1$H NMR (CDCl$_3$) δ: 9.51 (t, J=0.8 Hz, 1H), 8.63 (d, J=0.7 Hz, 1H), 8.30 (b s, 1H), 8.12-8.09 (m, 3H), 7.91 (dd, J=7.2, 1.1 Hz, 1H), 7.80 (dd, J=8.2, 7.2 Hz, 1H), 7.70-7.65 (m, 1H), 7.57-7.52 (m, 2H), 1.90 (s, 2H), 1.58 (s, 6H), 1.04 (s, 9H). LCMS (ESI) m/z: 421.26 [M+H]$^+$.

Method N. 8-Sulfamoyl-N-(2,4,4-trimethylpentan-2-yl)isoquinoline-3-carboxamide (2.24)

To a solution of S-(3-((2,4,4-trimethylpentan-2-yl)carbamoyl)isoquinolin-8-yl) benzothioate (16) (0.060 g, 0.143 mmol), benzyltriethylammonium chloride (0.110 g, 0.485 mmol), and water (0.0064 g, 0.356 mmol) in acetonitrile (2 ml) at 0° C. within 1 min. was added trichloroisocyanuric acid (0.040 g, 0.172 mmol) as a solid. The reaction mixture was stirred at this temperature for 30 min. and then 25% NH$_4$OH solution (0.40 ml, 0.858 mmol) was added. The stirring was continued at room temperature for 1 h and the mixture was diluted with acetonitrile (8 ml). The mixture was filtered, the filtrate was evaporated and the residue was purified by column chromatography on silica. gel (eluent hexane-ethyl acetate, 1:1) to give 0.042 g (81%) of compound 2.24. LCMS (ESI) m/z: 364.20 [M+H]$^+$.

Synthesis of chromane-8-sulfonamide (2.25) (Scheme 4)

Method O. Chromane-8-sulfonyl chloride (18)

8-Bromochromane (17) was prepared from commercial 2,6-dibromophenol according to the literature procedure [Kerrigan, F.; Martin, C; Thomas, G. H. Tetrah. Lett. 1998, 39, 2219]. To 8-bromochromane (17) (0.18 g, 0.84 mmol) in dry tetrahydrofuran (2 mL) at −78° C. under argon 2.5 M n-BuLi in hexanes (0.34 ml, 0.85 mmol) was added slowly. The reaction was stirred at this temperature for 30 min and then SO$_2$ (g) was bubbled through the solution for 3 minutes. The reaction was stirred at −78° C. then warmed to room temperature and the solvent was evaporated. The residue was dissolved in 2 ml of DCM and NCS (0.112 g, 0.84 mmol) was added at r.t., the reaction mixture stirred for 1 h, then diluted with 15 mL DCM, washed with water, brine, dried over sodium sulfate and the solvent was removed under vacuum. The residue was purified by column chromatography on silica gel (eluent petroleum ether-ethyl acetate, 3:1) to give 0.054 g (30%) of compound 18. Compound was unstable under GCMS and LCMS conditions. $^1$H NMR (CDCl$_3$) δ: 7.78-7.75 (m, 1H), 7.39-7.36 (m, 1H), 6.95 (t, J=7.8 Hz, 1H), 4.46 (t, J=5.4 Hz, 2H), 2.88 (t, J=6.5 Hz, 2H), 2.16-2.09 (m, 2H).

Method P. Chromane-8-sulfonamide (2.25)

To chromane-8-sulfonyl chloride (18) (0.053 g, 0.23 mmol) in acetonitrile (2 ml) was added aq. NH$_4$OH (1 mL) and the mixture was stirred for 10 min, then the solvent was evaporated. The residue was purified by column chromatography on silica gel (eluent chloroform-methanol, 30:1) to give 0.044 g (91%) of compound 2.25. $^1$H NMR (DMSO-d$_6$) δ: 7.51 (dd, J=7.8, 1.6 Hz, 1H), 7.28 (dd, J=7.6, 1.6 Hz, 1H), 6.96 (b s, 2H), 6.95 (t, J=7.7 Hz, 1H), 4.28 (t, J=5.3 Hz, 2H), 2.80 (t, J=6.4 Hz, 2H), 1.98-1.91 (m, 2H). LCMS (ESI) m/z: 213.0 [M−H]$^−$.

Synthesis of (3-(2-amino-6-methylpyrimidin-4-yl) benzenesulfonamide (2.35) (Scheme 5)

Method Q. 3-(4,4,5,5-Tetramethyl-1,3,2-dioxaborolan-2-yl)benzenesulfonamide (19)

Through a mixture of 3-bromobenzenesulfonamide (2.53) (0.620 g, 2.63 mmol), KOAc (1.032 g, 10.52 mmol), and PdCl$_2$(dppf)$_2$ (0.100 g, 0.137 mmol) in dioxane (20 mL) was bubbled argon for 10 min. To the reaction mixture was added bis(pinacolato)diboron (1.000 g, 3.94 mmol), the reaction vessel was closed, and the content was stirred at 110° C. for 24 h. The mixture was cooled to room temperature and filtered through Celite. The filtrate was concentrated and the residue was purified by column chromatography on silica gel (eluent petroleum ether-ethyl acetate, gradient from 4:1 to 1:1) to give 0.663 g (89%) of 3-(4,4,5,5-tetramethyl-1,3, 2-dioxaborolan-2-yl)benzenesulfonamide (19) as a white solid. $^1$H NMR (DMSO-d$_6$, HMDSO) δ: 8.14 (ddd, J=2.0, 1.1, 0.5 Hz, 1H), 7.93 (ddd, J=7.9, 2.0, 1.3 Hz, 1H), 7.85 (td, J=1.2, 7.4 Hz, 1H), 7.59 (ddd, J=7.9, 7.4, 0.5 Hz, 1H), 1.32 (s, 12H). LCMS (ESI) m/z: 284.0 [M+H]⁺.

Method R. (3-(2-Amino-6-methylpyrimidin-4-yl)benzenesulfonamide (2.35)

To a solution of 3-(4,4,5,5-tetramethyl-1,3,2-dioxaborolan-2-yl)benzenesulfonamide (19) (0.030 g, 0.106 mmol) in dioxane (3 mL) were added successively 2-amino-4-chloro-6-methylpyrimidine (0.015 g, 0.105 mmol), Na₂CO₃ (0.034 g, 0.321 mmol), and water (0.15 mL). Through the obtained mixture for 10 min was bubbled argon, to the mixture was added PdCl₂(dppf)₂ (0.004 g, 0.005 mmol), the reaction vessel was closed, and the content was stirred at 100° C. for 16 h. The mixture was cooled to room temperature and filtered through Celite. The filtrate was concentrated and the residue was purified by column chromatography on silica gel (eluent chloroform-methanol, gradient from 100:5 to 90:10) to give 0.014 g (50%) of 3-(2-amino-6-methylpyrimidin-4-yl)benzenesulfonamide (2.35). ¹H NMR (DMSO-d₆, HMDSO) δ: 8.54 (t, J=1.6 Hz, 1H), 8.23 (ddd, J=7.8, 1.5, 1.1 Hz, 1H), 7.92 (ddd, J=7.8, 1.7, 1.1 Hz, 1H), 7.69 (t, J=7.8 Hz, 1H), 7.42 (s, 2H), 7.09 (s, 1H), 6.67 (s, 2H), 2.32 (s, 3H). LCMS (ESI) m/z: 265.1 [M+H]⁺.

General Method S. Exemplified by the Synthesis of (S)-tert-butyl (4-methyl-1-oxo-1-(3-(4,4,5,5-tetramethyl-1,3,2-dioxaborolan-2-yl)phenylsulfonamido)pentan-2-yl)carbamate (20.27)

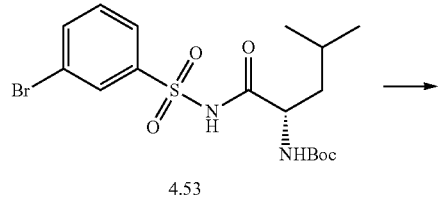

4.53

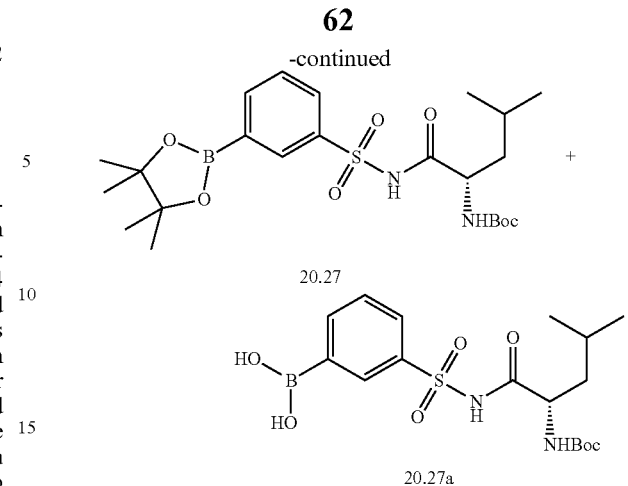

20.27

20.27a

Through a mixture of (S)-tert-butyl (1-(3-bromophenylsulfonamido)-4-methyl-1-oxopentan-2-yl)carbamate (4.53) (1.000 g, 2.23 mmol), KOAc (0.874 g, 8.9 mmol), and PdCl₂(dppf)₂ (0.18 g, 0.22 mmol) in dioxane (40 ml) was bubbled argon for 10 min. To the reaction mixture was added bis(pinacolato)diboron (0.85 g, 3.35 mmol), the reaction vessel was closed, and the content was stirred at 110° C. for 17 h. The mixture was cooled to room temperature and filtered through Celite. The filtrate was concentrated and the dark oily residue (3.0 g) was purified by column chromatography on silica gel (eluent petroleum ether-ethyl acetate, gradient from 4:1 to 1:1) to give 1.281 g of a mixture of (S)-tert-butyl (4-methyl-1-oxo-1-(3-(4,4,5,5-tetramethyl-1,3,2-dioxaborolan-2-yl)phenylsulfonamido)pentan-2-yl)carbamate (20.27) and (S)-(3-(N-(2-((tert-butoxycarbonyl)amino)-4-methylpentanoyl)sulfamoyl) phenyl)boronic acid (20.27a) as a glass-like material. The obtained mixture was utilized in the next step without further purification. LCMS (ESI) m/z: 495.28 [M–H]⁻ (20.27, retention time 3.939 min.) and 413.22 [M–H]⁻ (20.27a, retention time 2.750).

Following a method analogous to Method S the following compounds were obtained:

| Compound No | Method | Precursor | Structure |
|---|---|---|---|
| 20.27 | S | 4.53 | 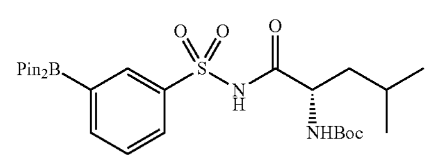 |
| 20.30 | S | 4.54 | 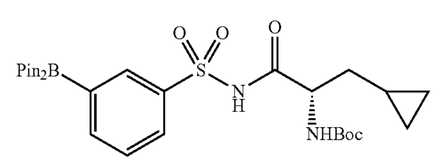 |
| 20.40 | S | 4.55 | 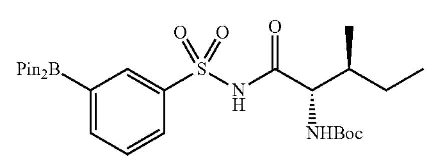 |

General Method T. Exemplified by the Synthesis of (S)-tert-butyl (1-(3-(2-amino-6-methylpyrimidin-4-yl)phenylsulfonamido)-4-methyl-1-oxopentan-2-yl)carbamate (4.35)

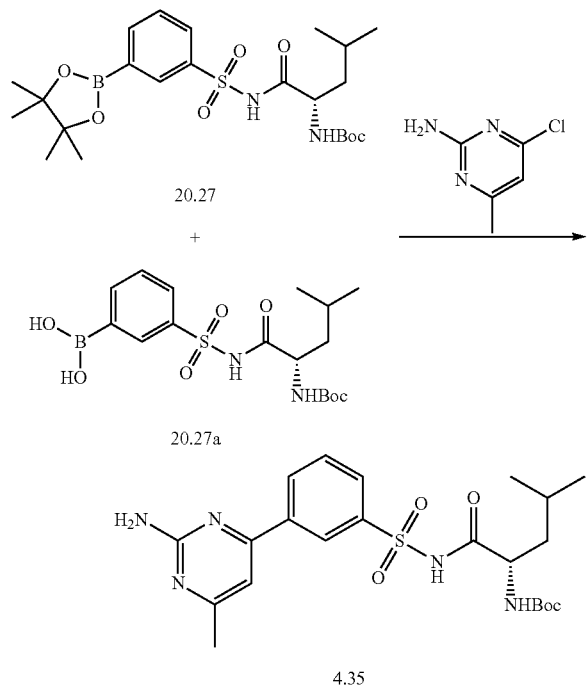

The mixture of (S)-tert-butyl (4-methyl-1-oxo-1-(3-(4,4,5,5-tetramethyl-1,3,2-dioxaborolan-2-yl)phenylsulfonamido)pentan-2-yl)carbamate (20.27) and (S)-(3-(N-(2-((tert-butoxycarbonyl)amino)-4-methylpentanoyl)sulfamoyl)phenyl)boronic acid (20.27a) (0.600 g), obtained in the preceding step, was dissolved in dioxane (34 mL) and to the prepared solution were added 2-amino-4-chloro-6-methylpyrimidine (0.174 g, 1.21 mmol), $Na_2CO_3$ (0.385 g, 3.63 mmol), and water (1.7 mL). Through the obtained mixture for 10 min was bubbled argon, to the mixture was added $PdCl_2(dppf)_2$ (0.045 g, 0.061 mmol), the reaction vessel was closed, and the content was stirred at 110° C. for 18 h. The mixture was cooled to room temperature and filtered through Celite. The filtrate was concentrated and the residue (0.76 g) was purified by column chromatography on silica gel (eluent chloroform-methanol, gradient from 100:1 to 100:2) to give 0.246 g (49.4%, calculated with respect to 3.1) of (S)-tert-butyl (1-(3-(2-amino-6-methylpyrimidin-4-yl)phenylsulfonamido)-4-methyl-1-oxopentan-2-yl)carbamate (4.35). $^1$H NMR (DMSO-$d_6$) δ: 12.33 (b s, 1H), 8.58 (s, 1H), 8.31 (d, J=7.9 Hz, 1H), 7.97 (d, J=7.9 Hz, 1H), 7.71 (t, J=7.9 Hz, 1H), 7.08 (s, 1H), 7.01 (b s, 1H), 6.70 (s, 2H), 4.00-3.90 (m, 1H), 2.32 (s, 3H), 1.63-1.19 (m, 3H), 1.28 (s, 9H), 0.80 (d, J=6.7 Hz, 3H), 0.78 (d, J=6.7 Hz, 3H). LCMS (ESI) m/z: 478.36 [M+H]$^+$.

Following a method analogous to Method T the following compounds were obtained:

| Compound No | Method | Precursor | Structure |
|---|---|---|---|
| 4.27 | T | 20.27 | 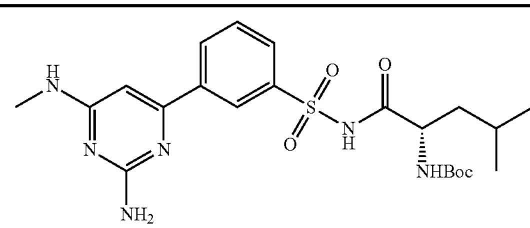 |
| 4.28 | T | 20.27 | 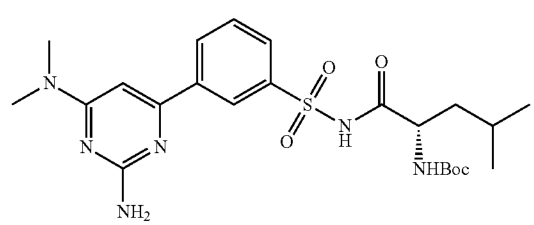 [SMILES: CC(C)C[C@H](NC(=O)OC(C)(C)C)C(=O)NS(=O)(=O)c1cccc(-c2cc(N(C)C)nc(N)n2)c1] |
| 4.29 | T | 20.27 | 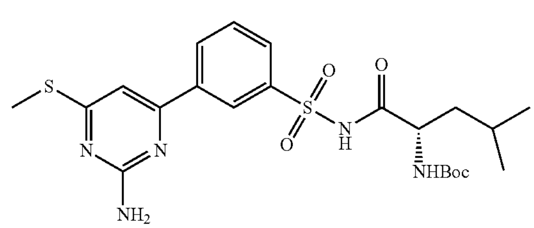 [SMILES: CSc1cc(-c2cccc(S(=O)(=O)NC(=O)[C@H](CC(C)C)NC(=O)OC(C)(C)C)c2)nc(N)n1] |

-continued
| Compound No | Method | Precursor | Structure |
|---|---|---|---|
| 4.30 | T | 20.30 | 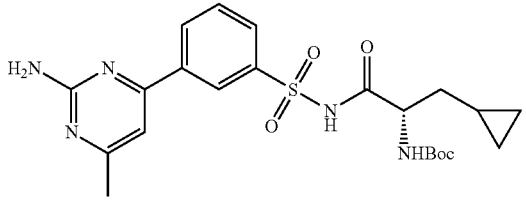 [SMILES: Cc1cc(-c2cccc(S(=O)(=O)NC(=O)[C@H](CC3CC3)NC(=O)OC(C)(C)C)c2)nc(N)n1] |
| 4.35 | T | 20.27 | 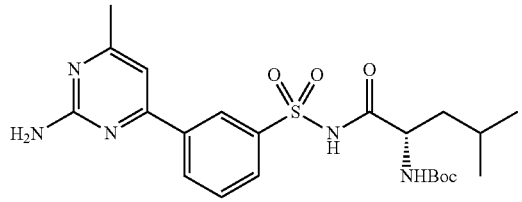 [SMILES: Cc1cc(-c2cccc(S(=O)(=O)NC(=O)[C@H](CC(C)C)NC(=O)OC(C)(C)C)c2)nc(N)n1] |
| 4.36 | T | 20.27 | 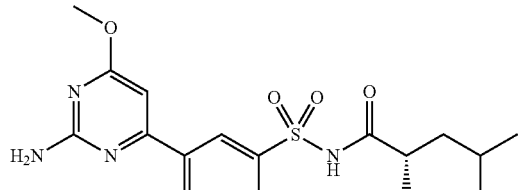 |
| 4.37 | T | 20.27 | 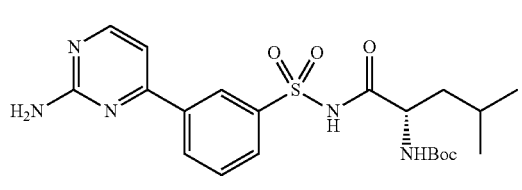 |
| 4.38 | T | 20.27 | 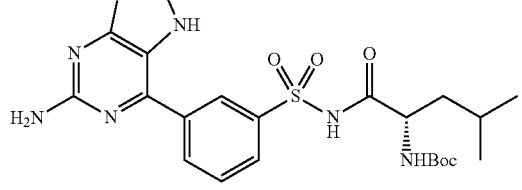 |
| 4.39 | T | 20.27 | 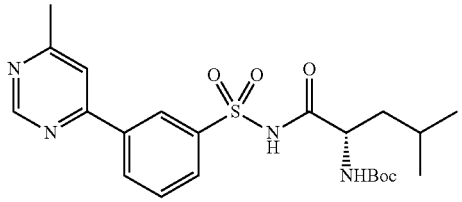 [SMILES: Cc1cc(-c2cccc(S(=O)(=O)NC(=O)[C@H](CC(C)C)NC(=O)OC(C)(C)C)c2)ncn1] |
| 4.40 | T | 20.27 | 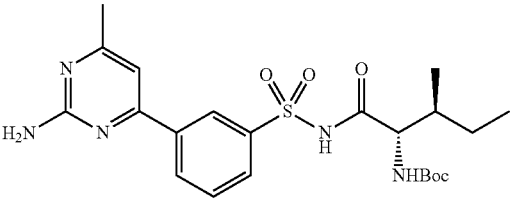 [SMILES: CC[C@H](C)[C@H](NC(=O)OC(C)(C)C)C(=O)NS(=O)(=O)c1cccc(-c2cc(C)nc(N)n2)c1] |

-continued

| Compound No | Method | Precursor | Structure |
|---|---|---|---|
| 4.41 | T | 20.27 | 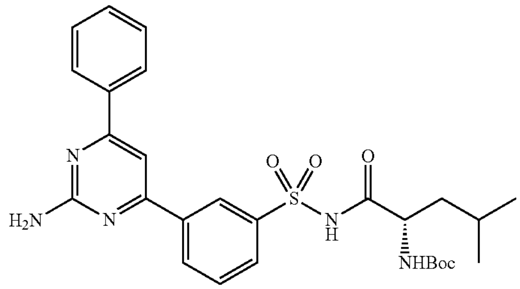 [SMILES: CC(C)C[C@H](NC(=O)OC(C)(C)C)C(=O)NS(=O)(=O)c1cccc(-c2cc(-c3ccccc3)nc(N)n2)c1] |
| 4.42 | T | 20.27 | 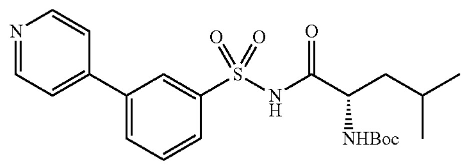 [SMILES: CC(C)C[C@H](NC(=O)OC(C)(C)C)C(=O)NS(=O)(=O)c1cccc(-c2ccncc2)c1] |
| 4.43 | T | 20.27 | 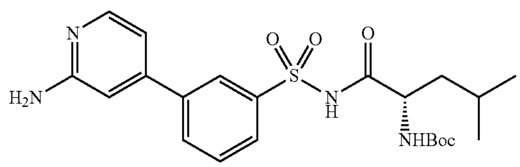 [SMILES: CC(C)C[C@H](NC(=O)OC(C)(C)C)C(=O)NS(=O)(=O)c1cccc(-c2ccnc(N)c2)c1] |
| 4.44 | T | 20.27 | 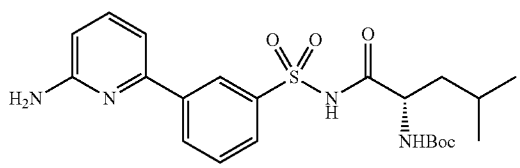 [SMILES: CC(C)C[C@H](NC(=O)OC(C)(C)C)C(=O)NS(=O)(=O)c1cccc(-c2cccc(N)n2)c1] |
| 4.45 | T | 20.27 | 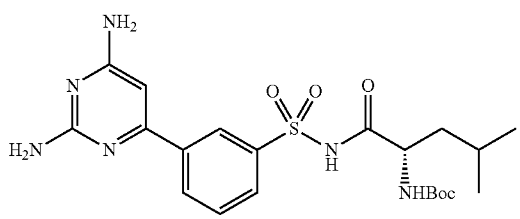 [SMILES: CC(C)C[C@H](NC(=O)OC(C)(C)C)C(=O)NS(=O)(=O)c1cccc(-c2cc(N)nc(N)n2)c1] |
| 4.46 | T | 20.27 | 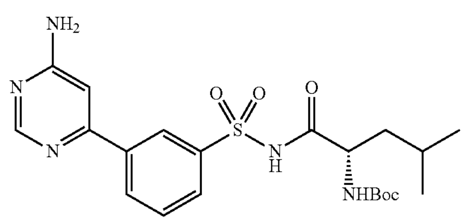 [SMILES: CC(C)C[C@H](NC(=O)OC(C)(C)C)C(=O)NS(=O)(=O)c1cccc(-c2cc(N)ncn2)c1] |
| 4.47 | T | 20.27 | 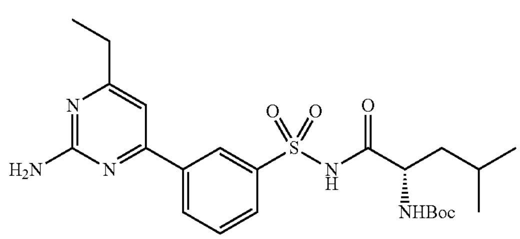 [SMILES: CCc1cc(-c2cccc(S(=O)(=O)NC(=O)[C@H](CC(C)C)NC(=O)OC(C)(C)C)c2)nc(N)n1] |

| Compound No | Method | Precursor | Structure |
|---|---|---|---|
| 4.48 | T | 20.27 | 3-(4-amino-1,3,5-triazin-2-yl)phenyl sulfonamide of (S)-Leu-NHBoc |
| 4.49 | T | 20.27 | 3-(2-chloropyrimidin-4-yl)phenyl sulfonamide of (S)-Leu-NHBoc |
| 4.51 | T | 20.27 | 3-(2-amino-6-isopropoxypyrimidin-4-yl)phenyl sulfonamide of (S)-Leu-NHBoc |
| 4.52 | T | 20.27 | 3-(2-amino-6-phenoxypyrimidin-4-yl)phenyl sulfonamide of (S)-Leu-NHBoc |

Method U. Synthesis of (S)-tert-butyl (1-(3-(2-hydroxypyrimidin-4-yl)phenylsulfonamido)-4-methyl-1-oxopentan-2-yl)carbamate (4.50)

To a solution of (S)-tert-butyl (1-(3-(2-chloropyrimidin-4-yl)phenylsulfonamido)-4-methyl-1-oxopentan-2-yl)carbamate (4.49) (0.189 g, 0.39 mmol) in THF (2 mL) was added 1 N aq. NaOH (22 mL) and the obtained emulsion was stirred at 55° C. for 1.5 h. The mixture was cooled to 0° C. and acidified to pH 3-4 by adding cold 2N aq. HCl (11 mL). The precipitate was filtered, the filtrate was extracted with EtOAc (3×25 mL), and the extract was dried ($N_2SO_4$). The solvents were evaporated, the residue was combined with the precipitate and purified by column chromatography on silica gel (eluent chloroform-methanol, 10:3) to give 0.110 g (60.5%) of (S)-tert-butyl (1-(3-(2-hydroxypyrimidin-4-yl)phenylsulfonamido)-4-methyl-1-oxopentan-2-yl)carbamate (4.50) as a foam. $^1$H NMR (DMSO-$d_6$, HMDSO) δ: 12.38 (b s, 1H), 12.05 (s, 1H), 8.63 and 8.58 (s and s, altogether 1H), 8.40-8.28 (m, 1H), 8.10 (d, J=6.3 Hz, 1H), 8.03 (d, J=7.5 Hz, 1H), 7.71 (t, J=7.7 Hz, 1H), 7.01 (d, J=6.3 Hz, 1H), 6.85 and 6.53 (b s and b s, altogether 1H), 3.94-3.85 and 3.84-3.73 (m and m, altogether 1H), 1.66-1.18 (m, 3H), 1.28 (s, 9H), 0.80 (d, J=6.2 Hz, 3H), 0.78 (d, J=6.2 Hz, 3H). LCMS (ESI) m/z: 465.4 [M+H]$^+$.

Method U. (S)-2-amino-4-methyl-N-((1,2,3,4-tetrahydroisoquinolin-8-yl)sulfonyl) pentanamide trifluoroacetate (5.26)

A mixture of (S)-2-amino-N-(isoquinolin-8-ylsulfonyl)-4-methylpentanamide trifluoroacetate (5.22) (0.050 g, 0.11 mmol) and 10% Pd/C (5 mg) in methanol (2 mL) was hydrogenated at 5 atm. for 4 h. The catalyst was removed by filtration, the solvent was evaporated under vacuum, and the residue was purified by Biotage purification system (C18HS 40+M column, eluent water-acetonitrile, gradient from 95:5 to 60:40) to give 0.030 g (59%) of compound 5.26, mp 90-92° C. $^1$H NMR (DMSO-$d_6$, HMDSO) δ: 0.86 (3H, d, J=6.2 Hz), 0.88 (3H, d, J=6.2 Hz), 1.43 (1H, ddd, J=5.5, 8.8, 13.8 Hz), m), 1.62 (1H, ddd, J=5.2, 8.7, 13.8 Hz), 1.67-1.77 (1H, m), 3.04 (2H, t, J=6.3 Hz), 3.29-3.40 (3H, m, overlapped with water), 4.67 (2H, s), 7.30 (1H, dd, J=1.8, 7.6 Hz), 7.33 (1H, t, J=7.5 Hz), 7.72 (3H, b s), 7.75 (1H, dd, J=1.8, 7.4 Hz), 9.03 (2H, b s). LCMS (ESI) m/z: 326.2 [M+H]$^+$. Anal. Calcd for $C_{15}H_{23}N_3O_3S \times 1.24\ CF_3COOH$ (30.3 C, 44.98, H, 5.23, N, 9.00. Found: C, 44.99, H, 5.38, N, 9.23.

All compounds were characterized by $^1$H-NMR and occasionally by $^{13}$C-NMR spectroscopy performed on Varian Mercury spectrometer (400 MHz) with chemical shifts values (δ) in ppm relative to internal standard, by tandem LC/MS spectrometer on Water Acquity UPLC with SQ mass selective detector, by elemental analyses, and occasionally by melting points. Physicochemical characterization of compounds 5.1-5.52.

| Compound ID | Compound No | Physicochemical characterization |
| --- | --- | --- |
| IK-698 | 5.1. | m.p. 192° C., $^1$H NMR (DMSO-$d_6$) δ: (DMSO-$d_6$) δ: 13.05 (b s, 1H), 8.43 (b s, 3H), 7.98-7.94 (m, 2H), 7.76-7.70 (m, 1H), 7.67-7.61 (m, 2H), 3.93-3.83 (m, 1H), 1.67-1.48 (m, 3H), 0.82 (d, J = 6.0 Hz, 3H), 0.81 (d, J = 6.1 Hz, 3H); $^{13}$C NMR (DMSO-$d_6$) δ: 169.1, 138.9, 133.9, 129.2, 127.6, 51.3, 23.4, 22.6, 21.7. LCMS ESI (m/z): 271.2 [M + H]$^+$ Anal. Calcd. for $C_{12}H_{18}N_2O_3S \times$ HCl (11.8%) × 0.06 H$_2$O (0.4%)): C 46.81, H 6.26, N 9.10. Found: C 46.81, H 6.21, N 9.02 |
| IK-713 | 5.2. | m.p. 224-225° C. $^1$H NMR (DMSO-$d_6$) δ: 8.38 (b s, 3H), 7.94 (distorted d, J = 9.0 Hz, 2H), 7.49 (distorted dd, J = 8.5, 7.4 Hz, 2H), 7.28 (distorted t, J = 7.4 Hz, 1H), 7.16-7.11 (m, 4H), 3.84 (b s, 1H), 1.65-1.47 (m, 3H), 0.84 (d, J = 6.0 Hz, 3H), 0.83 (d, J = 6.1 Hz, 3H). $^{13}$C NMR (DMSO-$d_6$) δ: 169.0, 161.7, 154.5, 132.6, 130.5, 125.2, 120.3, 117.2, 51.3, 23.4, 22.6, 21.7. LCMS ESI$^+$ (m/z): 363.2 [M + H]$^+$. Anal. Calcd for $C_{18}H_{22}N_2O_4S \times$ HCl (9.1%) × 0.15 H$_2$O (0.7%)): C 53.83, H 5.85, N 6.98, S 7.98; Found: C 53.80, H 5.85, N 6.98, S 7.62. |
| IK-718 | 5.3. | m.p. 143° C. (dec.). $^1$H NMR (DMSO-$d_6$) δ: 12.50 (b s, 1H), 8.11 (d, J = 7.3 Hz, 1H), 7.92 (b s, 3H), 7.65-7.46 (m, 2H), 7.46-7.30 (m, 5H), 7.27-7.18 (m, 1H), ~3.5-3.2 (1H, overlapped with water), 1.72-1.58 (m, 1H), 1.44-1.28 (m, 2H), 0.85 (d, J = 6.4 Hz, 3H), 0.81 (d, J = 6.4 Hz, 3H). $^{13}$C NMR (DMSO-$d_6$) δ: 171.0, 140.2, 132.2, 129.6, 129.4, 127.3, 127.1, 52.3, 23.5, 23.0, 21.1. LCMS ESI$^+$ (m/z): 347.26 [M + H]$^+$. Anal. Calcd for $C_{18}H_{22}N_2O_3S \times$ HCl (9.0%) × 1.2 H$_2$O (5.3%)): C 53.45, H 6.33, N 6.93, S 7.93. Found: C 53.52, H 6.03, N 6.76, S 7.41. |
| LL-20 | 5.4. | $^1$H NMR (CD$_3$OD) δ: 7.92 (s, 1H), 7.83 (d, J = 7.7 Hz, 1H), 7.55-7.39 (m, 2H), 3.55 (t, J = 6.8 Hz, 1H), 1.81-1.60 (m, 2H), 1.52 (t, J = 8.3 Hz, 1H), 0.94 (d, J = 6.0 Hz, 3H), 0.92 d, J = 6.0 Hz, 3H). LCMS ESI$^+$ (m/z): 305.8 [M + H]$^+$ |
| LL-19 | 5.5. | $^1$H NMR (CD$_3$OD) δ: 8.22 (dd, J = 7.9, 1.5 Hz, 1H), 7.75-7.58 (m, 2H), 7.53 (ddd, J = 7.8, 6.6, 2.0 Hz, 1H), 4.00-3.80 (m, 1H), 1.77-1.59 (m, 2H), 1.34-1.22 (m, 1H), 0.97 (d, J = 6.5, 6H). LCMS ESI$^+$ (m/z): 305.8 [M + H]$^+$ |
| EO-99 | 5.6. | $^1$H NMR (CD$_3$OD) δ: δ 8.04 (td, J = 7.6, 1.8 Hz, 1H), 7.86-7.66 (m, 1H), 7.49-7.24 (m, 2H), 3.86 (d, J = 3.1 Hz, 1H), 1.77-1.57 (m, 3H), 1.05-0.89 (m, 6H). LCMS ESI$^+$ (m/z): 289.34 [M + H]$^+$ |
| LL-23 | 5.7. | $^1$H NMR (CD$_3$OD) δ: 7.94 (d, J = 8.4 Hz, 2H), 7.40 (d, J = 8.4 Hz, 2H), 3.86 (t, J = 6.8 Hz, 1H), 2.70 (t, J = 7.7 Hz, 2H), 1.70-1.46 (m, 4H), 1.44-1.21 (m, 3H), 1.02-0.76 (m, 9H). LCMS ESI$^+$ (m/z): 327.46 [M + H]$^+$ |
| MZ-377 | 5.8. | m.p. 235-236° C. $^1$H NMR (DMSO-$d_6$) δ: 7.84 (distorted dd, J = 8.9, 5.6 Hz, 2H), 7.68 (b s, 3H), 7.21 (distorted t, J = 8.9 Hz, 2H), 3.32 (dd, J = 8.4, 5.7 Hz, 1H), 1.74-1.60 (m, 1H), 1.56 (ddd, J = 13.8, 8.3, 5.7 Hz, 1H), 1.38 (ddd, J = 13.8, 8.4, 6.0 Hz, 1H), 0.83 (d, J = 6.4 Hz, 3H), 0.82 (d, J = 6.4 Hz, 3H). $^{13}$C NMR (DMSO-$d_6$) δ: 172.7, 163.0 ($^1J_{CF}$ = 246.9 Hz), 141.8 ($^4J_{CF}$ = 2.9 Hz), 129.7 ($^3J_{CF}$ = 8.9 Hz), 114.5 ($^2J_{CF}$ = 22.1 Hz), 53.4, 40.5, 23.7, 22.7, 21.8. LCMS ESI$^+$ (m/z): 289.3 [M + H]$^+$. Anal. Calcd for $C_{12}H_{17}FN_2O_3S \times$ 0.11 H$_2$O (0.7%)): C 49.65, H 5.98, N 9.65; Found: C 49.66, H 6.01, N 9.61. |
| IK-681 | 5.9. | m.p. 149° C. (dec.). $^1$H NMR (DMSO-$d_6$) δ: 8.19 (b s, 3H), 8.16 (q, J = 1.5 Hz, 1H), 8.01 (d, J = 7.5 Hz, 1H), 7.93 (d, J = 8.0 Hz, 1H), 7.73 (t, J = 7.8 Hz, 1H), 7.72-7.68 (m, 2H), 7.56-7.51 (m, 2H), 7.48-7.43 (m, 1H), 3.86-3.74 (m, 1H), 1.64-1.45 (m, 3H), 0.82 (d, J = 6.0 Hz, 3H), 0.81 (d, J = 6.0 Hz, 3H). LCMS ESI (m/z): 347.1 [M + H]$^+$. Anal. Calcd. for $C_{18}H_{22}N_2O_3S \times$ HCl (8.3%) × 0.12 H$_2$O (0.5%) × 0.6 $C_4H_8O_2$ (12.1%)): C 55.95, H 6.45, N 6.40, S 7.32. Found: C 55.94, H 6.45, N 6.61, S 7.52. |
| DL-23-340 | 5.10. | m.p. 214.4° C. (single point, detected by OptiMelt). $^1$H NMR (CD$_3$OD) δ: 8.31 (td, J = 1.9, 0.5 Hz, 1H), 8.03 (ddd, J = 7.9, 1.9, 1.1 Hz, 1H), 7.99 (ddd, J = 7.9, 1.9, 1.1 Hz, 1H), 7.70 (td, J = 7.9, 0.5 Hz, 1H), 7.69-7.64 (m, 2H), 7.53-7.47 (m, 2H), 7.46-7.40 (m, 1H), 3.93 (t, J = 6.3 Hz, 1H), 1.75 (dt, J = 14.6, 6.8 Hz, 1H), 1.72 (ddd, J = 14.6, 6.9, 6.2 Hz, 1H), 0.68-0.57 (m, 1H), 0.51-0.36 (m, 2H), 0.10-0.00 (m, 2H). $^{13}$C NMR (CD$_3$OD) δ: 169.1, |

| Compound ID | Compound No | Physicochemical characterization |
|---|---|---|
| | | 143.6, 140.8, 140.3, 133.7, 130.8, 130.3, 129.5, 128.1, 127.9, 127.9, 55.3, 36.7, 6.8, 5.3, 4.8. LCMS ESI+ (m/z): 345.31 [M + H]+. Anal. Calcd for $C_{18}H_{20}N_2O_3S \times HCl$ (9.5%) × 0.16 $H_2O$ (0.8%)): C 56.34, H 5.60, N 7.30; Found: C 56.33, H 5.46, N 7.22. |
| IK-707 | 5.11. | m.p. 212° C. (dec.). $^1$H NMR (DMSO-$d_6$) δ: 8.17 (b s, 3H), 8.01 (d, J = 8.4 Hz, 2H), 7.91 (d, J = 8.4 Hz, 2H), 7.76-7.71 (m, 2H), 7.56-7.50 (m, 2H), 7.48-7.43 (m, 1H), 3.87-3.73 (m, 1H), 1.66-1.46 (m, 3H), 0.84 (d, J = 6.2 Hz, 3H), 0.84 (d, J = 6.2 Hz, 3H). $^{13}$C NMR (DMSO-$d_6$) δ: 169.2, 145.3, 138.3, 137.7, 129.2, 128.7, 128.4, 127.3, 127.1, 51.4, 23.4, 22.6, 21.6. LCMS ESI+ (m/z): 347.3 [M + H]+. Anal. Calcd. for $C_{18}H_{22}N_2O_3S \times 1.15$ HCl (9.2%) × 0.75 H2O (3.4%)): C 54.54, H 6.23, N 7.07, S 8.09. Found: C 54.54, H 6.34, N 7.23, S 7.37. |
| IK-719 | 5.12. | m.p. 217° C. $^1$H NMR (DMSO-$d_6$) δ: 7.67 (b s, 3H), 7.01 (s, 2H), 4.58 (septet, J = 6.4 Hz, 2H), 3.36-3.27 (m, 1H, overlapped with water), 2.82 (septet, J = 6.6 Hz, 1H), 1.83-1.63 (m, 2H), 1.48-1.34 (m, 1H), 1.22-1.08 (m, 18H), 0.87 (d, J = 5.8 Hz, 6H). $^{13}$C NMR (DMSO-$d_6$) δ: 172.4, 148.8, 148.6, 139.6, 122.0, 53.0, 40.8, 33.3, 28.0, 24.8, 23.7, 23.0, 21.2. LCMS ESI+ (m/z): 397.43 [M + H]+<br>Anal. Calcd. for $C_{21}H_{36}N_2O_3S \times 0.3$ HCl (2.7%)): C 61.89, H 8.98, N 6.87, S 7.87. Found %: C 62.03, H 9.03, N 6.65, S 7.48. |
| IK-666 | 5.13. | $^1$H NMR (DMSO-$d_6$) δ: 8.64 (d, J = 8.2 Hz, 1H), 8.33-8.20 (m, 2H), 8.08 (d, J = 7.8 Hz, 1H), 7.96 (b s, 3H), 7.76-7.62 (m, 3H), 3.72-3.58 (m, 1H), 1.50-1.36 (m, 2H), 1.31-1.19 (m, 1H), 0.73 (d, J = 5.7 Hz, 3H), 0.70 (d, J = 5.7 Hz, 3H). LCMS ESI (m/z): 321.2 [M + H]+. |
| IK-665 | 5.14. | m.p. 215° C. (dec.). $^1$H NMR (DMSO-$d_6$) δ: 13.08 (bs, 1H), 8.65 (d, J = 1.9 Hz, 1H), 8.31 (bs, 3H), 8.24 (d, J = 8.1 Hz, 1H), 8.17 (d, J = 8.8 Hz, 1H), 8.07 (d, J = 8.1 Hz, 1H), 7.92 (dd, J = 8.8, 1.9 Hz, 1H), 7.75 (ddd, J = 8.1, 6.9, 1.4 Hz, 1H), 7.70 (ddd, J = 8.1, 6.9, 1.4 Hz, 1H), 3.91-3.81 (m, 1H), 1.64-1.44 (m, 3H), 0.81 (d, J = 6.1 Hz, 6H). $^{13}$C NMR (DMSO-$d_6$) δ: 169.2, 136.0, 134.7, 131.4, 129.6, 129.5 (2), 129.3, 129.2, 127.8, 122.5, 51.4, 40.0, 23.4, 22.6, 21.5. LCMS ESI (m/z): 321.2 [M + H]+. Anal. Calcd. for $C_{16}H_{20}N_2O_3S \times HCl$ (9.5%) × 0.3 $C_4H_8O_2$ (6.9%) × 0.1 $H_2O$ (0.5%)): C 53.65, H 6.18, N 7.27, S 8.33. Found: C 53.65, H 6.21, N 7.34, S 8.56. |
| DG-500 | 5.15. | m.p. 229.7° C. (224.6-237.4° C.). $^1$H NMR (DMSO-$d_6$) δ: 13.07 (b s, 1H), 8.66 (d, J = 1.9 Hz, 1H), 8.36 (b s, 3H), 8.24 (d, J = 8.2 Hz, 1H), 8.16 (d, J = 8.8 Hz, 1H), 8.07 (d, J = 8.2 Hz, 1H), 7.92 (dd, J = 8.8, 1.9 Hz, 1H), 7.75 (ddd, J = 8.2, 7.0, 1.4 Hz, 1H), 7.70 (ddd, J = 8.2, 7.0, 1.4 Hz, 1H), 3.80 (b s, 1H), 1.91-1.79 (m, 1H), 1.28-1.15 (m, 1H), 1.07-0.92 (m, 1H), 0.79 (d, J = 7.0 Hz, 3H), 0.71 (t, J = 7.4 Hz, 3H). $^{13}$C NMR (DMSO-$d_6$) δ: 168.1, 135.9, 134.7, 131.4, 129.5, 129.4, 129.2, 129.2, 127.8, 127.7, 122.5, 56.8, 36.0, 23.6, 14.5, 11.1. LCMS ESI (m/z): 321.2 [M + H]+. Anal. Calcd. for $C_{16}H_{20}N_2O_3S \times HCl$ (9.1%) × $H_2O$ (4.5%) × 0.3 $C_4H_8O_2$ (6.6%)): C 51.48, H 6.38, N 6.98. Found: C 51.50, H 6.02, N 6.70. |
| MZ-335 | 5.16. | m.p. 178-180° C. $^1$H NMR (DMSO-$d_6$) δ: 8.65 (d, J = 8.3 Hz, 1H), 8.40-8.32 (m, 2H), 8.29 (b s, 3H), 7.74 (t, J = 8.0 Hz, 1H), 7.71 (t, J = 8.1 Hz, 1H), 7.45 (d, J = 7.5 Hz, 1H), 3.82 (m, overlapped with water, 1H), 2.92 (s, 6H), 1.46-1.25 (m, 3H), 0.70 (d, J = 5.8 Hz, 3H), 0.65 (d, J = 5.8 Hz, 3H). $^{13}$C NMR (DMSO-$d_6$) δ: 168.9, 154.8, 143.8, 133.9, 131.6, 130.5, 128.7, 128.4, 127.9, 124.3, 117.1, 51.3, 45.5, 23.2, 22.5, 21.6. LCMS ESI+ (m/z): 364.3 [M + H]+. Anal. Calcd for $C_{18}H_{25}N_3O_3S \times 2.9$ HCl (21.9%) × 0.75 H2O (2.8%)): C 44.79, H 6.14, N 8.70; Found: C 44.77, H 6.14, N 8.47. |
| MZ-343 | 5.17. | m.p. 230-232° C. $^1$H NMR (DMSO-$d_6$) δ: 8.28 (s, 1H), 7.93 (d, J = 9.0 Hz, 1H), 7.81 (dd, J = 8.7, 1.6 Hz, 1H), 7.79 (d, J = 8.7 Hz, 1H), 7.67 (b s, 3H), 7.34 (d, J = 2.5 Hz, 1H), 7.21 (dd, J = 9.0, 2.5 Hz, 1H), 3.33 (dd, J = 8.4, 5.6 Hz, overlapped with water), 1.76-1.62 (m, 1H), 1.58 (ddd, J = 13.8, 8.3, 5.6 Hz, 1H), 1.38 (ddd, J = 13.8, 8.4, 5.9 Hz, 1H), 0.83 (d, J = 6.4 Hz, 3H), 0.82 (d, J = 6.4 Hz, 3H). $^{13}$C NMR (DMSO-$d_6$) δ: 172.5, 158.3, 140.4, 135.0, 130.3, 127.0, 126.7, 126.0, 124.6, 119.1, 105.8, 55.3, 53.4, 40.6, 23.7, 22.7, 21.8. LCMS ESI+ (m/z): 351.2 [M + H]+. Anal. Calcd. for $C_{17}H_{22}N_2O_4S \times 1.02$ $H_2O$ (5.0%)): C 55.36, H 6.57, N 7.60. Found: C 55.35, H 6.48, N 7.60. |
| MZ-370 | 5.18. | m.p. 253-255° C. $^1$H NMR (DMSO-$d_6$) δ: 8.74 (ddd, J = 8.5, 1.4, 0.7 Hz, 1H), 8.16 (ddd, J = 8.2, 1.6, 0.7 Hz, 1H), 8.05 (d, J = 8.2 Hz, 1H), 7.60 (b s, 3H), 7.54 (ddd, J = 8.5, 6.8, 1.6 Hz, 1H), 7.49 (ddd, J = 8.2, 6.8, 1.4 Hz, 1H), 6.97 (d, J = 8.2 Hz, 1H), 3.26 (dd, |

| Compound ID | Compound No | Physicochemical characterization |
|---|---|---|
| | | J = 8.0, 5.7 Hz, 1H), 1.63-1.49 (m, 1H), 1.50 (ddd, J = 13.5, 8.0, 6.0 Hz, 1H), 1.21 (ddd, J = 13.5, 8.0, 5.7 Hz, 1H), 0.77 (d, J = 6.3 Hz, 3H), 0.73 (d, J = 6.3 Hz, 3H). $^{13}$C NMR (DMSO-$d_6$) δ: 172.3, 156.6, 133.3, 129.5, 128.7, 126.7, 126.4, 125.1, 124.9, 121.7, 102.3, 55.9, 53.4, 40.6, 23.7, 22.5, 21.8. LCMS ESI$^+$ (m/z): 351.4 [M + H]$^+$. Anal. Calcd for $C_{17}H_{22}N_2O_4S$): C 58.27, H 6.33, N 7.99. Found: C 58.30, H 6.31, N 7.99. |
| KS-1189 | 5.19. | $^1$H NMR (DMSO-$d_6$) δ 9.12 (dd, J = 4.2, 1.6 Hz, 1H), 8.59 (dd, J = 8.4, 1.7 Hz, 1H), 8.52 (dd, J = 7.4, 1.4 Hz, 1H), 8.40 (dd, J = 8.2, 1.4 Hz, 1H), 8.27 (bs, 1H), 8.15 (bs, 3H), 7.83 (t, J = 7.8 Hz, 1H), 7.76 (dd, J = 8.3, 4.2 Hz, 1H), 1.52-1.29 (m, 2H), 1.27-1.13 (m, 1H), 0.76 (d, J = 5.5 Hz, 3H), 0.69 (d, J = 5.6 Hz, 3H). |
| MZ-375 | 5.20. | m.p. 203-205° C. $^1$H NMR (DMSO-$d_6$) δ: 8.76-8.73 (m, 1H), 8.50 (b s, 3H), 8.18-8.11 (m, 2H), 7.77-7.70 (m, 1H), 3.89 (b s, 1H), 1.76-1.50 (m, 3H), 0.86 (d, J = 8.5 Hz, 3H), 0.86 (d, J = 8.5 Hz, 3H). $^{13}$C NMR (DMSO-$d_6$) δ: 169.6, 155.5, 150.2, 138.8, 128.2, 123.4, 51.3, 39.5, 23.4, 22.7, 21.7. LCMS ESI$^+$ (m/z): 372.3 [M + H]$^+$. Anal. Calcd. for $C_{11}H_{17}N_3O_3S$ × HCl (11.8%)): C 42.93, H 5.89, N 13.65. Found, C 43.00, H 6.04, N 13.23. |
| C-2724 | 5.21. | m.p. 55-57° C. $^1$H NMR (DMSO-$d_6$) δ: 0.73 (3H, d, J = 6.2 Hz), 0.74 (3H, d, J = 6.2 Hz), 1.20-1.34 (1H, m), 1.41-1.52 (2H, m), 3.48 (1H, m), 7.79 (3H, b s), 8.01 (1H, dd, J = 7.3, 8.2 Hz), 8.18 (1H, d, J = 5.8 Hz), 8.28 (1H, d, J = 8.2 Hz), 8.34 (1H, dd, J = 1.1, 7.3 Hz), 8.68 (1H, d, J = 5.8 Hz), 10.15 (1H, s). LCMS ESI (m/z): 322.1 [M + H]$^+$. Anal. Calcd. for $C_{15}H_{19}N_3O_3S$ × 2.7 $CF_3COOH$ (46.4%) × $H_2O$ (2.7%) × 0.12 Leu (2.4%)): C 38.26, H 3.84, N 6.59. Found, %: C 38.32, H 3.86, N 6.41. |
| C-2775 | 5.22. | m.p. 137-139° C. $^1$H NMR (DMSO-$d_6$) δ: 10.12 (1H, s), 8.74 (1H, d, J = 5.9 Hz), 8.27 (1H, d, J = 7.9 Hz), 8.14 (1H, d, J = 7.9 Hz), 8.06 (1H, dd, J = 5.9, 08 Hz), 7.73 (3H, b s), 3.47-3.37 (1H, m), 1.56-1.40 (2H, m), 1.30-1.20 (1H, m), 0.74 (3H, d, J = 6.3 Hz), 0.73 (3H, d, J = 6.3 Hz). LCMS ESI (m/z): 400.0 [M + H]$^+$. Anal. Calcd. For $C_{15}H_{18}BrN_3O_3S$ × 1.22 $CF_3COOH$ (25.6%) × 0.2 $H_2O$ (0.7%): C 38.58, H 3.64, N 7.74. Found: C 38.60, H 3.66, N 7.74. |
| MZ-368 | 5.23. | m.p. 250-252° C. $^1$H NMR (DMSO-$d_6$) δ: 10.60 (b s, 1H), 8.91 (ddd, J = 8.4, 1.2, 0.6 Hz, 1H), 8.15 (ddd, J = 8.2, 1.6, 0.6 Hz, 1H), 7.94 (d, J = 8.1 Hz, 1H), 7.60 (b s, 3H), 7.50 (ddd, J = 8.4, 6.8, 1.6 Hz, 1H), 7.44 (ddd, J = 8.2, 6.8, 1.2 Hz, 1H), 6.83 (d, J = 8.1 Hz, 1H), 3.27 (dd, J = 7.7, 5.8 Hz, 1H), 1.64-1.46 (m, 2H), 1.23 (ddd, J = 13.3, 8.0, 5.8 Hz, 1H), 0.77 (d, J = 6.2 Hz, 3H), 0.73 (d, J = 6.2 Hz, 3H). $^{13}$C NMR (DMSO-$d_6$) δ: 172.1, 155.6, 131.6, 130.1, 129.0, 126.5, 126.2, 124.6, 124.4, 122.0, 105.8, 53.4, 40.7, 23.7, 22.5, 21.8. LCMS ESI$^+$ (m/z): 337.3 [M + H]$^+$. Anal. Calcd. for $C_{16}H_{20}N_2O_4S$ × 0.2 $H_2O$ (1.0%) × 0.2 HCl (2.1%) × 0.17 $CH_3CN$ (2.0%)): C 55.40, H 6.01, N 8.58. Found, C 55.31, H 5.98, N 8.76. |
| IK-603 | 5.24. | m.p. 222.9° C. $^1$H NMR (DMSO-$d_6$) δ: 10.11 (s, 1H), 8.56 (s, 1H), 8.27 (d, J = 2.0 Hz, 1H), 8.24 (d, J = 7.3 Hz, 1H), 8.24 (d, J = 8.3 Hz, 1H), 7.87 (t, J = 7.8 Hz, 1H), 7.76 (d, J = 2.0 Hz, 1H), 7.63 (b s, 3H), 3.31 (dd, J = 7.7, 5.6 Hz, 1H), 1.52-1.44 (m, 2H), 1.26-1.19 (m, 1H), 0.74 (d, J = 5.9 Hz, 3H), 0.71 (d, J = 5.9 Hz, 3H). $^{13}$C NMR (DMSO-$d_6$) δ: 173.2, 166.2, 150.4, 143.8, 142.3, 136.0, 131.1, 130.0, 129.7, 124.5, 119.8, 53.4, 40.6, 23.7, 22.5, 21.8. LCMS ESI (m/z): 365.2 [M + H]$^+$. Anal. Calcd. for $C_{16}H_{20}N_4O_4S$ × 0.08 $CF_3COOH$ (2.3%) × 1.1 H2O (5.0%)): C 49.34, H 5.71, N 14.24, S 8.15. Found: C 49.34, H 5.77, N 14.16, 87.92 |
| AC-486 | 5.25. | m.p. 165° C. (dec.) $^1$H NMR (DMSO-$d_6$) δ: 0.87 (3H, d, J = 6.3 Hz), 0.88 (3H, d, J = 6.3 Hz), 1.38 (1H, ddd, J = 5.9, 8.7, 14.0 Hz), 1.65 (1H, ddd, J = 5.7, 8.7, 14.0 Hz), 1.75 (1H, m), 1.84-1.91 (2H, m), 2.73 (2H, t, J = 6.5 Hz), 3.28 (1H, dd, J = 5.7, 8.7 Hz, overlapped with water), 4.06-4.13 (2H, m), 6.76 (1H, t, J = 7.6 Hz), 7.06 (1H, d, J = 7.5 Hz), 7.54 (1H, dd, J = 7.8, 1.7 Hz), 7.62 (3H, b s). LCMS ESI (m/z): 327.1 [M + H]+. Anal. Calcd for $C_{15}H_{22}N_2O_4S$ × 1.2 $C_2HF_3O_2$ (28.6%) × 0.8 $H_2O$ (3.0%)): C 43.75, H 5.23, N 5.86; Found: C 43.78, H 4.98, N 6.30. |
| C-2727 | 5.26. | m.p. 90-92° C. $^1$H NMR (DMSO-$d_6$) δ: 0.86 (3H, d, J = 6.2 Hz), 0.88 (3H, d, J = 6.2 Hz), 1.43 (1H, ddd, J = 5.5, 8.8, 13.8 Hz), m), 1.62 (1H, ddd, J = 5.2, 8.7, 13.8 Hz), 1.67-1.77 (1H, m), 3.04 (2H, t, J = 6.3 Hz), 3.29-3.40 (3H, m, overlapped with water), 4.67 (2H, s), 7.30 (1H, dd, J = 1.8, 7.6 Hz), 7.33 (1H, t, J = 7.5 Hz), 7.72 (3H, b s), 7.75 (1H, dd, J = 1.8, 7.4 Hz), 9.03 (2H, b s). |

-continued

| Compound ID | Compound No | Physicochemical characterization |
|---|---|---|
| | | LCMS ESI (m/z): 326.2 [M + H]+. Anal. Calcd. for $C_{15}H_{22}N_3O_3S \times$ 1.24 $CF_3COOH$ (30.3%)): C 44.98, H 5.23, N 9.00. Found C 44.99, H 5.38, N 9.23. |
| 'DG-459 | 5.27. | $^1H$ NMR (DMSO-$d_6$) δ: 12.62 (b s, 1H), 8.65 (b s, 1H), 8.19 (s, 1H), 7.95 (d, J = 7.7 Hz, 1H), 7.95 (d, J = 7.7 Hz, 1H), 7.74 (b s, 3H), 7.60 (t, J = 7.7 Hz, 1H), ~8.2-7.1 (b s, 2H), 6.44 (s, 1H), 3.44-3.26 (m, 1H, overlapped with water), 2.91 (d, J = 4.6 Hz, 3H), 1.77-1.61 (m, 1H), 1.58 (ddd, J = 13.8, 8.1, 5.7 Hz, 1H), 1.41 (ddd, J = 13.8, 8.2, 6.2 Hz, 1H), 0.83 (d, J = 6.3 Hz, 3H), 0.82 (d, J = 6.3 Hz, 3H). $^{13}C$ NMR (DMSO-$d_6$) δ: 172.9, 170.1, 163.7, 163.6, 158.3, 158.1, 146.4, 129.7, 128.7, 128.2, 125.0, 53.4, 40.4, 27.5, 23.7, 22.7, 21.9. LCMS ESI (m/z): 393.2 [M + H]+. Anal. Calcd for $C_{17}H_{24}N_6O_3S \times$ HCl (8.3%) $\times$ 0.6 $H_2O$ (2.5%)): C 46.43, H 6.01, N 19.11. Found: C 46.46, H 6.22, N 19.02. |
| DG-457 | 5.28. | $^1H$ NMR (DMSO-$d_6$) δ: 12.63 (b s, 1H), 8.29 (s, 1H), 8.04 (d, J = 7.8 Hz, 1H), 7.96 (d, J = 7.8 Hz, 1H), 7.76 (b s, 3H), 7.58 (t, J = 7.8 Hz, 1H), 7.34 (b s, 2H), 6.59 (s, 1H), 3.45-3.30 (m, 1H, overlapped with water), 3.19 (s, 6H), 1.79-1.63 (m, 1H), 1.59 (ddd, J = 13.7, 8.2, 5.7 Hz, 1H), 1.41 (ddd, J = 13.7, 8.2, 6.0 Hz, 1H), 0.84 (d, J = 6.2 Hz, 3H), 0.83 (d, J = 6.2 Hz, 3H). $^{13}C$ NMR (DMSO-$d_6$) δ: 172.8, 162.7, 162.6, 146.2, 129.6, 128.8, 128.4, 125.1, 91.4, 53.3, 40.4, 37.5, 23.7, 22.7, 21.8. LCMS ESI (m/z): 407.3 [M + H]+. Anal. Calcd for for $C_{18}H_{26}N_6O_3S \times$ HCl (7.8%) $\times$ $H_2O$ (3.8%) $\times$ 0.1 $C_4H_8O_2$ (1.9%)): C 47.04, H 6.39, N 17.89. Found: C 46.95, H 6.33, N 17.79. |
| DG-460 | 5.29. | $^1H$ NMR (DMSO-$d_6$) δ: 8.51 (s, 1H), 8.07 (d, J = 7.4 Hz, 1H), 7.87 (d, J = 7.4 Hz, 1H), 7.68 (b s, 3H), 7.50 (t, J = 7.4 Hz, 1H), 7.00 (s, 1H), 6.80 (b s, 2H), 3.50-3.25 (m, 1H, overlapped with water), 2.52 (s, 3H), 1.77-1.51 (m, 2H), 1.45-1.31 (m, 1H), 0.83 (d, J = 6.2 Hz, 3H), 0.82 (d, J = 6.2 Hz, 3H). $^{13}C$ NMR (DMSO-$d_6$) δ: 172.7, 171.1, 162.9, 161.8, 145.9, 136.5, 128.9, 128.5, 128.0, 125.5, 102.2, 53.4, 40.5, 23.7, 22.7, 21.8, 11.8. LCMS ESI (m/z): 410.2 [M + H]+. Anal. Calcd for $C_{17}H_{23}N_5O_3S_2 \times$ 0.5 HCl (3.8%) $\times$ 0.12 $C_{16}H_{20}ClN_5O_3S$ (10.0%)): C 47.79, H 5.49, N 16.50. Found C 48.04, H 5.65, N 16.46 |
| IK-656 | 5.30. | m.p. >192° C. (dec.). $^1H$ NMR (DMSO-$d_6$) δ: 8.76 (t, J = 1.8 Hz, 1H), 8.47 (d, J = 8.0 Hz, 1H), 8.43 (b s, 3H), 8.19 (d, J = 7.8 Hz, 1H), 7.86 (t, J = 7.9 Hz, 1H), 7.56 (s, 1H), ~9-7 (b s, 3H), 4.03-3.91 (m, 1H), 2.50 (s, 3H, overlapped with DMSO), 1.72 (td, J = 6.7, 14.4 Hz, 1H), 1.60 (td, J = 6.8, 14.4 Hz, 1H), 0.69-0.57 (m, 1H), 0.33-0.16 (m, 2H), 0.04--0.13 (m, 2H). $^{13}C$ NMR (DMSO-$d_6$) δ: 168.8, 168.7, 140.0, 138.1, 135.8, 132.9, 131.1, 130.2, 126.9, 125.8, 106.2, 53.2, 34.9, 20.4, 5.8, 4.5, 4.0. LCMS ESI (m/z): 376.2 [M + H]+. Anal. Calcd for $C_{17}H_{21}N_5O_3S \times$ 2.5 HCl (18.5%) $\times$ 1.5 $H_2O$ (5.5%)): C 41.37, H 5.41, N 14.19. Found: C 41.35, H 5.31, N 14.27. |
| DG-466 | 5.31. | $^1H$ NMR (DMSO-$d_6$) δ: 8.75 (t, J = 1.7 Hz, 1H), 8.48 (ddd, J = 7.9, 1.6, 1.0 Hz, 1H), 8.43 (b s, 3H), 8.20 (ddd, J = 7.9, 1.9, 1.0 Hz, 1H), 7.87 (t, J = 7.9 Hz, 1H), 7.63 (s, 1H), 9.1-7.5 (b s, 2H), 3.90-3.79 (m, 1H), 2.52 (s, 3H), 2.27 (septet, J = 7.7 Hz, 1H), 1.96-1.76 (m, 4H), 1.76-1.53 (m, 3H), 1.45 (quintet, J = 9.0 Hz, 1H). $^{13}C$ NMR (DMSO-$d_6$) δ: 168.9, 166.6, 162.1, 157.4, 140.1, 135.5, 133.0, 131.3, 130.2, 126.9, 106.3, 51.5, 37.1, 30.4, 27.7, 27.3, 20.0, 17.8. LCMS ESI (m/z): 390.2 [M + H]+. Anal. Calcd. for $C_{18}H_{23}N_5O_3S \times$ 2.5 HCl (17.2%) $\times$ 0.36 $C_4H_8O_2$ (6.0%) $\times$ 1 $H_2O$ (3.4%)): C 44.03, H 5.77, N 13.20. Found: C 44.29, H 5.74, N 12.71. |
| DG-470 | 5.32. | $^1H$ NMR (DMSO-$d_6$) δ: (DMSO-$d_6$) δ: 8.75 (s, 1H), 8.48 (d, J = 7.6 Hz, 1H), 8.39 (b s, 3H), 8.18 (d, J = 7.9 Hz, 1H), 7.86 (t, J = 7.8 Hz, 1H), 7.65-7.56 (m, 1H), ~9.1-7.3 (b s, 2H), 3.87-3.74 (m, 1H), 2.52 (s, 3H), 1.85-1.68 (m, 1H), 1.68-1.49 (m, 3H), 1.49-1.35 (m, 2H), 1.15-0.86 (m, 5H) $^{13}C$ NMR (DMSO-$d_6$) δ: (DMSO-$d_6$) δ: 168.6, 166.9, 162.8, 158.1, 140.5, 136.0, 133.3, 131.7, 130.6, 127.3, 106.7, 57.3, 39.4, 28.3, 27.8, 25.8, 25.7, 20.6. LCMS ESI (m/z): 404.2 [M + H]+ Anal. Calcd. for $C_{19}H_{25}N_5O_3S \times$ 2.7 HCl (16.6%) $\times$ 1.1 $H_2O$ (3.3%) $\times$ 0.8 $C_4H_8O_2$ (11.9%)): C 45.02, H 6.18, N 11.83, S 5.41; Found: C 45.03, H 6.19, N 12.15, S 4.99. |
| IK-685 | 5.33. | m.p. 158° C. (dec.). $^1H$ NMR (DMSO-$d_6$) δ: 8.73 (s, 1H), 8.43 (d, J = 7.8 Hz, 1H), 8.35 (b s, 3H), 8.15 (d, J = 7.8 Hz, 1H), 7.95 (s, 1H), 7.84 (distorted t, J = 7.8 Hz, 1H), 7.45 (b s, 1H), ~8.8-7.0 (b s, 2H), 3.32-3.17 (m, 1H), 2.46 (s, 3H), 0.97-0.87 (m, 1H), 0.85-0.73 (m, 1H), 0.63-0.49 (m, 2H), 0.48-0.40 (m, 1H). LCMS ESI (m/z): 362.2 [M + H]+. |

| Compound ID | Compound No | Physicochemical characterization |
|---|---|---|
| | | Anal. Calcd. for $C_{16}H_{19}N_5O_3S \times 2$ HCl (14.6%) × 1.7 H2O (6.1%) × 0.4 C4H8O2): C 42.26, H 5.56, N 14.00, S 6.41. Found: C 42.18, H 5.33, N 13.84, S 6.44. |
| DG-469 | 5.34. | $^1$H NMR (DMSO-$d_6$) δ: 8.75 (t, J = 1.7 Hz, 1H), 8.48 (d, J = 8.1 Hz, 1H), 8.45 (b s, 3H), 8.18 (ddd, J = 7.7, 1.7, 0.8 Hz, 1H), 7.86 (t, J = 7.9 Hz, 1H), 7.61 (s, 1H), ~9.3-7.5 (b s, 2H), 4.00-3.90 (m, 1H), 2.52 (s, 3H), 1.62-1.45 (m, 7H), 1.27-1.14 (m, 1H), 1.14-0.97 (m, 3H), 0.87-0.68 (m, 2H). $^{13}$C NMR (DMSO-$d_6$) δ: 169.4, 166.6, 162.3, 157.5, 140.1, 135.6, 132.9, 131.2, 130.2, 126.9, 106.2, 50.8, 37.8, 32.6, 32.2, 32.0, 25.7, 25.5, 25.3, 20.1. LCMS ESI (m/z): 418.2 [M + H]$^+$. Anal. Calcd for $C_{20}H_{27}N_5O_3S \times 2.8$ HCl (17.1%) × 0.45 H2O (1.4%) × 0.8 C4H8O2 (11.8%)): C 46.58, H 6.25, N 11.71. Found, %: C 46.61, H 6.29, N 11.42. |
| IK-580 | 5.35. | m.p. 241-242° C. (dec.). $^1$H NMR (DMSO-$d_6$, HMDSO) δ: 8.50 (t, J = 1.7 Hz, 1H), 8.05 (ddd, J = 7.8, 1.7, 1.2 Hz, 1H), 7.88 (ddd, J = 7.8, 1.7, 1.2 Hz, 1H), 7.67 (b s, 3H), 7.50 (t, J = 7.8 Hz, 1H), 7.01 (s, 1H), 6.63 (s, 2H), 3.37-3.30 (m, 1H, overlapped with water), 2.31 (s, 3H), 1.73-1.60 (m, 1H), 1.58 (ddd, J = 13.7, 8.4, 5.6 Hz, 1H), 1.38 (ddd, J = 13.7, 8.3, 5.8 Hz, 1H), 0.83 (d, J = 6.3 Hz, 3H), 0.81 (d, J = 6.3 Hz, 3H). LCMS (ESI) m/z: 378.2 [M + H]$^+$. Anal. Calcd for $C_{17}H_{23}N_5O_3S \times 0.09$ CF$_3$COOH (2.5%) × 1.12 H$_2$O (4.9%): C 50.59, H 6.26, N 17.17. Found: C 50.59, H 6.32, N 17.23. |
| IK-617 | 5.36. | m.p. 87-88° C. (dec.). $^1$H NMR (DMSO-$d_6$) δ: 8.60 (1H, br s), 8.40-7.90 (5H, br m), 7.73 (1H, unresolved t, J~7.5 Hz), 7.50-6.75 (2H, m), 6.66 (1H, br s), 3.89 (3H, br s), 3.78 (1H, br s), 1.68-1.40 (3H, m), 0.93-0.71 (6H, br s). $^{13}$C NMR (DMSO-$d_6$) δ: 171.4, 169.7, 163.0, 158.5, 158.2, 140.3, 137.2, 131.6, 129.6, 129.3, 125.9, 92.7, 53.5, 51.7, 23.4, 22.6, 21.3. LCMS (ESI) m/z: 394.2 [M + H]$^+$. Anal. Calcd for $C_{17}H_{23}N_5O_4S \times 2.6$ CF$_3$COOH (42.7%) × 0.25 H$_2$O (0.6%): C 38.40, H 3.79, N 10.09. Found: C 38.42, H 4.16, N 9.70. |
| IK-587 | 5.37. | m.p. 224-226° C. (dec.). $^1$H NMR (DMSO-$d_6$, HMDSO) δ: 0.81 (3H, d, J = 6.5 Hz), 0.83 (3H, d, J = 6.5 Hz), 1.38 (1H, ddd, J = 5.8, 8.3, 13.7 Hz), 1.58 (1H, ddd, J = 5.6, 8.3, 13.7 Hz), 1.67 (1H, m), 3.32 (1H, dd, J = 5.6, 8.3 Hz, overlapped with water), 6.75 (2H, s), 7.09 (1H, d, J = 5.2 Hz), 7.52 (1H, t, J = 7.8 Hz), 7.67 (3H, b s), 7.89 (1H, ddd, J = 0.9, 1.6, 7.8 Hz), 8.06 (1H, ddd, J = 0.9, 1.6, 7.8 Hz), 8.33 (1H, d, J = 5.2 Hz) 8.53 (1H, t, J = 1.6 Hz). $^{13}$C NMR (DMSO-$d_6$) δ: 21.8, 22.7, 23.7, 40.5, 53.4, 105.8, 125.3, 125.4, 128.3, 128.9, 136.6, 146.0, 159.3, 163.0, 163.9, 172.7. LCMS (ESI) m/z: 364.1 [M + H]$^+$. Anal. Calcd for $C_{16}H_{21}N_5O_3S \times 0.05$ CF$_3$COOH (1.5%) × 0.85 H$_2$O (4.0%): C 50.30, H 5.96, N 18.22. Found: C 50.31, H 5.98, N 18.17. |
| K-615 | 5.38. | m.p. 117° C. (dec.). $^1$H NMR (DMSO-$d_6$) δ: 9.32 (1H, s), 9.03 (1H, d, J = 7.6 Hz), 8.25 (1H, s), 8.16 (3H, b s), 8.10 (1H, d, J = 7.6 Hz), 7.83 (1H, t, J = 7.6 Hz), 6.8-3.4 (broad water signal) 3.82 (1H, b s), 1.64-1.42 (3H, m), 0.84-0.76 (6H, b m). $^{13}$C NMR (DMSO-$d_6$) δ: 169.4, 160.0, 156.0, 150.5, 142.0, 139.5, 136.7, 134.0, 129.5, 129.4, 128.1, 123.6, 51.6, 23.4, 22.6, 21.3. LCMS (ESI) m/z: 404.2 [M + H]$^+$. Anal. Calcd for $C_{17}H_{21}N_7O_3S \times 2.65$ CF$_3$COOH (42.6%) × 0.2 H$_2$O (0.5%): C 37.77, H 3.42, N 13.82, S 4.52. Found: C 37.87, H 3.46, N 13.76, S 4.00. |
| IK-621 | 5.39. | m.p. 246° C. $^1$H NMR (DMSO-$d_6$, HMDSO) δ: 9.11 (d, J = 1.1 Hz, 1H), 8.61 (t, J = 1.6 Hz, 1H), 8.21 (ddd, J = 7.8, 1.6, 1.1 Hz, 1H), 7.98 (s, 1H), 7.94 (ddd, J = 7.8, 1.5, 1.1 Hz, 1H), 7.67 (b s, 3H), 7.58 (t, J = 7.8 Hz, 1H), 3.36-3.34 (m, 1H, overlapped with water), 2.55 (s, 3H), 1.67 (nonet, J = 6.6 Hz, 1H), 1.59 (ddd, J = 13.7, 8.1, 5.7 Hz, 1H), 1.38 (ddd, J = 13.7, 8.1, 5.9 Hz, 1H), 0.83 (d, J = 6.6 Hz, 3H), 0.81 (d, J = 6.6 Hz, 3H). $^{13}$C NMR (DMSO-$d_6$) δ: 173.2, 168.4, 162.1, 158.8, 146.8, 136.1, 129.8, 128.9, 128.9, 126.0, 116.8, 53.8, 41.0, 24.2, 24.1, 23.1, 22.2. LCMS (ESI) m/z: 363.1 [M + H]$^+$. Anal. Calcd for $C_{17}H_{22}N_4O_3S \times 0.3$ H$_2$O (1.5%): C 55.51, H 6.19, N 15.23. Found: C 55.51, H 6.25, N 15.19. |
| BM-13 | 5.40. | m.p. 97° C. $^1$H NMR (DMSO-$d_6$, HMDSO) δ 8.67 (t, J = 1.7 Hz, 1H), 8.32 (d, J = 7.8 Hz, 1H), 8.04 (ddd, J = 7.8, 1.7, 1.0 Hz, 1H), 7.95 (b s, 3H), 7.73 (t, J = 7.8 Hz, 1H), 7.24 (s, 1H), 7.20 (b s, 3H), 3.76-3.68 (m, 1H), 2.38 (s, 3H), 1.86-1.75 (m, 1H), 1.25-1.14 (m, 1H), 1.09-0.96 (m, 1H), 0.79 (d, J = 7.0 Hz, 3H), 0.73 (t, J = 7.4 Hz, 3H). LCMS (ESI) m/z: 378.2 [M + H]$^+$. Anal. Calcd for $C_{17}H_{23}N_5O_3S \times 2.56$ CF$_3$COOH (43.1%) × 0.4 H$_2$O (1.1%): C 39.27, H 3.93, N 10.35. Found: C 39.28, H 3.91, N 10.44. |
| IK-625 | 5.41. | m.p. 186-188° C. (dec). $^1$H NMR (DMSO-$d_6$, HMDSO) δ: 8.76 (s, 1H), 8.54-8.48 (m, 1H), 8.25-8.19 (m, 2H), 8.08-7.94 (m, |

| Compound ID | Compound No | Physicochemical characterization |
|---|---|---|
| | | 4H), 7.79-7.72 (m, 2H), 7.57-7.52 (m, 3H), 6.91 (b s, 2H), 3.76-3.65 (m, 1H, overlapped with water), 1.65-1.42 (m, 3H), 0.83 (d, J = 6.2 Hz, 3H), 0.82 (d, J = 6.2 Hz, 3H). $^{13}$C NMR (DMSO-d$_6$) δ: 169.6, 165.3, 163.9, 163.1, 158.5, 158.1, 138.1, 136.9, 132.1, 130.8, 129.6, 129.4, 128.7, 127.0, 126.0, 102.1, 51.6, 23.4, 22.6, 21.3. LCMS (ESI) m/z: 440.3 [M + H]$^+$. Anal. Calcd for $C_{22}H_{25}N_5O_3S \times 2.1\ CF_3COOH$ (34.3%) × 1.05 $H_2O$ (2.7%): C 45.09, H 4.22, N 10.03. Found: C 45.05, H 4.26, N 9.83. |
| IK-636 | 5.42. | m.p. 151° C. (dec). $^1$H NMR (DMSO-d$_6$, HMDSO) δ: 9.01 (b s, 2H), 8.49 (b s, 3H), 8.44 (s, 1H), 8.39 (b s, 2H), 8.33 (d, J = 7.2 Hz, 1H), 8.16 (d, J = 7.6 Hz, 1H), 7.89 (t, J = 7.4 Hz, 1H), ~9.4-7.2 (b s, 1H), 3.93 (b s, 1H), 1.68-1.51 (m, 3H), 0.83 (d, J = 5.7 Hz, 3H), 0.82 (d, J = 6.0 Hz, 3H). $^{13}$C NMR (DMSO-d$_6$) δ: 169.9, 153.2, 143.7, 140.9, 136.2, 133.6, 131.1, 130.3, 127.2, 124.7, 51.8, 23.9, 22.9, 22.2. LCMS (ESI) m/z: 348.2 [M + H]$^+$. Anal. Calcd for $C_{17}H_{21}N_3O_3S \times 2$ HCl (15.9%) × 2.1 $H_2O$ (8.3%): C 44.56, H 5.98, N 9.17. Found: C 44.54, H 5.57, N 9.06. |
| IK-634 | 5.43. | m.p. 141° C. (dec). $^1$H NMR (DMSO-d$_6$, HMDSO) δ: 13.86 (b s, 1H), 8.36-8.02 (m, 9H), 7.80 (t, J = 7.3 Hz, 1H), 7.36-7.31 (m, 1H), 7.22 (dd, J = 6.7, 1.6 Hz, 1H), 8.36-7.10 (b s, 1H), 3.74 (m, overlapped with water, 1H), 1.67-1.43 (m, 3H), 0.82 (d, J = 6.2 Hz, 3H), 0.82 (d, J = 6.3 Hz, 3H). $^{13}$C NMR (DMSO-d$_6$) δ: 170.0, 154.4, 152.2, 141.1, 136.7, 136.1, 131.9, 130.4, 129.4, 125.9, 110.4, 110.2, 51.7, 23.4, 22.5, 21.7. LCMS (ESI) m/z: 363.2 [M + H]$^+$. Anal. Calcd for $C_{17}H_{22}N_4O_3S \times 3$ HCl (22.0%) × 1.45 $H_2O$ (5.2%): C 41.01, H 5.65, N 11.25. Found: C 41.01, H 5.62, N 11.20. |
| IK-635 | 5.44. | m.p. 148° C. (dec). $^1$H NMR (DMSO-d$_6$, HMDSO) δ: 8.42 (t, J = 1.7 Hz, 1H), 7.96 (ddd, J = 7.8, 1.7, 1.1 Hz, 1H), 7.77 (ddd, 7.7, 1.7, 1.1 Hz, 1H), 7.65 (b s, 3H), 7.47 (dd, J = 8.1, 7.5 Hz, 1H), 7.43 (t, J = 7.7 Hz, 1H), 7.01 (dd, J = 7.5, 0.7 Hz, 1H), 6.43 (dd, J = 8.1, 0.7 Hz, 1H), 6.05 (b s, 2H), 3.35-3.29 (m, overlapped with water, 1H), 1.75-1.61 (m, 1H), 1.59 (ddd, J = 13.8, 8.4, 5.4 Hz, 1H), 1.38 (ddd, J = 13.8, 8.5, 5.8 Hz, 1H), 0.83 (d, J = 6.7 Hz, 3H), 0.81 (d, J = 6.7 Hz, 3H). $^{13}$C NMR (DMSO-d$_6$) δ: 172.6, 159.6, 153.7, 146.7, 138.9, 138.0, 127.7, 127.7, 126.8, 125.0, 108.3, 107.3, 53.4, 40.6, 23.7, 22.7, 21.8. LCMS (ESI) m/z: 363.2 [M + H]$^+$. Anal. Calcd for $C_{17}H_{22}N_4O_3S \times 0.36$ HCl (3.5%): C 54.37, H 6.00, N 14.92. Found: C 54.39, H 6.10, N 14.82. |
| IK-627 | 5.45. | m.p. 234° C. (dec). $^1$H NMR (DMSO-d$_6$, HMDSO) δ: 13.11 (b s, 1H), 8.51 (b s, 1H), 8.31 (b s, 3H), 8.28 (s, 1H), 8.22 (d, J = 7.9 Hz, 1H), 8.14 (d, J = 7.9 Hz, 1H), 7.84 (t, J = 7.9 Hz, 1H), 8.70-7.50 (b s, 4H), 6.53 (s, 1H), 3.87 (b s, 1H), 1.69-1.49 (m, 3H), 0.85 (d, J = 6.0 Hz, 3H), 0.84 (d, J = 6.1 Hz, 3H). LCMS (ESI) m/z: 379.2 [M + H]$^+$. Anal. Calcd for $C_{16}H_{22}N_6O_3S \times 3$ HCl (20.4%) × 2.7 $H_2O$ (9.1%): C 35.82, H 5.71, N 15.67. Found: C 35.78, H 5.62, N 15.22. |
| DG-435 | 5.46. | $^1$H NMR (DMSO-d$_6$, HMDSO) δ: 8.71 (unresolved d, J = 0.7 Hz, 1H), 8.63 (b s, 2H), 8.44 (t, J = 1.8 Hz, 1H), 8.29 (b s, 3H), 8.23 (ddd, J = 8.0, 1.8, 1.0 Hz, 1H), 8.15 (ddd, J = 8.0, 1.8, 1.0 Hz, 1H), 7.85 (t, J = 8.0 Hz, 1H), 7.14 (d, J = 0.7 Hz, 1H), ~9.5-7.0 (b s, 1H), 3.84 (b s, 1H, overlapped with water), 1.68-1.47 (m, 3H), 0.84 (d, J = 6.2 Hz, 3H), 0.83 (d, J = 6.3 Hz, 3H). LCMS (ESI) m/z: 364.2 [M + H]$^+$. Anal. Calcd for $C_{16}H_{21}N_5O_3S \times 3$ HCl (22.0%) × 1.3 $H_2O$ (4.7%): C 38.73, H 5.40, N 14.11. Found: C 39.07, H 5.28, N 13.64. |
| DG-437 | 5.47. | $^1$H NMR (DMSO-d$_6$, HMDSO) δ: 8.50 (s, 1H), 8.07 (d, J = 7.8 Hz, 1H), 7.88 (d, J = 7.6 Hz, 1H), 7.67 (b s, 3H), 7.50 (t, J = 7.7 Hz, 1H), 7.00 (s, 1H), ~9.0-6.9 (b s, 1H), 6.64 (s, 2H), 3.45-3.25 (m, 1H, overlapped with water), 2.59 (q, J = 7.6 Hz, 2H), 1.77-1.52 (m, 2H), 1.44-1.33 (m, 1H), 1.22 (t, J = 7.6 Hz, 3H), 0.85-0.79 (m, 6H). $^{13}$C NMR (DMSO-d$_6$) δ: 173.2, 172.7, 163.8, 163.1, 146.0, 136.9, 128.7, 128.3, 128.0, 125.3, 104.0, 53.4, 40.5, 30.3, 23.7, 22.7, 21.8, 12.8. LCMS (ESI) m/z: 392.2 [M + H]$^+$. |
| DG-440 | 5.48. | $^1$H NMR (DMSO-d$_6$, HMDSO) δ: 8.91 (t, J = 1.8 Hz, 1H), 8.66 (s, 1H), 8.62 (ddd, J = 7.9, 1.6, 1.1 Hz, 1H), 8.39 (unresolved d, J~5.9 Hz, 3H), 8.16 (ddd, J = 7.9, 2.0, 1.1 Hz, 1H), 7.93 (b s, 1H), 7.88 (b s, 1H), 7.82 (t, J = 7.9 Hz, 1H), ~9.5-7.0 (b s, 1H), 3.91 (m, 1H, overlapped with water), 1.63-1.49 (m, 3H), 0.81 (d, J = 6.1 Hz, 3H), 0.81 (d, J = 6.1 Hz, 3H). $^{13}$C NMR (DMSO-d$_6$) δ: 169.1, 168.1, 166.5, 166.4, 139.3, 136.6, 133.0, 131.1, 129.9, 127.3, 51.3, 23.4, 22.5, 21.7. LCMS (ESI) m/z: 365.2 [M + H]$^+$. Anal. Calcd for $C_{15}H_{20}N_6O_3S \times 3$ HCl (20.6%) × 0.3 $Et_2O$ (4.2%) × 0.4 $C_4H_8O_2$ (6.6%): C 40.24, H 5.54, N 15.82. Found: C 40.64, H 5.63, N 15.99. |

-continued

| Compound ID | Compound No | Physicochemical characterization |
|---|---|---|
| DG-444 | 5.49. | m.p. 231-238° C. (dec). $^1$H NMR (DMSO-$d_6$, HMDSO) δ: 8.93 (d, J = 5.2 Hz, 1H), 8.73 (t, J = 1.8 Hz, 1H), 8.52 (ddd, J = 7.9, 1.7, 1.0 Hz, 1H), 8.34 (b s, 3H), 8.27 (d, J = 5.2 Hz, 1H), 8.17 (ddd, J = 7.9, 1.9, 1.0 Hz, 1H), 7.86 (t, J = 7.9 Hz, 1H), 3.91-3.80 (m, 1H), 1.65-1.47 (m, 3H), 0.83 (d, J = 6.1 Hz, 6H). $^{13}$C NMR (DMSO-$d_6$) δ: 169.5, 164.3, 161.9, 160.6, 140.4, 135.4, 132.5, 130.8, 130.3, 126.2, 116.6, 66.3, 51.5, 23.4, 22.5, 21.6. LCMS (ESI) m/z: 383.2 [M + H]$^+$. Anal. Calcd for $C_{16}H_{19}ClN_4O_3S$ × HCl (8.6%) × 0.3 $H_2O$ (1.3%): C 45.25, H 4.89, N 13.19. Found: C 45.48, H 4.72 N 12.73. |
| DG-445 | 5.50. | m.p. 191-221° C. (dec). $^1$H NMR (DMSO-$d_6$, HMDSO) δ: 8.65 (unresolved t, J = 1.7 Hz, 1H), 8.49-8.38 (m, 4H), 8.21 (d, J = 6.3 Hz, 1H), 8.15 (d, J = 7.7 Hz, 1H), 7.82 (t, J = 7.8 Hz, 1H), 7.11 (d, J = 6.3 Hz, 1H), ~8.8-7.0 (b s, 1H), 3.95-3.86 (m, 1H), 1.66-1.50 (m, 3H), 0.81 (d, J = 5.9 Hz, 1H), 0.81 (d, J = 5.9 Hz, 3H). $^{13}$C NMR (DMSO-$d_6$) δ: 169.2, 168.6, 155.7, 149.7, 139.5, 136.3, 133.1, 130.7, 130.1, 126.7, 100.7, 51.3, 23.4, 22.5, 21.7. LCMS (ESI) m/z: 365.2 [M + H]$^+$. Anal. Calcd for $C_{16}H_{20}N_4O_4S$ × 2 HCl (15.2%) × 1.5 $H_2O$ (5.6%) × 0.2 $Et_2O$ (3.1%): C 42.11, H 5.68, N 11.69. Found: C 41.93, H 5.21, N 11.23. |
| DG-455 | 5.51. | $^1$H NMR (DMSO-$d_6$) δ: 8.48 (t, J = 1.7 Hz, 1H), 8.00 (ddd, J = 7.8, 1.6, 1.0 Hz, 1H), 7.85 (ddd, J = 7.8, 1.6, 1.0 Hz, 1H), 7.60 (b s, 3H), 7.46 (t, J = 7.8 Hz, 1H), 6.66 (b s, 2H), 6.45 (s, 1H), 5.31 (septet, J = 6.2 Hz, 1H), 3.40-3.27 (m, 1H, overlapped with water), 1.74-1.61 (m, 1H), 1.58 (ddd, J = 13.7, 8.3, 5.5 Hz, 1H), 1.38 (ddd, J = 13.7, 8.3, 5.9 Hz, 1H), 1.29 (d, J = 6.2 Hz, 6H), 0.83 (d, J = 6.5 Hz, 3H), 0.82 (d, J = 6.5 Hz, 3H). $^{13}$C NMR (DMSO-$d_6$) δ: 172.9, 170.2, 164.2, 163.6, 145.8, 136.8, 128.5, 128.1, 127.9, 125.3, 92.4, 67.6, 53.4, 40.7, 23.7, 22.7, 21.9, 21.8. LCMS (ESI) m/z: 422.2 [M + H]$^+$. Anal. Calcd for $C_{19}H_{27}N_5O_4S$ × 0.4 HCl (3.3%): C 52.33, H 6.33, N 16.06. Found: C 52.56, H 6.41, N 15.99. |
| DG-453 | 5.52. | $^1$H NMR (DMSO-$d_6$, HMDSO) δ: 8.63 (t, J = 1.6 Hz, 1H), 8.36 (ddd, J = 8.1, 1.6, 1.0 Hz, 1H), 8.32 (b s, 3H), 8.10 (ddd, J = 7.8, 1.6, 1.0 Hz, 1H), 7.80 (t, J = 7.9 Hz, 1H), 7.46 (distorted t, J = 7.8 Hz, 2H), 7.27 (distorted t, J = 7.4 Hz, 1H), (distorted d, J = 7.6 Hz, 2H), 6.89 (s, 1H), 3.94-3.82 (m, 1H, overlapped with water), 3.8-3.2 (2H, overlapped with water), 1.67-1.47 (m, 3H), 0.83 (d, J = 5.7 Hz, 3H), 0.83 (d, J = 5.7 Hz, 3H). $^{13}$C NMR (DMSO-$d_6$) δ: 171.4, 169.3, 161.6, 161.0, 152.2, 139.7, 135.4, 132.4, 130.1, 130.1, 129.9, 126.2, 125.7, 121.7, 94.2, 66.4, 51.4, 23.4, 22.6, 21.6. LCMS (ESI) m/z: 456.3 [M + H]$^+$. Anal. Calcd for $C_{22}H_{25}N_5O_4S$ × 2 HCl (12.9%) × 2 $H_2O$ (6.4%): C 46.81, H 5.54, N 12.41. Found: C 46.89, H 5.36, N 12.01. |

In Vitro Assay

The compounds have been tested for antibacterial activity in vitro as aminoacyl-tRNA synthetases (aaRS) inhibitors following the following process.

Targeted aaRSs

Leucyl-, valyl- and isoleucyl-tRNA synthetases (LRS, VRS and IRS, respectively) from *Escherichia coli* (Eco) and *Staphylococcus aureus* (Sau).

Protein Expression and Purification

*Escherichia coli* M15 cells transformed with plasmid pQE-60, or pQE-70, containing the open-reading frame sequence of one targeted aaRS were induced with 1 mM IPTG (Isopropyl β-D-1-thiogalactopyranoside) for 3 h at 37° C. Bacterial cells were harvested and lysed with 20 mM $NaH_2PO_4$ (pH 8.0), 200 mM NaCl, 10 mM imidazole and protease inhibitor cocktail (Roche). Pathogenic aaRS was purified by nickel affinity standard chromatography. Protein concentration was determined by spectrophotometry.

In Vitro tRNA Transcription tRNA$^{Leu}$, tRNA$^{Val}$ and tRNA$^{Ile}$ from *E. coli* and *S. aureus* were transcribed in vitro for 4 h at 37° C. using T7 RNA polymerase. Transcription reaction contained 40 mM Tris-HCl (pH 8.0), 22 mM MgCl2, 1 mM spermidine, 5 mM DTT, 0.01% Triton X-100, 4 mM GTP, 4 mM ATP, 4 mM UTP, 4 mM CTP, 16 mM GMP, 250 μM T7 RNA polymerase and 150 μg BstNI digested plasmid. Once finished, the reaction was applied on a 6% polyacrylamide-8 M urea denaturing gel to purify the transcribed tRNA and discard any impurities. Purified tRNA was quantified with Nanodrop 2000 (Thermo Scientific).

Determination of $IC_{50}$

The aminoacylation reaction catalyzed by aminoacyl-tRNA synthetases (aaRS) takes place in two steps. In the first step, aaRS activates its cognate amino acid with ATP; and in the second step the activated amino acid is loaded to its corresponding tRNA. This reaction can be summarized as follows:

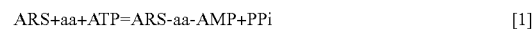

ARS+aa+ATP=ARS-aa-AMP+PPi [1]

ARS-aa-AMP+tRNA=aa-tRNA+AMP+ARS [2]

(ARS, Aminoacyl-tRNA synthetase; aa, amino acid; ARS-aa-AMP, enzyme-bound to aminoacyl-adenylate; aa-tRNA, aminoacyl-tRNA).

The activity of the pathogenic aaRSs was monitored by measuring the ATP consumption rate, since this consumption is directly proportional to the activity of the aaRS. If the tested compound, at a single point concentration of 50 μM, is inhibiting the aminoacylation reaction, there is a decrease in the ATP consumption, compared to the control reaction without compound, allowing the calculation of an inhibition ratio.

When the inhibition ratio for a given compound was above 80%, IC$_{50}$ determination was performed with the same enzymatic assay (using the commercial kit Kinase RR from BioThema AB, Sweden) in the presence of serial dilutions of inhibitor. Known inhibitors of LRS, VRS or IRS were used as a positive control of the assay. The IC$_{50}$ was calculated based on nonlinear regression analysis.

IC$_{50}$ values of for selected inhibitors of aminoacyl-tRNA synthethases

| Cmpd No | ID | IC50 EcoLRS (μM) | IC50 EcoIRS (μM) | IC50 EcoVRS (μM) | IC50 SauLRS (μM) | IC50 SauIRS (μM) | IC50 SauVRS (μM) |
|---|---|---|---|---|---|---|---|
| IK-698 | 5.1. | 0.035 | i.a. | i.a. | 5.4 | i.a. | i.a. |
| IK-713 | 5.2. | 0.713 | i.a | i.a | 16.3 | i.a | i.a |
| IK-718 | 5.3. | 0.159 | i.a | i.a | 14.8 | i.a | i.a |
| LL-20 | 5.4. | 0.031 | i.a | i.a | 0.92 | i.a | i.a |
| LL-19 | 5.5. | 0.121 | i.a | i.a | 13.2 | i.a | i.a |
| EO-99 | 5.6. | 0.233 | i.a | i.a | 17.0 | i.a | i.a |
| LL-23 | 5.7. | 0.668 | i.a | i.a | 4.9 | i.a | i.a |
| IK-681 | 5.9. | 0.032 | i.a | i.a | 0.65 | i.a | i.a |
| DL-23-340 | 5.10. | 47.6 | i.a | i.a | i.a | i.a | i.a |
| IK-707 | 5.11. | 27.6 | i.a | i.a | 11.3 | i.a | i.a |
| IK-719 | 5.12. | 32.7 | i.a | i.a | i.a | i.a | i.a |
| IK-666 | 5.13. | 0.059 | i.a | i.a | 16.1 | i.a | i.a |
| IK-665 | 5.14. | 0.065 | i.a | i.a | 1.0 | i.a | i.a |
| DG-500 | 5.15. | i.a | i.a | i.a | i.a | i.a | i.a |
| MZ-335 | 5.16. | 4.1 | i.a | i.a | i.a | i.a | i.a |
| MZ-343 | 5.17. | 0.92 | i.a | i.a | 2.0 | i.a | i.a |
| KS-1189 | 5.19. | 0.78 | i.a | i.a | 16.8 | i.a | i.a |
| C-2724 | 5.21. | 0.483 | i.a | i.a | 3.42 | i.a | i.a |
| C-2775 | 5.22. | 2.4 | i.a | i.a | 11.5 | i.a | i.a |
| IK-603 | 5.24. | 0.011 | i.a | i.a | 8.5 | i.a | i.a |
| AC-486 | 5.25. | 0.149 | i.a | i.a | 14.1 | i.a | i.a |
| C-2727 | 5.26. | 0.176 | i.a | i.a | 20.0 | i.a | i.a |
| DG-459 | 5.27. | 0.051 | i.a | i.a | 0.26 | i.a | i.a |
| DG-457 | 5.28. | 1.6 | i.a | i.a | 4.8 | i.a | i.a |
| DG-460 | 5.29. | 0.021 | i.a | i.a | 1.2 | i.a | i.a |
| IK-656 | 5.30. | 14.0 | i.a | i.a | i.a | i.a | i.a |
| DG-466 | 5.31. | 6.2 | i.a | i.a | i.a | i.a | i.a |
| DG-470 | 5.32. | 38.0 | i.a | i.a | i.a | 65.2 | i.a |
| IK-685 | 5.33. | 40%@50 uM | i.a | i.a | i.a | i.a | i.a |
| DG-469 | 5.34. | i.a | i.a | i.a | i.a | i.a | i.a |
| IK-580 | 5.35. | 0.014 | n.d. | i.a. | 4.34 | i.a. | i.a. |
| IK-617 | 5.36. | 0.012 | n.d. | i.a. | 3 | i.a. | i.a. |
| IK-587 | 5.37. | 0.054 | n.d. | i.a. | 2.18 | i.a. | i.a. |
| K-615 | 5.38. | 0.084 | n.d. | i.a. | 1.11 | i.a. | i.a. |
| IK-621 | 5.39. | 0.045 | n.d. | i.a. | 2.0 | i.a. | i.a. |
| BM-13 | 5.40. | 21.8 | n.d. | i.a. | i.a. | i.a. | i.a. |
| IK-625 | 5.41. | 0.22 | n.d. | i.a. | 3.0 | i.a. | i.a. |
| IK-636 | 5.42. | 0.013 | n.d. | i.a. | 0.81 | i.a. | i.a. |
| IK-634 | 5.43. | 0.002 | n.d. | i.a. | 0.33 | i.a. | i.a. |
| IK-635 | 5.44. | 0.006 | n.d. | i.a. | 1.64 | i.a. | i.a. |
| IK-627 | 5.45. | 0.02 | n.d. | i.a. | 0.72 | i.a. | i.a. |
| DG-435 | 5.46. | 0.01 | n.d. | i.a. | 1.3 | i.a. | i.a. |
| DG-437 | 5.47. | 0.011 | n.d. | i.a. | 2.15 | i.a. | i.a. |
| DG-440 | 5.48. | 0.0034 | n.d. | i.a. | 0.53 | i.a. | i.a. |
| DG-444 | 5.49. | 0.064 | n.d. | i.a. | 6.23 | i.a. | i.a. |
| DG-445 | 5.50. | 0.063 | n.d. | i.a. | 13.9 | i.a. | i.a. |
| DG-455 | 5.51. | 102%@50 μM | n.d. | n.d. | n.d. | n.d. | n.d. |
| DG-453 | 5.52. | 104%@50 μM | n.d. | n.d. | n.d. | n.d. | n.d. | i.a.—inactive at a concentration below 50 uM;
n.d.—not determined

Terms and Definitions

Unless otherwise defined herein, scientific and technical terms used in connection with the present invention have the meanings that are commonly understood by those of ordinary skill in the art.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl and the like. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix Ci-j indicates a moiety of the integer "i" to the integer "j" carbon atoms, inclusive. Thus, for example, $C_{1-6}$alkyl refers to alkyl of one to six carbon atoms, inclusive. The terms "cycloalkyl" and "carbocyclic" are synonyms and each means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The terms "heterocyclic", and "heterocyclo" are synonyms and each means a saturated or unsaturated (but not aromatic) monocyclic, fused, bridged, or spiro bicyclic heterocyclic ring system. Monocyclic heterocyclic rings contain from about 3 to 12 ring atoms, with from 1 to 5 heteroatoms selected from N, O, and S, and preferably from 3 to 7 member atoms, in the ring. In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$heterocyclyl" as used herein, pertains to a heterocyclyl group having 5 or 6 ring atoms. Examples of heterocyclic groups include cyclic ethers (oxiranes) such as ethyleneoxide, tetrahydrofuran, dioxane. Heterocycles containing nitrogen are groups such as pyrrolidine, piperidine, piperazine, tetrahydrotriazine, tetrahydropyrazole. Typical sulfur containing heterocycles include tetrahydrothiophene, dihydro-1,3-dithiol-2-yl, and hexahydrothiophen-4-yl. For heterocycles containing sulfur, the oxidized sulfur heterocycles containing SO or $SO_2$ groups are also included. Examples include the sulfoxide and sulfone forms of tetrahydrothiophene. Other commonly employed heterocycles include dihydrooxathiol-4-yl, dihydro-1H-isoindole, tetrahydro-oxazolyl, tetrahydro-oxadiazolyl, tetrahydrodioxazolyl, tetrahydrooxathiazolyl, hexahydrotriazinyl, tetrahydro-oxazinyl, morpholinyl and thiomorpholinyl.

As used herein, the term "alkenyl" as a group or a part of a group refers to a linear or branched hydrocarbon group containing one or more carbon-carbon double bonds and containing the indicated number of carbon atoms. Examples of such groups include ethenyl, propenyl, butenyl, pentenyl or hexenyl and the like.

As used herein, the term "alkynyl" as a group or a part of a group refers to a linear or branched hydrocarbon group containing one or more carbon-carbon triple bonds and containing the indicated number of carbon atoms. Examples of such groups include ethynyl, propynyl, butynyl, pentynyl or hexynyl and the like.

The term "oxo" means a doubly bonded oxygen.

The term "halo" means, fluoro, chloro, bromo or iodo.

As used herein, the term "aryl", pertains to a monovalent moiety obtained by removing a hydrogen atom from an aromatic ring atom of an aromatic compound, said compound having one ring, or two or more rings (e.g., fused), wherein at least one of said ring(s) is an aromatic ring. Preferably, each ring has from 5 to 7 ring atoms. In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-7}$aryl, $C_{5-6}$aryl.

The ring atoms may be all carbon atoms, as in "carboaryl groups" (e.g., $C_{5-20}$carboaryl). Examples of carboaryl groups include, but are not limited to, those derived from benzene (i.e., phenyl) (C6), naphthalene (C10), azulene (C10), anthracene (C14), phenanthrene (C14), naphthacene (C18), and pyrene (C16).

Examples of aryl groups which comprise fused rings, at least one of which is an aromatic ring, include, but are not limited to, groups derived from indene (C9), isoindene (C9), and fluorene (C13).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

N1: pyrrole (azole) (C5), pyridine (azine) (C6);

O1: furan (oxole) (C5);

S1: thiophene (thiole) (C5);

N1O1: oxazole (C5), isoxazole (C5), isoxazine (C6);

N2O1: oxadiazole (furazan) (C5);

N3O1: oxatriazole (C5);

N1S1: thiazole (C5), isothiazole (C5);

N2: imidazole (1,3 diazole) (C5), pyrazole (1,2 diazole) (C5), pyridazine (1,2 diazine) (C6), pyrimidine (1,3 diazine) (C6) (e.g., cytosine, thymine, uracil), pyrazine (1,4 diazine) (C6);

N3: triazole (C5), triazine (C6); and,

N4: tetrazole (C5).

The invention claimed is:

1. A compound selected from the following compounds and pharmaceutically acceptable salts thereof:

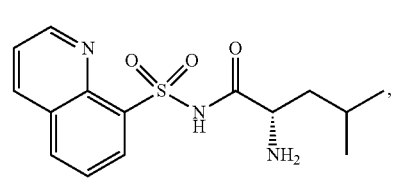
(KS-1189)

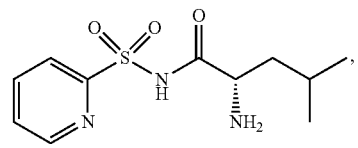
(MZ-375)

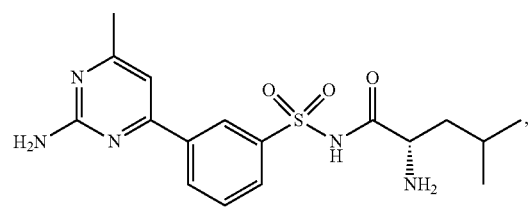
(IK-580)

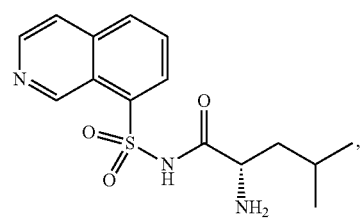
(C-2724)

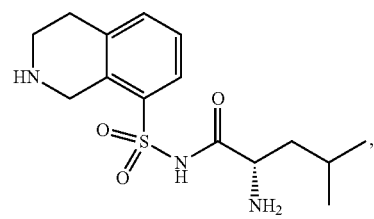
(C-2727)

(AC-486)
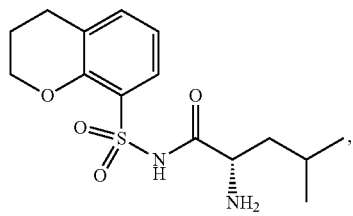
(IK-587)
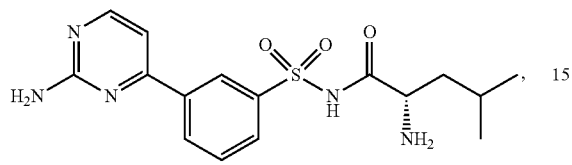
(IK-603)
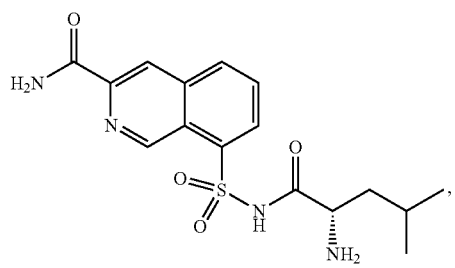
(C-2775)
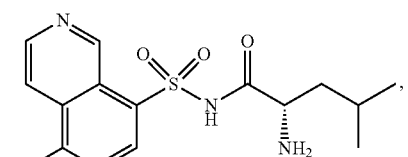
(IK-617)
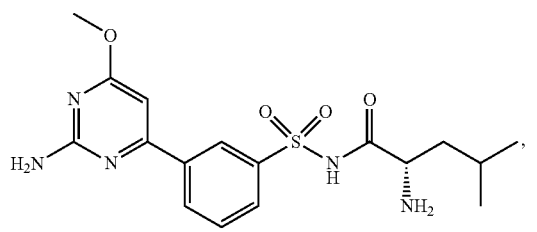
(IK-615)
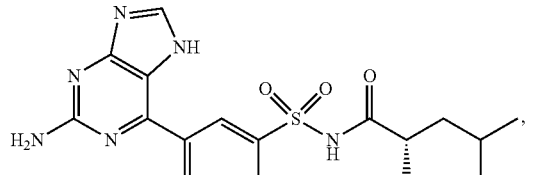
(IK-621)
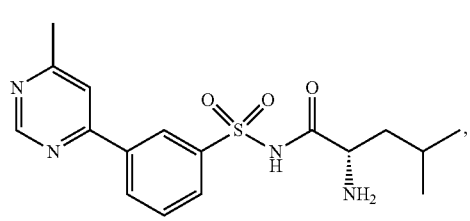
(BM-13)
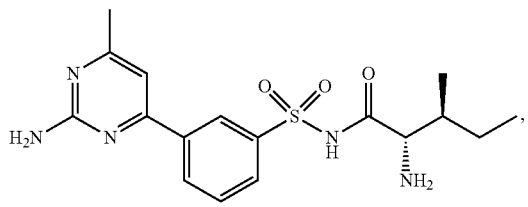
(DG-440)
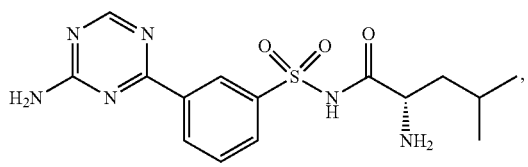
(IK-625)
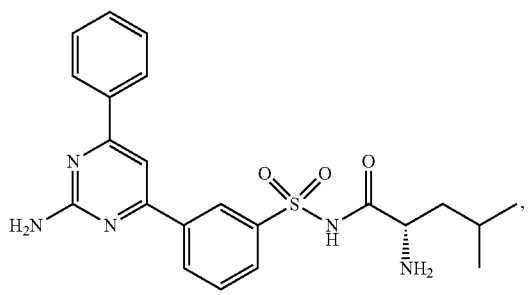
(DG-435)
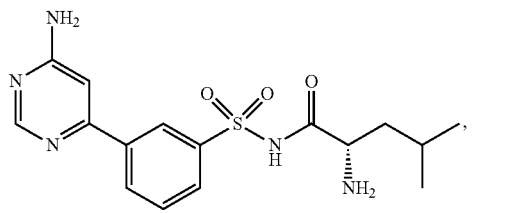
(DG-437)
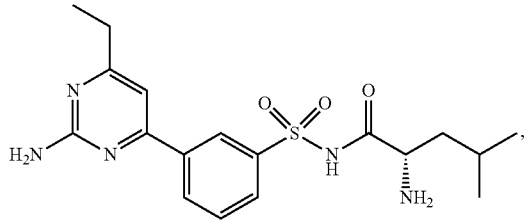
(IK-636)
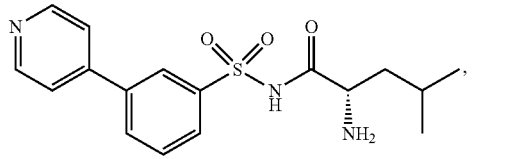
(IK-634)
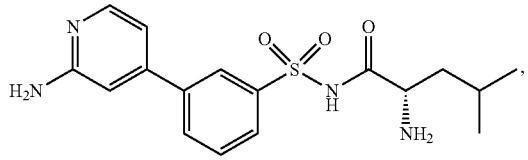

(IK-635)
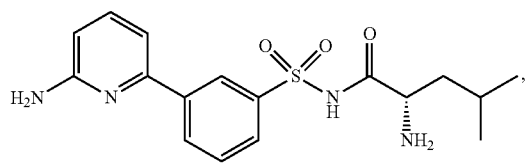
(IK-627)
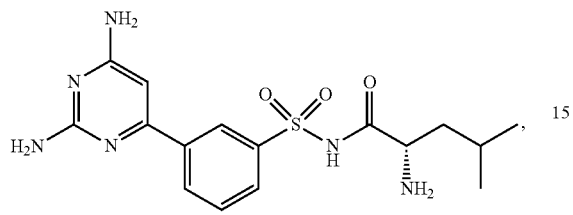
(DG-444)
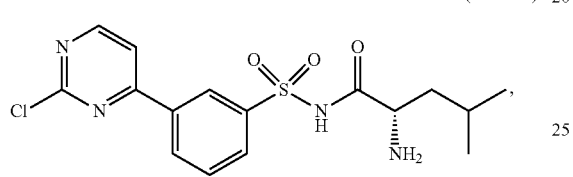
(DG-445)
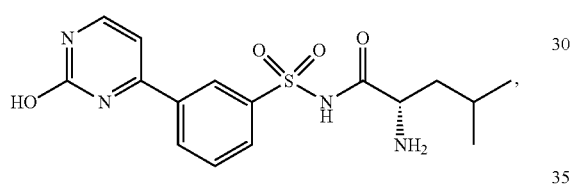
(DG-455)
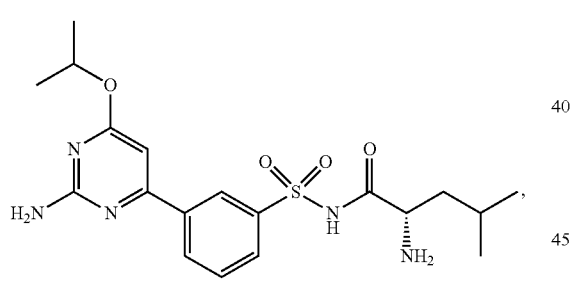
(DG-453)
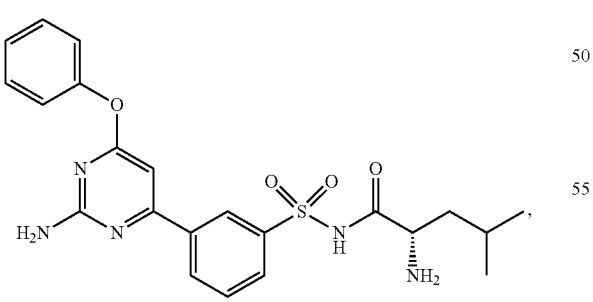
(IK-666)
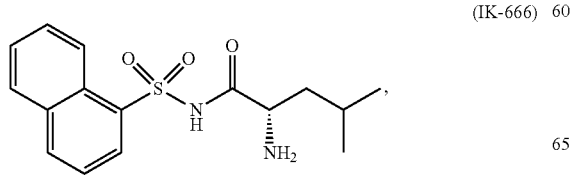
(IK-665)
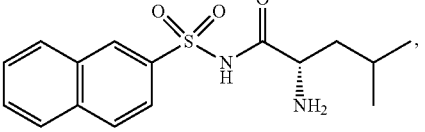
(DG-459)
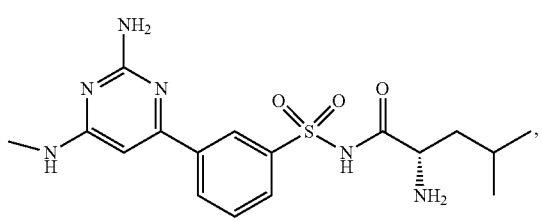
(DG-457)
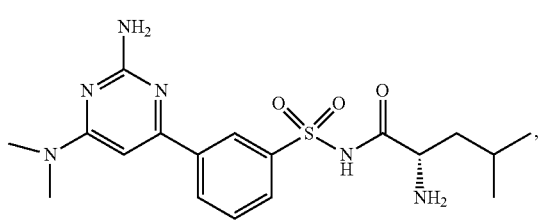
(IK-656)
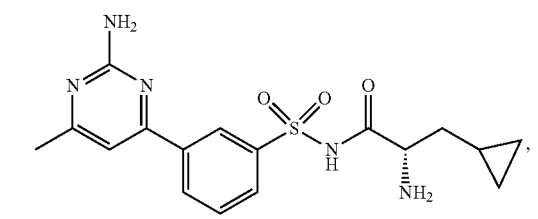
(DG-466)
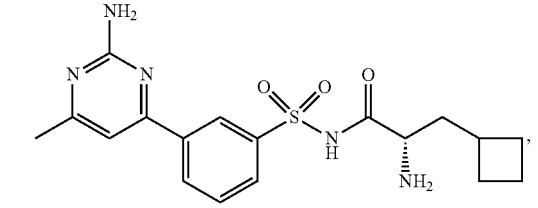
(DG-460)
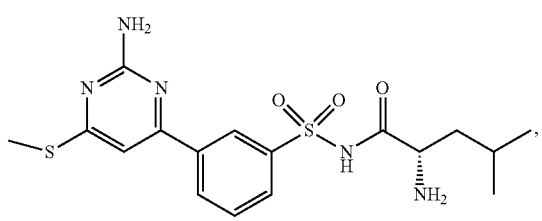
(DG-470)
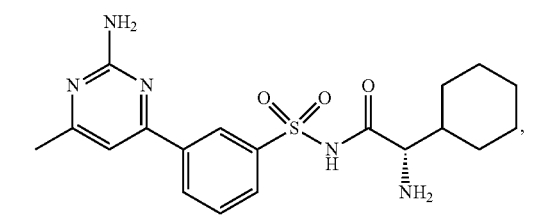

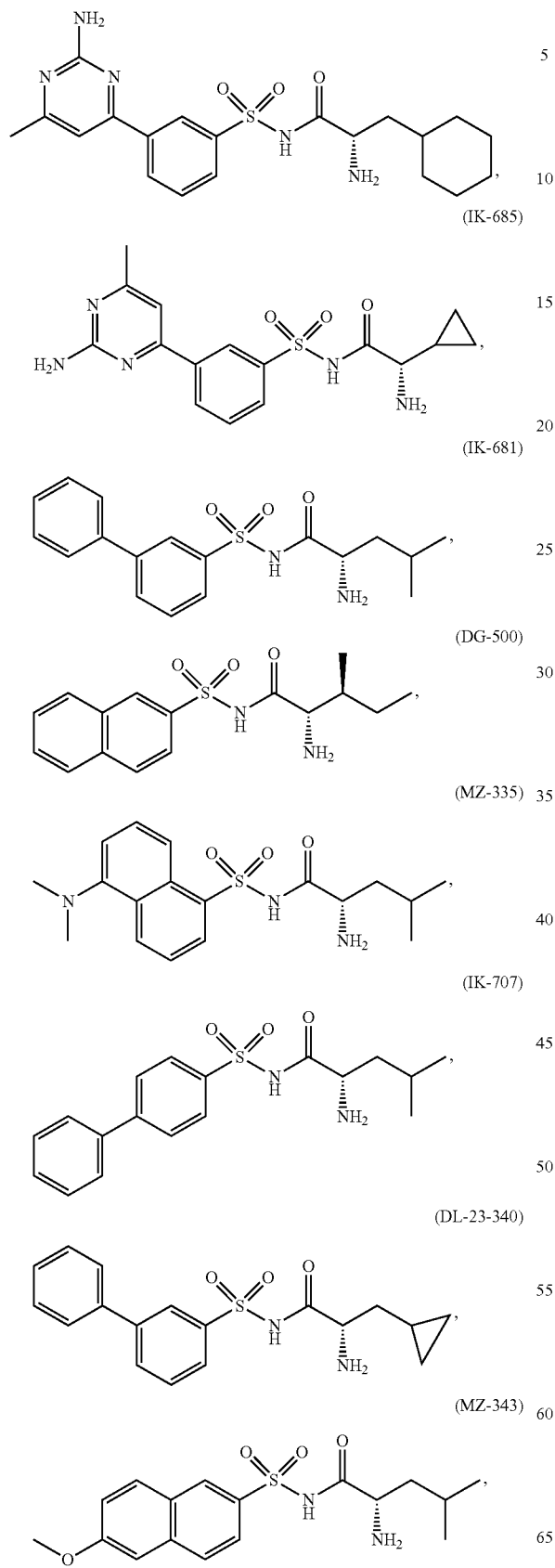
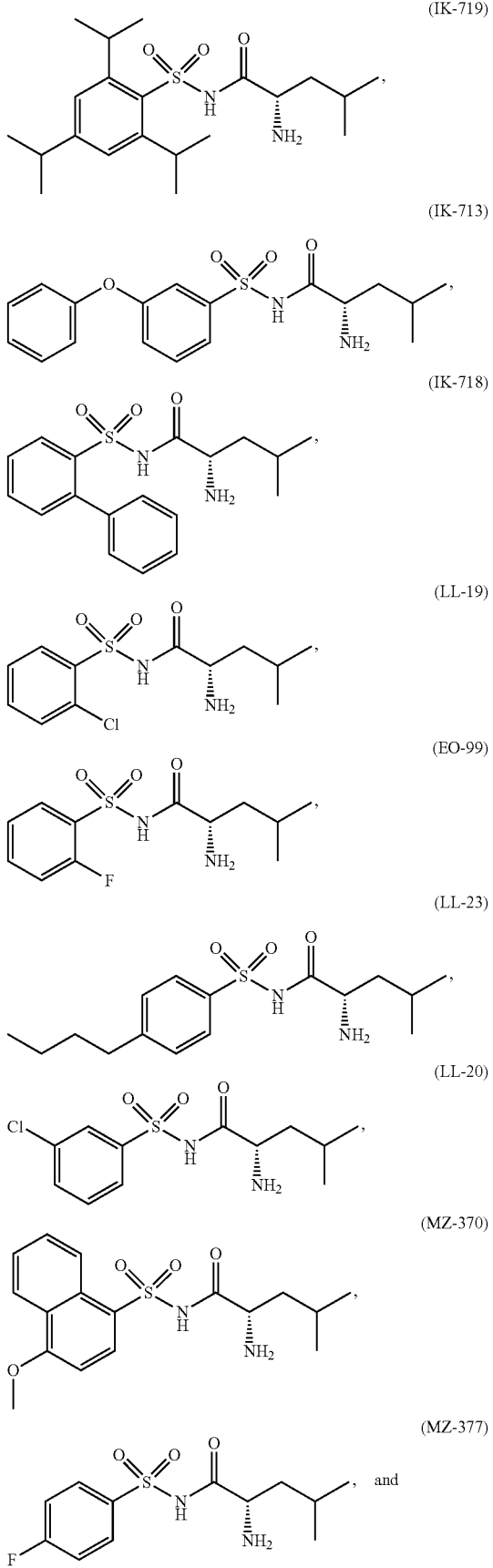

-continued

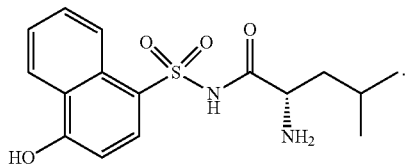
(MZ-368)

2. A compound selected from compounds of the following formula:

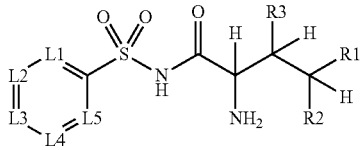

and pharmaceutically acceptable salts thereof,
wherein:
R1 is $C_{1-4}$alkyl;
R2 is $C_{1-4}$alkyl or H;
R3 is $C_{1-4}$alkyl or H;
R1, R2 or R1, R3 together with the atoms to which they are attached may form cyclopropyl, cyclobutyl, cyclopentyl or cyclohexyl;
provided that R2 and R3 are not both hydrogen;
wherein the radical:

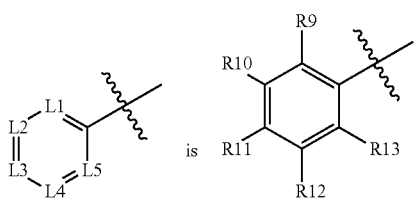

wherein:
R9 is independently H, halo, $C_{1-6}$alkyl, phenyl, or CN, wherein said alkyl is optionally substituted with 1 to 3 substituents selected from halo;
R10 is independently H, halo, $C_{1-6}$alkyl, $C_{2-6}$alkenyl, $C_{2-6}$alkynyl, pyridyl, pyrimidyl, triazinyl, tetrazolyl, purinyl, phenyl, CN, C(=O)$R^e$, C(=O)O$R^e$, C(=O)N($R^e$)$R^f$, O$R^e$, or S(O)$_{0-2}R^e$, wherein said alkyl is optionally substituted with 1 to 3 substituents selected from halo, and wherein said pyridyl, pyrimidyl, triazinyl, tetrazolyl, purinyl, and phenyl are optionally substituted with 1 or 2 substituents independently selected from O$R^e$, N($R^e$)$R^f$, halo, S$R^e$, methyl, ethyl, and phenyl;
R11 is independently H, halo, $C_{2-6}$alkyl, phenyl, or CN;
R12 is independently H or halo;
R13 is independently H, halo, or $C_{1-6}$alkyl;

$R^e$ and $R^f$ are independently H, $C_{1-8}$alkyl, or phenyl, wherein said alkyl is optionally substituted by 1 to 3 substituents selected from halo;
with the proviso that the compound is not:

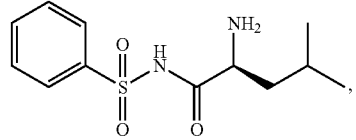

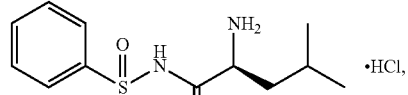

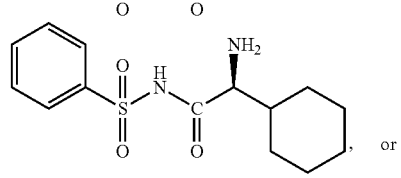

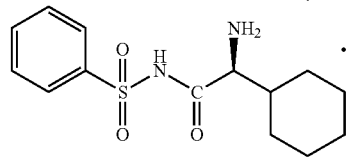

3. A compound according to claim 2, wherein R9 is independently H, halo, $C_{1-6}$alkyl, or phenyl.

4. A compound according to claim 2, wherein R9 is independently H, F, Cl, isopropyl, or phenyl.

5. A compound according to claim 2, wherein R10 is independently H, halo, pyridyl, pyrimidyl, triazinyl, phenyl, or purinyl, wherein said pyridyl, pyrimidyl, triazinyl, purinyl, and phenyl are optionally substituted by 1 or 2 substituents independently selected from NH$_2$, NMe$_2$, SMe, methyl, ethyl, halo, OH, OC$_{1-4}$alkyl, and phenyl.

6. A compound according to claim 2, wherein R10 is independently halo, pyridyl, pyrimidyl, triazinyl, phenyl, or purinyl, wherein said pyridyl, pyrimidyl, triazinyl, purinyl, and phenyl are optionally substituted by 1 or 2 substituents independently selected from NH$_2$, NMe$_2$, SMe, methyl, ethyl, halo, OH, OC$_{1-4}$alkyl, and phenyl.

7. A compound according to claim 2, wherein R10 is halo.

8. A compound according to claim 2, wherein R11 is independently H, $C_{2-6}$alkyl, or phenyl.

9. A compound according to claim 2, wherein R11 is independently H, butyl, isopropyl, or phenyl.

10. A compound according to claim 2, wherein R12 is halo.

11. A compound according to claim 2, wherein R13 is independently H or $C_{1-6}$alkyl.

12. A compound according to claim 2, wherein R13 is independently H, butyl, or isopropyl.

13. A compound according to claim 2, wherein:
R9 is independently H, halo, $C_{1-6}$alkyl, or phenyl;
R10 is independently H, halo, pyridyl, pyrimidyl, triazinyl, purinyl or phenyl, wherein said pyridyl, pyrimidyl, triazinyl, purinyl, and phenyl are optionally substituted by 1 or 2 substituents independently selected from $NH_2$, $NMe_2$, SMe, methyl, ethyl, halo, OH, $OC_{1-4}$alkyl, and phenyl;

R11 is independently H, $C_{2-6}$alkyl, or phenyl;

R12 is independently H or halo; and

R13 is independently H, halo, or $C_{1-6}$alkyl.

14. A compound according to claim 2, wherein:

R9 is independently H, halo, $C_{1-6}$alkyl, or phenyl;

R10 is independently halo, pyridyl, pyrimidyl, triazinyl, purinyl or phenyl, wherein said pyridyl, pyrimidyl, triazinyl, purinyl, and phenyl are optionally substituted by 1 or 2 substituents independently selected from $NH_2$, $NMe_2$, SMe, methyl, ethyl, halo, OH, $OC_{1-4}$alkyl, and phenyl;

R11 is independently H, $C_{2-6}$alkyl, or phenyl;

R12 is independently H or halo; and

R13 is independently H, halo, or $C_{1-6}$alkyl.

15. A compound according to claim 2, wherein:

R9 is independently H, F, Cl, isopropyl, or phenyl;

R10 is independently H, halo, pyridyl, pyrimidyl, triazinyl, phenyl, or purinyl, wherein said pyridyl, pyrimidyl, triazinyl, purinyl and phenyl are optionally substituted by 1 or 2 substituents independently selected from $NH_2$, $NMe_2$, methyl, ethyl, halo, OH, $OC_{1-4}$alkyl, and phenyl;

R11 is independently H, butyl, isopropyl, or phenyl;

R12 is independently H or halo; and

R13 is independently H, F, C, or isopropyl.

16. A compound according to claim 2, wherein:

R9 is independently H, F, Cl, isopropyl, or phenyl;

R10 is independently halo, pyridyl, pyrimidyl, triazinyl, phenyl, or purinyl, wherein said pyridyl, pyrimidyl, triazinyl, purinyl and phenyl are optionally substituted by 1 or 2 substituents independently selected from $NH_2$, $NMe_2$, methyl, ethyl, halo, OH, $OC_{1-4}$alkyl, and phenyl;

R11 is independently H, butyl, isopropyl, or phenyl;

R12 is independently H or halo; and

R13 is independently H, F, Cl, or isopropyl.

17. A compound according to claim 2, wherein:

R9 is H;

R10 is halo;

R11 is H;

R12 is H; and

R13 is H.

18. A pharmaceutical composition comprising at least one compound according to claim 2 in admixture with one or more pharmaceutically acceptable carriers and/or excipients.

19. A pharmaceutical composition comprising at least one compound according to claim 1 in admixture with one or more pharmaceutically acceptable carriers and/or excipients.

* * * * *